US010252073B2

(12) United States Patent
Alphandery et al.

(10) Patent No.: US 10,252,073 B2
(45) Date of Patent: *Apr. 9, 2019

(54) TREATMENT OF CANCER OR TUMOR INDUCED BY THE RELEASE OF HEAT GENERATED BY VARIOUS CHAINS OF MAGNETOSOMES EXTRACTED FROM MAGNETOTACTIC BACTERIA AND SUBMITTED TO AN ALTERNATING MAGNETIC FIELD

(71) Applicant: NANOBACTERIE, Paris (FR)

(72) Inventors: Edouard Alphandery, Paris (FR); Stéphanie Faure, Lyons (FR); Imène Chebbi, Montigny les Cormeilles (FR)

(73) Assignee: NANOBACTERIE, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/433,018

(22) Filed: Feb. 15, 2017

(65) Prior Publication Data
US 2017/0157253 A1 Jun. 8, 2017

Related U.S. Application Data

(62) Division of application No. 13/510,416, filed as application No. PCT/EP2010/067765 on Nov. 18, 2010.

(Continued)

(51) Int. Cl.
*A61N 1/40* (2006.01)
*A61N 2/00* (2006.01)
(Continued)

(52) U.S. Cl.
CPC ............ *A61N 1/406* (2013.01); *A61K 9/0019* (2013.01); *A61K 9/10* (2013.01); *A61K 9/51* (2013.01);
(Continued)

(58) Field of Classification Search
CPC .......... A61N 2/00; A61N 2/002; A61N 2/004; A61N 2/006; A61N 2/008; A61N 2/02;
(Continued)

(56) References Cited

U.S. PATENT DOCUMENTS

| 4,385,119 A | 5/1983 | Blakemore |
| 4,394,451 A * | 7/1983 | Blakemore .............. C12N 1/20 |
| | | 435/168 |

(Continued)

FOREIGN PATENT DOCUMENTS

| WO | 9840049 | 9/1998 |
| WO | 2004064921 | 8/2004 |
| WO | 2007140617 | 12/2007 |

OTHER PUBLICATIONS

L. Han et al. "Research on the Structure and Performance of Bacterial Magnetic Nanoparticles." Journal of Biomaterials Applications, vol. 22, Mar. 2008, pp. 433-448.*

(Continued)

*Primary Examiner* — Carrier R Dorna
(74) *Attorney, Agent, or Firm* — Maier & Maier, PLLC

(57) ABSTRACT

A method for the treatment of tumor(s), tumor cell(s), cancer(s) in a subject by the generation of heat. The latter is produced by chains of magnetosomes extracted from whole magnetotactic bacteria and subjected to an alternating magnetic field. These chains of magnetosomes yield efficient antitumoral activity whereas magnetosomes unbound from the chains or kept within the whole bacteria produce poor or no antitumoral activity. The introduction of various chemicals such as chelating agents and/or transition metals within the growth medium of the bacteria improves the heating properties of the chains of magnetosomes. Moreover, the insertion of the chains of magnetosomes within a lipid vesicle is also suggested in order to favor their rotation in vivo and hence to improve their heating capacity. The (Continued)

vesicle can contain an antitumoral agent together with the chains of magnetosomes, and the agent is released within the tumors by heating the vesicle.

28 Claims, 18 Drawing Sheets

Related U.S. Application Data

(60) Provisional application No. 61/371,385, filed on Aug. 6, 2010, provisional application No. 61/262,260, filed on Nov. 18, 2009.

(51) Int. Cl.

| | |
|---|---|
| A61K 35/74 | (2015.01) |
| C12N 1/20 | (2006.01) |
| C12N 1/38 | (2006.01) |
| A61K 41/00 | (2006.01) |
| A61K 9/00 | (2006.01) |
| A61K 9/10 | (2006.01) |
| A61K 9/51 | (2006.01) |
| A61K 33/26 | (2006.01) |

(52) U.S. Cl.
CPC ............ *A61K 9/5146* (2013.01); *A61K 33/26* (2013.01); *A61K 35/74* (2013.01); *A61K 41/0052* (2013.01); *A61N 2/00* (2013.01); *C12N 1/20* (2013.01); *C12N 1/38* (2013.01)

(58) Field of Classification Search
CPC . A61N 2/06; A61N 2/12; A61N 1/403; A61N 1/406; A61K 35/72; A61K 41/0052; C12N 1/38
See application file for complete search history.

(56) References Cited

U.S. PATENT DOCUMENTS

| | | | |
|---|---|---|---|
| 6,251,365 B1 | 6/2001 | Bäuerlein et al. | |
| 2002/0034537 A1* | 3/2002 | Schulze ................. | A61K 9/127 424/450 |
| 2003/0028071 A1 | 2/2003 | Handy et al. | |
| 2005/0090732 A1 | 4/2005 | Ivkov et al. | |
| 2006/0167313 A1 | 7/2006 | Naik et al. | |
| 2008/0268061 A1 | 10/2008 | Jordan et al. | |

OTHER PUBLICATIONS

Duguet et al., "Magnetic nanoparticles and their applications in medicine", Nanomedicine, 2006, vol. 1, No. 2, pp. 157-158.
Hilger et al., "Electromagnetic Heating of Breast Tumors in Interventional Radiology: in Vitro and in Vivo Studies in Human Cadavers and Mice", Radiology, 2001, vol. 218, pp. 570-575.
Sun et al., "Preparation and Anti-Tumor Efficiency Evaluation of Doxorubicin-Loaded Bacterial Magnetosomes: Magnetic Nanoparticles as Drug Carriers Isolated from Magnetospirillum gryphiswaldense", Biotechnology and Bioengineering, Dec. 2008, vol. 101, No. 6, pp. 1313-1320.
Genc et al., "Curvature-Tuned Preparation of Nanoliposomes", Langmuir, 2009, vol. 25, No. 21, pp. 12604-12613.
Widler et al., "Highly Potent Geminal Bisphosphonates. From Pamidronate Disodium (Aredia) to Zoledronic Acid (Zometa)", Journal of Medicinal Chemistry, 2002, vol. 45, No. 17, pp. 3721-3728.
Neves et al., "Synthesis, characterization and biodistribution of bisphosphonates Sm-153 complexes: correlation with molecular modeling interaction studies", Nuclear Medicine and Biology, 2002, vol. 29, No. 3, pp. 329-338.
Shinoda et al., "Structure-Activity Relationships of Various Bisphosphonates", Calcified Tissue International, 1983, vol. 35, No. 1, pp. 87-99.
Merrell et al., "Inhibition of the mevalonate pathway and activation of p38 MAP kinase are independently regulated by nitrogen-containing bisphosphonates in breast cancer cells", European Journal of Pharmacology, 2007, vol. 570, No. 1-3, pp. 27-37.
Allen, Theresa M., "Long-circulating (sterically stabilized) liposomes for targeted drug delivery", Trends in Pharmacol. Sci. (TiPS), 1994, vol. 15, No. 7, pp. 215-220.
Blume et al., "Liposomes for the sustained drug release in vivo", Biochimica et Biophysica Acta, 1990, vol. 1029, No. 1, pp. 91-97.
Gabizon et al., "The role of surface charge and hydrophilic groups on liposome clearance in vivo", Biochimica et Biophysica Acta, 1992, vol. 1103, No. 1, pp. 94-100.
Lalatonne et al., "Influence of short-range interactions on the mesoscopic organization of magnetic nanocrystals", Physical Review E, 2005, vol. 71, pp. 011404 to 011404-10.
Brusentsov et al., "Evaluation of ferromagnetic fluids and suspensions for the site-specific radiofrequency-induced iyperthermia of MX11 sarcoma cells in vitro", Journal of Magnetism and Magnetic Materials, 2001, vol. 225, pp. 113-117.
Chan et al., "Physical Chemistry and in Vivo Tissue Heating Properties of Colloidal Magnetic Iron Oxides with Increased Power Absorption Rates", Scientific and Clinical Applications of Magnetic Carriers, Plenum Press, 1997, pp. 507-618.
Mosmann, Tim, "Rapid Calorimetric Assay for Cellular Growth and Survival: Application to Proliferation and Cytotoxicity Assays", Journal of Immunological Methods, 1983, vol. 65, pp. 55-63.
Zhou et al., "Sub-cellular accumulation of magnetic nanoparticles in breast tumors and metastases", Biomaterials, 2006, vol. 27, No. 9. pp. 2001-2008.
Cailleau et al., "Breast Tumor Cell Lines from Pleural Effusions", J. Natl. Cancer Inst., 1974, vol. 53, No. 3, pp. 661-674.
Duntarulo, Susana, "Iron, oxidative stress and human health", Molecular Aspects Medicine, 2005, vol. 26, No. 4-5, pp. 299-312.
Nikitin et al., "New type of biosensor based on magnetic nanoparticle detection", Journal of Magnetism and Magnetic Materials, 2007, vol. 311, No. 1, pp. 445-449.
Yoshino et al., Magnetic Cell Separation Using Nano-Sized Bacterial Magnetic Particles With Reconstructed Magnetosome Membrane, Biotechnology and Bioengineering, 2008, vol. 101, No. 3, pp. 470-477.
Xie et al., Production, Modification and Bio-Applications of Magnetic Nanoparticles Gestated by Magnetotactic Bacteria, Nano Res., 2009, vol. 2, No. 4, pp. 261-278.
Jordan et al., "Increase of the specific absorption rate (SAR) by magnetic fractionation of magnetic fluids", Journal of Nanoparticle Research, 2003, vol. 5, pp. 597-600.
Alphandery et al., "Difference between the Magnetic Properties of the Magnetotactic Bacteria and Those of the Extracted Magnetosomes: Influence of the Distance between the Chains of Magnetosomes", J. Phys. Chem. C, 2008, pp. 12304-12309, vol. 112, No. 32.
Alphandery et al., "Assemblies of Aligned Magnetotactic Bacteria and Extracted Magnetosomes: What is the Main Tactor Responsible for the Magnetic Anisotropy?", ACSNANO, 2009, pp. 1539-1547, vol. 3., No. 6.
Arakaki et al., "Formation of magnetite by bacteria and its application", J.R. Soc. Interface, 2008, pp. 977-999, vol. 5.
Bae et al., "Intelligent biosynthetic nanobiomaterials for hyperthermic combination chemotherapy and thermal drug targeting of HSP90 inhibitor geldanamycin", J. Controlled Release, 2007, pp. 16-23, vol. 122.
Bazylinski et al., "Magnetosome Formation in Prokaryotes", Nature Reviews/Microbiology, Mar. 2004, pp. 217-230, vol. 2.
Benoit et al., "Visualizing Implanted Tumors in Mice with Magnetic Resonance Imaging Using Magnetotactic Bacteria", Clin. Cancer Res., Aug. 2009, pp. 5170-5177, vol. 15, No. 16.
Chen et al., "Characteristics and genesis of maghemite in Chinese loess and paleosols: Mechanism for magnetic susceptibility enhancement in paleosols", Earth and Planetary Science Letters, 2005, pp. 790-802, vol. 240.

(56) References Cited

OTHER PUBLICATIONS

Ciofani et al., "A bi-modal approach against cancer: Magnetic alginate nanoparticles for combined chemotherapy and hyperthermia", Medical Hypotheses, 2009, pp. 80-82, vol. 73.
Denardo et al., "Development of Tumor Targeting Bioprobes (111 In-Chimeric L6 Monoclonal Antibody Nanoparticles) for Alternating Magnetic Field Cancer Therapy", Clin. Cancer Res., Oct. 2005, pp. 7087s-7092s, vol. 11, No. 19 Suppl.
Denardo et al., "Thermal Dosimetry Predictive of Efficacy of 111 In-ChL6 Nanoparticle AMF-Induced Thermoablative Therapy for Human Breast Cancer in Mice", J. Nuclear Med., Mar. 2007, pp. 437-444, vol. 48, No. 3.
Dutz et al., "Hysteresis losses of magnetic nanoparticle powders in the single domain size range", J. Magnetism and Magnetic Materials, 2007, pp. 305-312, vol. 308.
Faivre et al., "Magnetotactic Bacteria and Magnetosomes", Chem. Rev., 2008, pp. 4875-4898, vol. 108, No. 11.
Franco et al., "Temperature dependence of magnetic anisotropy in nanoparticles of CoxFe(3-x)O4", J. Magnetism and Magnetic Materials, 2008, pp. 709-713, vol. 320.
Grunberg et al., "Biochemical and Proteomic Analysis of the Magnetosome Membrane in Magnetospirillum gryphiswaldense",Appl. Environ. Microbiol., Feb. 2004, pp. 1040-1050, vol. 70, No. 2.
Habib et al. "Evaluation of iron-cobalt/ferrite core-shell nanoparticles for cancer thermotherapy", J. Appl. Phys., 2008, pp. 07A307-1-07A307-3, vol. 103.
Hergt et al., "Physical Limits of Hyperthermia Using Magnetite Fine Particles", IEEE Transactions of Magnetics, Sep. 1998, pp. 3745-3754, vol. 34, No. 5.
Hergt et al., "Magnetic properties of bacterial magnetosomes as potential diagnostic and therapeutic tools", J. Magnetism and Magnetic Materials, 2005, pp. 80-86, vol. 293.
Hergt et al., "Magnetic particle hyperthermia: nanoparticle magnetism and materials development for cancer therapy", J. Phys: Condens. Matter, 2006, pp. S2919-S2934, vol. 18.
Ito et al., "Heat shock protein 70 expression induces antitumor immunity during intracellular hyperthermia using magnetite nanoparticles", Cancerl Immunol. Immunother., 2003, pp. 80-88, vol. 52.
Ito et al., "Complete Regression of Mouse Mammary Carcinoma with a Size Greater than 15 mm by Frequent Repeated Hyperthermia Using Magnetite Nanoparticles", J. Biosci. and Bioeng., 2003, pp. 364-369, vol. 96, No. 4.
Ito et al.,"Magnetite nanoparticle-loaded anti-HER2 immunoliposomes for combination of antibody therapy with hyperthermia", Cancer Letters, 2004, pp. 167-175, vol. 212.
Ito et al., "Cancer immunotherapy based on intracellular hyperthermia using magnetite nanoparticles: a novel concept of 'heat-controlled necrosis' with heat shock protein expression", Cancer Immunol. Immunother., 2006, pp. 320-328, vol. 55.
Ivkov et al., "Application of High Amplitude Alternating Magnetic Fields for Heat Induction of Nanoparticles Localized in Cancer", Clin. Cancer Res., Oct. 2005, pp. 7093s-7103s, vol. 11, No. 19 Suppl.
Johannsen et al., "Clinical hyperthermia of prostate cancer using magnetic nanoparticles: Presentation of a new interstitial technique", Int. J. Hyperthermia, Nov. 2005, pp. 637-647, vol. 21, No. 7.
Johannsen et al., "Thermotherapy of Prostate Cancer Using Magnetic Nanoparticles Feasibility, Imaging, and Three-Dimensional Temperature Distribution", European Urology, 2007, pp. 1653-1662, vol. 52.
Jordan et al., "Inductive heating of ferromagnetic particles and magnetic fluids: physical evaluation of their potential for hyperthermia", Int. J. Hyperthermia, 1993, pp. 51-68, vol. 9, No. 1.
Kawai et al., "Anticancer Effect of Hyperthermia on Prostate Cancer Mediated by Magnetite Cationic Liposomes and Immune-Response Induction in Transplanted Syngeneic Rats", The Prostate, 2005, pp. 373-381, vol. 64.

Kawai et al., "Effect of Heat Therapy Using Magnetic Nanoparticles Conjugated With Cationic Liposomes on Prostate Tumor in Bone", The Prostate, 2008, pp. 784-792, vol. 68.
Kikumori et al., "Anti-cancer effect of hyperthermia on breast cancer by magnetite nanoparticle-loaded anti-HER2 Immunoliposomes", Breast Cancer Res. Treat., 2009, pp. 435-441, vol. 113.
Kobayashi et al., "Experimental observation of magnetosome chain collapse in magnetotactic bacteria: Sedimentological, paleomagnetic, and evolutionary implications", Earth and Planetary Science Letters, 2006, pp. 538-550, vol. 245.
Komeili A., "Molecular Mechanisms of Magnetosome Formation", Annu. Rev. Biochem., 2007, pp. 351-66, vol. 76.
Kundu et al., "On the change in bacterial size and magnetosome features for Magnetospirillum magnetotacticum (MS-1) under high concentrations of zinc and nickel", Biomaterials, 2009, pp. 4211-4218, vol. 30.
Lang et al., "Biogenic nanoparticles: production, characterization, and application of bacterial magnetosomes", J. Phys.: Condens. Matter, 2006, pp. S2815-S2828, vol. 18.
Ma et al., "Size dependence of specific power absorption of Fe3O4 particles in AC magnetic field", J. Magnetism and Magnetic Materials, 2004, pp. 33-39, vol. 268.
Maier-Hauff et al., "Intracranial thermotherapy using magnetic nanoparticles combined with external beam radiotherapy: Results of a feasibility study on patients with glioblastoma multiforme", J. Neurooncol., 2007, pp. 53-60, vol. 81.
Martina et al., "Generation of Superparamagnetic Liposomes Revealed as Highly Efficient MRI Contrast Agents for in Vivo Imaging", J. Am. Chem. Soc., 2005, pp. 10676-10685, vol. 127, No. 30.
Mornet et al., "Magnetic nanoparticle design for medical diagnosis and therapy", J. Mater. Chem., 2004, pp. 2161-2175, vol. 14.
Oberdorster et al., "Nanotoxicology: An Emerging Discipline Evolving from Studies of Ultrafine Particles", Environ. Health Perspectives, Jul. 2005, pp. 823-839, vol. 113, No. 7.
Overgaard, "Effect of Hyperthermia on Malignant Cells in Vivo. A Review and a Hypothesis", Cancer, Jun. 1977, pp. 2637-2646, vol. 39.
Ponce et al., "Hyperthermia mediated liposomal drug delivery", Int. J. Hyperthermia, May 2006, pp. 205-213, vol. 22, No. 3.
Staniland et al., "Controlled cobalt doping of magnetosomes in vivo", Nature Nanotechnology, Mar. 2008, pp. 158-162, vol. 3.
Sun et al., "In vitro and in vivo antitumor effects of doxorubicin loaded with bacterial magnetosomes (DBMs) on H22 cells: The magnetic bio-nanoparticles as drug carriers", Cancer Letters, 2007, pp. 109-117, vol. 258.
Sun et al., "High-yield growth and magnetosome formation by Magnetospirillum gryhiswaldense MSR-1 in an oxygen-controlled fermentor supplied solely with air", Appl. Microbiol. Biotechnol., 2008, pp. 389-397, vol. 79.
Sun et al., "Targeted Distribution of Bacterial Magnetosomes Isolated from Magnetospirillum gryphiswaldense MSR-1 in Healthy Sprague-Dawley Rats", J. Nanosci. Nanotechnol., 2009, pp. 1881-1885, vol. 9, No. 3.
Sun et al., "Biocompatibility of bacterial magnetosomes: Acute toxicity, immunotoxicity and cytotoxicity", Nanotoxicology, 2010, Early Online, pp. 1-13.
Tackett et al., "Magnetic and optical response of tuning the magnetocrystalline anisotropy in Fe3o4 nanoparticle ferrolluids by Co doping", J. Magnetism and Magnetic Materials, 2008, pp. 2755-2759, vol. 320.
Tai et al., "Thermosensitive liposomes entrapping iron oxide nanoparticles for controllable drug release", Nanotechnology, 2009, 135101 (9 pages), vol. 20.
Thiesen et al., "Clinical applications of magnetic nanoparticles for hyperthermia", Int. J. Hyperthermia, Sep. 2008, pp. 467-474, vol. 24, No. 6.
Timko et al., "Magnetic properties and heating effect in bacterial magnetic nanoparticles", J. Magnetism and Magnetic Materials, 2009, pp. 1521-1524, vol. 321.
Xiang et al., "Purified and sterilized magnetosomes from Magnetospirillum gryphiswaldense MSR-1 were not toxic to mouse fibroblasts in vitro", Letters in Applied Microbiology, 2007, pp. 75-81, vol. 45.

(56) References Cited

OTHER PUBLICATIONS

Zhang et al., "Surface modification of superparamagnetic magnetite nanoparticles and their intracellular uptake", Biomaterials, 2002, pp. 1553-1561, vol. 23.

International Search Report PCT/EP2010/067765 dated Mar. 16, 2011, 3 pages.

Japanese Office Action dated Apr. 23, 2018 in corresponding Japanese Patent Application No. 2016-031157 with English translation of Japanese Office Action.

Buathong et al., "Thermal, Magnetic, and Luminescent Properties of Dendronized Ferrite Nanoparticles", Journal of Physical Chemistry C, vol. 113, No. 28, Jul. 16, 2009 (Jul. 16, 2009), pp. 12201-12212, XP055275676, US SSN: 1932-7447, DOI: 10.1021/jp902046d, Abstract Only.

Denardo et al., "Thermal Dosimetry Predictive of Efficacy of In-ChL6 Nanoparticle AMF-Induced Thermoablative Therapy for Human Breast Cancer in Mice," J. Nuclear Med., Mar. 2007, pp. 437-444, vol. 48 No. 3.

Lang et al., "Expression of Green Fluorescent Protein Fused to Magnetosome Proteins in Microaerophilic Magnetotactic Bacteria", Applied and Environmental Microbiology, vol. 74, No. 15, Jun. 6, 2008 (Jun. 6, 2008), pp. 4944-4953.

Mandal et al., "Encapsulation of Magnetic and Fluorescent Nanoparticles in Emulsion Droplets", Langmuir, vol. 21, No. 9, 2005, American Chemical Society Published on Web Mar. 24, 2005, pp. 4175-4179.

Purushotham et al, "Thermoresponsive core-shell magnetic nanoparticles for combined modalities of cancer therapy", Nanotechnology, IOP, Bristol, GB, vol. 20, No. 30, Jul. 29, 2009 (Jul. 29, 2009), p. 305101, Abstract Only.

Xie et al., "Production, Modification and Bio-Applications of Magnetic Nanoparticles Gestated by Magnetotactic Bacteria", Dec. 31, 2009 (Dec. 31, 2009), © Tsinghua University Press and Springer-Verlag 2009, pp. 1-24.

Karen Grunberg, et al., "A Large Gene Cluster Encoding Several Magnetosome Proteins Is Conserved in Different Species of mgnetotactic Bacteria," Applied and Environmental Microbiology, Oct. 2001, pp. 4573-4582.

Akira Ito et al.—Drug Delivery System, 2002, vol. 17, pp. 347-354.

Morimoto et al., "Targeting Technology Utilizing Magnetic Microparticulate System for Cancer Therapy," Nihon Rinshou, 1998, vol. 56, No. 3, pp. 649-656.

Ingrid Hilger et al—Effects of Magnetic Thermoablation in Muscle Tissue Using Iron Oxide Particles: An in Vitro Study—PMID: 10719826, Issn Print: 0020-9996. Publication Date: Mar. 1, 2000. pp. 1-2.

Azuma Taoka et al.—Spatial Localizations of Mam22 and Mam12 in the Magnetosomes of Magnetospirillum magnetotacticum—Journal of Bacteriology, Jun. 2006. p. 3805-3812, 0021-9193/06/$08.00+0 doi:10.1128/Jb.00020-06, vol. 188, No. 11.

Fernando Vereda et al.—Physical Properties of Elongated Magnetic Particles: Magentization and Friction Coefficient Anisotropies—ChemPhysChem 2009, pp. 1165-1179.

* cited by examiner

TREATMENT OF CANCER OR TUMOR INDUCED BY THE RELEASE OF HEAT GENERATED BY VARIOUS CHAINS OF MAGNETOSOMES EXTRACTED FROM MAGNETOTACTIC BACTERIA AND SUBMITTED TO AN ALTERNATING MAGNETIC FIELD

FIELD OF THE INVENTION

The present invention is related to the in vivo heat treatment of cells or tissues, especially tumor(s) or tumor cells, using the heat generated in situ by magnetic elements submitted to an alternating magnetic field. The invention is related in particular to heat therapy using hyperthermia or thermoablation. The type of magnetic element described in this disclosure is a chain of iron oxide nanoparticles synthesized through a biological process.

BRIEF SUMMARY OF THE INVENTION

This invention describes a thermotherapy, which can be used to destroy cancer, tumor(s), or tumor cells. The heat is generated by chains of bacterial magnetosomes, which are extracted from magnetotactic bacteria. The chains of magnetosomes used in the thermotherapy may be obtained by cultivating the bacteria in the various following conditions:

(1) Magnetotactic bacteria (e.g. ATCC 700274) are cultivated in a standard growth medium (e.g. ATCC Medium 1653 or a growth medium similar to ATCC Medium 1653 suitable to grow the strain ATCC 700274).

(2) Magnetotactic bacteria are cultivated in a growth medium, which contains the standard growth medium such as that mentioned in (1) and preferably an additive, which is a transition metal. Examples of transition metals, which can be used, are Cobalt, Nickel, Copper, Zinc, Manganese and Chrome.

(3) Magnetotactic bacteria are cultivated in a growth medium, which contains the standard growth medium such as that mentioned in (1) and preferably an additive, which is a chelating agent. By chelating agent, it is meant preferably an organic compound, which is a monodentate or polydentate ligand able to form a complex with the cations derived from iron or anyone of the other transition metals.

(4) Magnetotactic bacteria are cultivated in a growth medium, which contains the standard ATCC growth medium such as that mentioned in (1) and the two additives mentioned in (2) and (3).

The presence of additives within the bacterial growth medium yields improved magnetosome heating efficiency (both in solution and in vivo). Extracted chains of magnetosomes obtained by synthesizing the bacteria in either one of the four different growth media described in (1) to (4) can also be encapsulated within a lipid vesicle in the presence or not of an active principle and used as such in the thermotherapy.

BACKGROUND

Recently, great efforts have been devoted to synthesizing magnetic nanoparticles, which are able to induce the production of heat when an oscillating magnetic field is applied to them (Duguet et al., *Nanomed.*, 2006, 1, 157-168) and that can be easily manipulated using magnetic fields. These features have led to the idea that magnetic nanoparticles may be helpful in the destruction or elimination of tumors through hyperthermia or thermoablation or that they can be used to release drugs at specific localized regions of the body. This field of research is often designated as alternating magnetic field (AMF) hyperthermia since it requires the application of an alternating magnetic field to induce the production of heat by the nanoparticles. In previous work, the heat has been induced using chemically synthesized nanoparticles, mainly in the form superparamagnetic iron oxide nanoparticles (SPION), which were either mixed in solution or mixed with cells or administered to a living organism. The anti-tumoral activity of these heated nanoparticles has also been evaluated both on animal models and clinically on humans. An overview of the work carried out previously is presented in the references listed hereafter (Bae et al., *J. Controlled Release*, 2007, 122, 16-23; Ciofani et al., *Med. Hypotheses*, 2009, 73, 80-82; De Nardo, *Clin. Cancer Res.*, 2005, 11, 7087s-7092s; De Nardo et al., *J. Nucl. Med.*, 2007, 48, 437-444; Higler et al., *Radiology*, 2001, 218, 570-575; Ito et al., *Cancer. Sci.*, 2003, 94, 308-313; Ito et al., *J. Biosci. Bioeng.*, 2003, 96, 364-369; Ito et al, *Cancer Lett.*, 2004, 212, 167-175; Ito et al., *Cancer Immunol. Immun.*, 2006, 55, 320-328; Johannsen et al., *Int. J. Hyperthermia*, 2005, 21, 637-647; Johannsen et al., *Int. J. Hyperthermia*, 2007, 52, 1653-1662; Jordan et al., Int. J. Hyperthermia, 1993, 9, 51-68; Kawai et al., *Prostate*, 2005, 64, 373-381; Kawai et al., *Prostate*, 2008, 68, 784-792; Kikumori et al., *Breast Cancer Res. Treat.*, 2009, 113, 435-441, Maier-Hauff et al., *J. Neurooncol.*, 2007, 81, 53-60; Oberdörster et al., *Environ. Health Persp.*, 2005, 113, 823-839; Ponce et al., *Int. J. Hyperthermia*, 2006, 22, 205-213; Tai et al., *Nanotechnology*, 2009, 20, 135101; Thisen et al., *Int. J. Hyperthermia*, 2008, 24, 467-474).

At this time, there are at least three companies that develop cancer therapy using the heat generated by magnetic nanoparticles when the latter are exposed to an alternating magnetic field. These companies are Sirtex (an Australian company), Magforce (a German company) and Aspen Medisys (an American company previously Aduro Biotech and Triton Biosystem). The patterns that have been published by these companies describe various ways of using the heat generated by chemically synthesized magnetic nanoparticles for cancer therapy (Sirtex: US2006167313 or WO 2004/064921; Triton Biosystems now Aspen Medisys, LLC: US2003/0028071; Magforce: US2008/0268061).

Although significant progress has been made in the area of nanoparticle cancer therapy, concerns have been raised regarding the toxicity induced by the presence of the chemically synthesized nanoparticles in the body (Habib et al., *J. Appl. Phys.*, 2008, 103, 07A307-1-07A307-3). In order to minimize the potential side effects arising during the clinical treatments, the quantity of nanoparticles administered needs to be as small as possible while still retaining their desired effect. For that, magnetic nanoparticles have to generate a sufficiently large amount of heat, i. e. significant specific absorption rates (SAR).

Therefore, there is a need for magnetic nanoparticles having a higher heating capacity than that usually obtained with chemically synthesized nanoparticles. This will be useful to reduce the amount of magnetic material needed to heat a biological tissue or cell. This can be achieved by using nanoparticles with either large volumes or with high magnetocrystalline anisotropy (Hergt et al., *J. Phys. Condens. Matter*, 2006, 18, S2919-S2934).

There is also a need to develop magnetic nanoparticles that can have such good properties and the ability to target a tissue or a cell.

In part due to their large volume, the magnetosomes synthesized by magnetotactic bacteria produce a larger amount of heat than the chemically synthesized nanoparticles when they are subjected to an oscillating magnetic field. This has been shown for bacterial magnetosomes mixed in solution (Hergt et al., *J. Phys. Condens. Matter*, 2006, 18, S2919-S2934; Hergt et al., *J. Magn. Magn. Mater.*, 2005, 293, 80-86; Timko et al., *J. Mag. Mag. Mat.*, 2009, 321, 1521-1524). In the above references, the type of bacterial magnetosomes used to carry out the experiments has not been clearly identified.

The magnetosomes are intracellular, membrane-bounded, nanometer-sized single-magnetic-domain crystals of the iron oxide magnetite ($Fe_3O_4$) or iron sulfide greigite ($FeS_4$) that are synthesized by magnetotactic bacteria. The magnetosomes composed of magnetite can become oxidized to maghemite after extraction from the bacteria. The magnetosomes are usually arranged as a chain within the bacteria, but individual magnetosomes can also be found. The bacteria appear to use the magnetosomes to navigate in the Earth's geomagnetic field and help them to locate and maintain optimal conditions for their growth and survival (Bazylinski et al., *Nat. Rev. Microbiol.*, 2004, 2, 217-230). Magnetosomes and magnetosome magnetite crystals have been shown to be useful in a number of scientific, commercial and health applications. For example, they can be used to detect single nucleotide polymorphism, to extract DNA or to detect magnetically bio-molecular interactions. They can also be used in immunoassay and receptor-binding assay or in cell separation (Arakaki et al., *J. R. Soc. Interface*, 2005, 5, 977-999). It has been suggested that bacterial magnetosomes could be inserted within liposomes for drug delivery purposes (U.S. Pat. No. 6,251,365B1). However, very few experimental proofs have been given in this pattern and the heating capability of such liposome has not been demonstrated or suggested. The anti-cancerous activity of a complex formed by bacterial magnetosomes and doxorubicin has been shown experimentally (Sun et al., *Cancer Lett*, 2007, 258, 109-117). In this case, the anti-cancerous activity is due to the presence of doxorubicin and not to a treatment induced by heat. In the end, bacterial magnetosomes have not been proven to be useful for in vitro or in vivo heat treatment of tumor or cancer cells.

Finally, two recent studies briefly address the issue raised by the potential toxicity of bacterial magnetosomes in rats and don't report any sign of toxicity (Sun et al., *J. Nanosci. Nanotechnol.*, 2009, 9, 1881-1885; Sun et al, Sun et al, *Nanotoxicology*, 2010, 4, 271-283).

DESCRIPTION OF THE INVENTION

Different types of bacterial magnetosomes (organized in chains or not and contained within the bacteria or extracted from the bacteria) can be efficient to generate heat in a solution when they are exposed to an alternating magnetic field. However, as demonstrated in this disclosure, only magnetosomes organized in chains and isolated from magnetotactic bacteria yield efficient anti-tumoral activity. Indeed, bacterial magnetosomes contained within whole AMB-1 magnetotactic bacteria and individual magnetosomes (extracted from the bacteria and treated with sodium dodecyl sulfate (SDS) and heat) were also studied. Despite their good heating properties in solutions, these two types of bacterial magnetosomes appeared to yield no or much less in vivo antitumoral activity than the chains of magnetosomes according to the invention. The impact of the organization in chains of the bacterial magnetosomes on the efficiency of the thermotherapy is an important contribution of the invention.

The present invention is related to the in vivo treatment of tissues or cells, especially of tumor(s) or tumor cell(s), using the heat generated in situ by chains of magnetosomes, which are isolated and extracted from whole magnetotactic bacteria. The type of tumor, which can be treated, is preferentially a solid tumor. These chains may be used as such or encapsulated within a vesicle. The heat is produced by submitting the chains of magnetosome to an alternating magnetic field (also called oscillating magnetic field).

The present invention is also related to chains of magnetosomes for use in the treatment of tumor(s) by heat therapy, preferentially of a solid tumor. The chains may be used as such or encapsulated within a vesicle.

The present invention is also related to chains of magnetosomes as a drug, especially as a drug for anti-tumoral treatment. The chains may be used as such or encapsulated within a vesicle.

The invention is also related to the use of chains of magnetosomes as a mean of heating, especially of a living tissue or living cells in vivo.

The invention is also related to the use of chains of magnetosomes as a drug which enables the treatment of tumor(s) and/or tumor cells through a heating method The following description of embodiments and features do apply to the method of treatment and to the use of the chains of magnetosomes.

It is important to point out that the invention is related to the administration of chains of magnetosomes to a patient in need. However, it is possible that after administration in the organism a small amount of chains of magnetosomes is altered; the alteration of these chains of magnetosomes may result in the formation of longer or shorter chains than those administered and less probably in the apparition of individual magnetosomes.

The magnetosomes administered during the therapy are in the form of chains of magnetosomes. By definition, these chains of magnetosomes are isolated from the magnetotactic bacteria. This means that they are not contained within the bacteria. Preferably, the chains have been extracted from the bacteria used for their production and isolated from the cellular fragments. These chains of magnetosomes contain preferably between 2 and 30 magnetosomes, typically between 4 and 20 magnetosomes. Most of the magnetosomes belonging to these chains possess crystallographic directions and preferably also easy axes orientated in the direction of the chain elongation, which is usually [111] (Alphandéry et al., *ACS Nano.*, 2009, 3, 1539-1547). Consequently, the chains of magnetosomes possess a magnetic anisotropy, which is stronger than that of individual magnetosomes. As a result, strong aggregation of the chains of magnetosomes is prevented. When several chains of magnetosomes containing typically between 4 and 20 magnetosomes interact, it results in the formation of a longer chain of magnetosomes, containing typically more than 4 to 20 magnetosomes. The length of a chain of magnetosomes is preferably less than 1200 nm, more preferably less than 600 nm, most preferably less than 300 nm. The arrangement in chains of the magnetosomes yields several properties, which are advantageous for in vivo heating. Due to their arrangement in chains, the magnetosomes are not prone to aggregation and also possess a stable magnetic moment. Both of these properties favor the rotation of the chains of magnetosomes and therefore the production of heat through this mechanism. The arrangement in chains of the magnetosomes also provides an interaction with the eukaryotic cells, which is advantageous due to their low level of aggregation. This interaction results in an internalization of the chains of magnetosomes within the eukaryotic cells. For example, as described in more details in example 4, a significant percentage of cells become magnetic when the chains of magnetosomes are mixed with the cells while the alternating magnetic field is applied. In an embodiment, the chains of magnetosomes penetrate within the eukaryotic cells when the alternating magnetic field is applied, thus enabling the destruction of the cells through the mechanism of intracellular hyperthermia. This mechanism is potentially more efficient than extra-cellular hyperthermia since it destroys the cells from the inside. On the other hand, a very small percentage of magnetic cells is obtained when the cells are mixed in the presence of the individual magnetosomes while the alternating magnetic field is applied, suggesting that the individual magnetosomes remain outside of the eukaryotic cells, yielding a less efficient mechanism of cell destruction.

Magnetosomes are defined as magnetic iron oxide nanoparticles made of magnetite, maghemite or of a composition which is intermediate between maghemite and magnetite. The magnetosomes are also characterized by the presence of a biological membrane, which surrounds them. The presence of amino groups at the surface of the magnetosome membrane enables a coupling with various bioactive macromolecules and yields biocompatibility (Xiang et al., Lett. *Appl. Microbiol.*, 2007, 6, 75-81; Sun et al., *Cancer Lett.*, 2007, 258, 109-117; Sun et al., *Biotech. Bioeng.*, 2008, 101, 1313-1320).

In an embodiment, the magnetosomes belonging to the chain are surrounded by a biological membrane. The magnetosomes may be bound to each other via a biological filament whose structure is only partly known according to A. Komeili, *Ann. Rev. Biochem.* 2007, 76, 351-366.

In one embodiment the magnetosomes are synthesized biologically by magnetotactic bacteria such as *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anerobic magnetotactic spirillum, *Magnetospirillum magneticum* strain MGT-1, and an obligate anaerobe, *Desulfovibrio magneticus* RS-1.

The sizes or mean sizes of the individual magnetosomes contained within the chains of magnetosomes may vary depending in particular on the strain of bacteria, the bacterial growth medium and/or the bacterial growth conditions. Most frequently, the magnetosomes are monodomain nanoparticles (i.e. they possess only one magnetic domain) with sizes lying between about 10 nm and about 120 nm, preferably between 10 nm and 70 nm, most probably between 30 nm and 50 nm. The magnetosome size distribution can vary quite significantly depending on the bacterial strain and bacterial growth conditions. In the AMB-1 species, the majority of the magnetosomes possess sizes lying between 30 nm and 50 nm. Increase in sizes may be obtained when the production of the magnetosomes is carried out in the presence of one or several of the additives such as those described in the invention. The large sizes of the magnetosomes result in ferrimagnetic behaviors at the temperatures reached during the treatment. It also yields a thermally stable magnetic moment. Hence, the movement of the magnetosomes in the organism could potentially be controlled by applying an external magnetic field. Due to their stable magnetic moment, the magnetosomes should produce a better magnetic response than the smaller superparamagnetic iron oxide nanoparticles (SPION) currently used for the medical applications, which possess a thermally unstable magnetic moment. The magnetosomes, which are large monodomain nanoparticles, also possess better heating properties than most chemically synthesized nanoparticles (usually in the form of SPION) when they are suspended in a solution and exposed to an alternating magnetic field.

In one embodiment, the magnetosomes possess a narrow size distribution when the magnetotactic bacteria are grown under optimum conditions.

In one embodiment, a step of size selection can be carried out using either a magnetic field of various intensities (0.05-1 T), a size selection chromatography technique (using for example a column of the type Sephacryl S1000) or a centrifugation technique, which enables to get rid of the smallest magnetosomes remaining in the supernate. Using magnetosomes with sizes lying in a given range can also be helpful in order to introduce them in vesicles of a given size for example.

In a specific embodiment, the method of the present invention uses chains of magnetosomes encapsulated within a vesicle, especially a lipid vesicle. The encapsulation of the chains of magnetosomes yields improved heating properties and also reduces the risks of toxicity by preventing a direct contact between the chains of magnetosomes and the organism. The rotation of the chains of magnetosomes in vivo may be improved by their encapsulation within a lipid vesicle or a similar type of structure.

In one embodiment, the lipid vesicle is a small unilamellar vesicle (SUV, diameter<100 nm), containing a reduced amount of small chains of magnetosomes. Compared with larger vesicle, the SUVs possess several advantages. For example, they are less recognizable by the macrophages (Genc et al., *Langmuir*, 2009, 25, 12604-12613).

In another embodiment, the lipid vesicle is a large unilamellar vesicle (LUV, diameter lying between 100 nm and 1 μm) or a giant unilamellar vesicle (GUV, diameter>1 μm). It is more preferably a LUV for intravenous injection. In the cases of LUV or GUV, the capacity of magnetosome uptake is significantly larger than that of the SUV and hence the heating efficiency is larger.

In one embodiment, the lipid vesicle is a liposome, which is multilamellar.

In one embodiment, the lipid vesicle is composed of a single lipid with a neutral charge such as DOPC (1-Oleoyl-2-palmitoyl-sn-glycero-3-phosphocholine), DMPC (dimyristoylphosphatidylcholine), DPPC (Dipalmitoylphosphatidylcholine), DSPC (1,2-distearoyl-sn-glycero-3-phosphocholine), DMPE (dimyristoyl phosphatidylethanolamine or DPPE (dipalmitoylphosphatidylethanolamine).

In another embodiment, the lipid vesicle is composed of neutral lipids such as those mentioned above mixed with charged lipids such as DOPG (1,2-Dioleoyl-sn-glycero-3-[Phospho-rac-(1-glycerol)]), DPPG (Dipalmitoylphosphatidylglycerol). Lipids with various charges are mixed together in order to optimize the surface charge of the vesicle. Indeed, the latter is an important parameter for the encapsulation of the chains of magnetosomes with the vesicles and for the internalization of the vesicles within the cells (Martina et al., *J. Am. Chem. Soc.*, 2005, 127, 10676; Tai et al., *Nanotechnology*, 2009, 20, 13501).

The method aims at providing in vivo heat therapy, including hyperthermia and thermoablation.

In one embodiment the method described in the present invention shows a way to partially or totally destroy the tumor cells or the tumor by an increase of the temperature in the tumor of less than ~10° C. above the physiological temperature (37° C.), a technique usually called hyperthermia. In a preferred embodiment, the temperature in the tumor reached during hyperthermia lies between about 37°

C. and about 45° C., preferably between about 40° C. and about 45° C., more preferably at about 43° C.

In another embodiment the method of the present invention shows a way to destroy tumor cells or tumor by an increase of the temperature in the tumor of more than ~10° C. above physiological temperature (37° C.), a technique usually called thermoablation. The temperature reached during thermoablation lies between about 45° C. and about 100° C., more preferably between about 45° C. and about 70° C.

In a preferred embodiment, the temperature in the tumor reached during thermoablation lies between about 45° C. and about 55° C., preferably between about 50° C. and about 55° C., most preferably at about 53° C., 54° C. or 55° C.

Since the heat is produced very locally (at the nanometer scale) relatively high temperatures could be reached locally during the treatment.

The temperatures indicated above are temperatures reached within the tumor(s), the tumor tissue and/or their environment. The temperature within the tumor cells (i. e. near the internalized magnetosomes) could be higher.

An object of the present invention is a method for the partial or total destruction of tumor cells or of a tumor. The tumor cells can be killed or lose their ability to multiply indefinitely when the heat treatment described in this invention is applied to them. Since tumor cells are more susceptible to heat than healthy cells (See for example: Overgaard et al., *Cancer*, 1977, 39, 2637-2646), the thermotherapy described in this disclosure could selectively destroy tumor cells.

The method of the present invention describes a heat treatment which induces the partial or total destruction of the tumor cells and/or of the tumor(s). The heat treatment is generated by application of an alternating magnetic field. This magnetic field induces the production of heat by the chains of magnetosomes (encapsulated or not in a vesicle).

In one embodiment, the alternating magnetic field applied during the treatment is characterized by a frequency lying between about 50 kHz and about 1000 kHz, preferably between about 100 kHz and about 500 kHz, more preferably between about 100 kHz and about 200 kHz.

In another embodiment, the magnetic field is characterized by a strength lying between about 0.1 mT and about 200 mT, preferably between about 1 mT and about 100 mT, more preferably between about 10 mT and about 60 mT, typically between about 10 mT and about 50 mT.

The maximum value of the magnetic field strength is determined by the value at which it becomes toxic for the organism (i. e. essentially when it generates Foucault's currents). It may be possible that magnetic fields of strengths higher than 200 mT can be used in the therapy if they are shown to be non toxic.

In another embodiment, the method of the present invention is characterized by the length of time during which the magnetic field is applied. This length of time may be between about 1 second and about 6 hours, preferably between about 1 minute and about 1 hour, preferably between 0.5 and 30 minutes, most preferably between 1 minute and 30 minutes.

The heat treatment is preferably applied to anesthetized patients. Therefore, the time during which the treatment is carried out may be equal or less than the length of time of the anesthesia. A heat treatment can thus potentially be carried out during more than 6 hours, for example if a patient is anesthetized during more than 6 hours.

In another embodiment, the method of the present invention is characterized by the quantity of magnetosomes used during the therapy. This quantity of magnetosomes is related to the quantity of iron oxide contained in the suspension of chains of magnetosomes. This quantity is estimated by measuring the amount of iron oxide present in the suspension of chains of magnetosomes, which is injected. It lies between about 0.001 mg and about 100 mg of iron oxide, preferably between about 0.01 mg and about 100 mg of iron oxide, more preferably between about 0.01 mg and about 10 mg of iron oxide, more preferably between 0.1 and 10 mg of iron oxide, typically between 0.1 and 1 mg of iron oxide. The quantity of magnetosomes, which needs to be injected, essentially depends on the volume of the treated tumor, the temperature required during the treatment and the method of injection. The largest tumor volume and the highest tumor temperature require the largest quantity of magnetosomes administered. Moreover, if the magnetosomes are administered intravenously (or otherwise from the outside of the tumor location(s)), more chains of magnetosomes might be needed than if they are directly administered within or close to the tumor(s).

In another embodiment, the administration of the chains of magnetosomes can be carried out at different speed depending on the targeted tumor(s) and on the concentration of the suspension of chains of magnetosomes administered. For example, administration of the suspension of chains of magnetosomes directly within brain tumor(s) might require a slower speed of injection than intravenous injection or than an injection within a tumor localized at the skin surface. The injection of a more concentrated suspension of chains of magnetosomes might require a slower speed of injection than that of a less concentrated suspension of chain of magnetosomes. The speed of injection preferably lies between 0.1 μl/min and 1 liter/min, more preferably between 1 μl/min and 100 ml/min, most preferably between 1 μl/min and 10 ml/min, where the indicated volume is the volume of the suspension of chains of magnetosomes administered.

In another embodiment, the concentration of the suspension of chains of magnetosomes typically lies between 1 μg/ml and 100 mg/ml, preferably between 10 μg/ml and 50 mg/ml, where this concentration represents the quantity of iron oxide (preferentially maghemite) contained within the suspension. In another embodiment, the chains of magnetosomes are mixed with a solvent, which stabilizes the chains of magnetosomes. The pH of the suspension can be adjusted and/or cations and/or anions can be added to the suspension containing the chains of magnetosomes to stabilize this suspension.

In another embodiment, the administration of the chains of magnetosomes to the patient is repeated. The number of repetition depends on the quantity of magnetosomes, which is administered at once. If only a small quantity of chains of magnetosomes is administered at once, the administration step might be repeated several times until the desired amount of magnetosomes is administered to a patient.

In another embodiment the heat treatment started by application of the alternating magnetic field is repeated. The successive heat treatments applied after administration of a given amount of chains of magnetosome are called a heat cycle. The given amount of magnetosomes used for each heat cycle may have been administered through a single administration or through several successive administrations as explained above. The different heat treatments within a heat cycle are separated one from another by a resting time. The resting time may be equal to 1 second or longer than 1 second, preferably equal to 1 minute or longer than 1 minute, more preferably equal to 10 minutes or longer than 10 minutes, preferably equal to or longer than 30 minutes.

In an embodiment, the different heat treatments within a heat cycle are separated one from another by a longer resting time than that mentioned above. This resting time may lie between 1 day and 15 days.

In an embodiment, the heat cycle is repeated 1 to 648 000 times, in particular 1 to 1000 times, more particularly 1 to 100 times, typically 1 to 10 times. The highest repetition rate of 648 000 times is estimated by assuming that the treatment is carried out for a very short time, typically about one second, during 15 days with a very short resting time, typically about one second resting time separating each treatment. The number of repetition of the treatment depends on the length of time of the treatment. Preferentially the longer the treatment is the less repetition is needed provided the other parameters of the therapy (such as the strength and or frequency of the applied magnetic field) are fixed.

According to the invention, a cession includes the sequences of administering a given amount of chains of magnetosomes to a patient and the generation of heat through application of the magnetic field (as well as other optional sequences as described hereafter). Different cessions may be carried out on the same patient. These cessions may be separated one from another by a length of time, which is sufficiently long. This length of time may be equal to 1 day or longer than 1 day, preferably equal to 15 days or longer than 15 days, more preferably equal to 1 month or longer than 1 month.

In order to optimize the efficiency of the thermotherapy, one needs to adjust the following parameters, i. e. the amount of chains of magnetosomes used during the therapy, the frequency and/or strength of the applied magnetic field, the length of time of the treatment, the number of times that the treatment is repeated during one "cession" and the number of "cessions". These parameters may depend on specific properties of the tumor which is targeted, i. e. for example on its size, its resistance to the thermotherapy and its viscosity. For a tumor with a large volume and/or high resistance in temperature and/or high viscosity, one might consider to increase the amount of magnetosomes injected and/or the strength/frequency of the applied magnetic field and/or the number of repetitions of the treatment. In this case, one might also consider encapsulating the bacterial magnetosomes within a vesicle to favor the production of heat. In an embodiment, the parameters of the thermotherapy are adjusted to optimize the efficiency of the treatment of the tumor to be treated.

In still another embodiment, the values of these parameters also depend on the number of tumors and the presence of metastases, which need to be treated. For a patient in a state of advanced cancer, i. e. with metastasis and/or an important number of tumors, the amount of chains of magnetosomes needed will be higher than for a single tumor. Instead of increasing the quantity of magnetosomes administered, one might also consider to increase the length of time of the treatment, the strength of the magnetic field applied during the treatment (to reach higher temperatures) or the number of times that the treatment is repeated.

The method aims at treating cancers, more preferably solid tumors. Examples of cancers, which can be treated with this type of thermotherapy, include prostate cancer (Kawai et al., *Prostate*, 2008, 68, 784-792), esophageal cancer, pancreatic cancer, breast cancer (Kikumori et al., *Breast Cancer Res. Treat.*, 2009, 113, 435-441), brain cancer (Thiesen et al., *Int. J. Hyperthermia*, 2008, 24, 467-474) and skin cancer (Ito et al., *Cancer Sci.*, 2003, 94, 308-313).

Another object of the invention is a method for the production of chains of magnetosomes wherein magnetotactic bacteria are cultivated in a growth medium containing at least an iron source, such as an iron quinate solution, and additives such as other transition metals than iron and/or chelating agents as defined therein. As an example, the growth medium contains the ingredients mentioned in example 1. These additives produce in specific conditions an increase in the sizes of the magnetosomes and/or in the length of the chains of magnetosomes. They consequently enhance the heating capacity of the chains of magnetosomes when they are exposed to an alternating magnetic field.

In one embodiment, the magnetotactic bacteria are cultivated in a growth medium containing the standard growth medium of magnetotactic bacteria, such as that described in example 1 for the AMB-1 species, and an additive, which is a transition metal, such as for example Cobalt, Nickel, Copper, Zinc, Manganese, Chrome or a mixture of two or more of these metals.

In an embodiment, the doping of the magnetosomes with a transition metal, e.g. cobalt, is carried out by adding about 0.1 µM to about 1 mM, preferably about 1 µM to 100 µM, more preferably about 2 µM to about 20 µM solution of transition metal (e.g. cobalt) within the growth medium of the magnetotactic bacteria. Such solution could be for example a solution of quinate cobalt added to the standard growth medium of the magnetotactic bacteria, e.g. of the AMB-1 species (ATCC 70027), following the same method as that used by Staniland et al (S. Staniland et al., *Nature Nanotech.* 2008, 3, 158-162). The magnetotactic bacteria synthesized in the presence of cobalt, e.g. cobalt quinate, or another transition metal possess improved magnetic properties even when the percentage of cobalt doping is lower than 2% (S. Staniland et al., *Nature Nanotech.*, 2008, 3, 158-162). In the above study by Staniland et al., the change of the magnetic properties in the presence of cobalt was observed for whole magnetotactic bacteria and not for the chains of magnetosomes extracted from the magnetotactic bacteria. The improvement of the magnetic properties of Co-doped magnetosomes arranged in chains and extracted from magnetotactic bacteria, yielding improved heating capability, is a contribution of this invention. For chemically synthesized nanoparticles, a percentage of Co-doping larger than about 10% is usually necessary to observe large changes in the magnetic properties (A. Franco et al., *J. Mag. Mag. Mat.*, 2008, 320, 709-713; R. Tackett et al., *J. Mag. Mag Mat.*, 2008, 320, 2755-2759). This indicates that Co-doped magnetosomes could possess improved heating capacity compared with undoped magnetosomes even for a low percentage of cobalt doping.

In another embodiment, the magnetotactic bacteria are cultivated in the presence of a chelating agent. Without being fully explained by theory, it is thought that the chelating agent binds the cations derived from iron or any one of the other transition metals used as additives, and consequently improves the penetration of iron and/or of another transition metal within the magnetotactic bacteria. This process yields magnetosomes with improved heating properties.

In an embodiment, a suspension containing about 0.02 µM to 1 mM, preferably 0.02 µM to 400 µM, preferably 0.02 to 200 µM, preferably 1 µM to 100 µM, most preferably 2 to 20 µM of an iron chelating agent is added to the growth medium.

In an embodiment, the chelating agent is a molecule, which contains one or several carboxylic acid functional groups such as ALA (alpha lipoic acid), calcein, carboxyfluoresceine, deferasirox, dipicolinic acid, DTPA (Diethylene triamine pentaacetic acid), EDTA (ethylene diamine tetra acetic acid), folic acid or vitamin B9, lactic acid, rhodamine B, carboxymethyl-dextran (polymers), dipicolinic acid or oxalic acid, citric acid or citrate functional groups, such as BAPTA (Aminophenoxyethane-tetraacetic acid), CDTA (cyclohexane-1,2-diaminetetra-acetic acid), EDDH MA (ethylene diamine di-(o-hydroxy-p-methylphenyl) acetic acid), CaNa$_2$-EDTA, EDTCA (ethylene diamine tetra-acetic acid plus Cetavlon, an ammonium surfactant), EDDA (ethylene diamine-N,N'-diacetic acid), EDDHA (ethylenediamine-N,N'-bis(2-hydroxyphenylacetic acid), EGTA (ethylene glycol-bis-(β-amino-ethyl ether) N, N, N', N'-tetra-acetic acid), HEDTA (N-(2-hydroxyethyl)-ethylenediaminetriacetic acid), HEEDTA (Hydroxy-2-ethylenediaminetriacetic Acid), NTA (nitrilotriacetate) or phenolic acid.

In another embodiment, the chelating agent is a molecule, which contains one or several alcohol functional groups, such as catechol or their derivatives or one or several amino-alcohol functional groups, such as dopamine, deferiprone, deferoxamine, desferrioxamine, or one or several amino-carboxylic acid or ketone functional groups, such as doxorubicine, caffeine, D-penicillamine, pyrroloquinoline, HEIDA (hydroxyethylimino-N,N-diethanoic acid).

In one embodiment, the chelating agent is a molecule, which contains a phosphonate or a phosphonic acid functional group, such as AEPN (2-Aminoethylphosphonic acid), AMP (Amino-tris-(methylene-phosphonic acid)), ATMP (Amino tris(methylene phosphonic acid)), CEPA (2-carboxyethyl phosphonic acid), DMMP (Dimethyl methylphosphonate), DTPMP (Diethylenetriamine penta(methylene phosphonic acid)), EDTMP (Ethylenediamine tetra(methylene phosphonic acid)), HEDP (1-Hydroxy Ethylidene-1,1-Diphosphonic Acid), HDTMP (Hexamethylenediamine tetra (methylene phosphonic acid)), HPAA (2-Hydroxyphosphonocarboxylic acid), PBTC (Phosphonobutane-tricarboxylic acid), PMIDA (N-(phosphonomethyl)iminodiacetic acid), TDTMP (Tetramethylenediamine tetra (methylene phosphonic acid)), ADP (adenosinediphosphoric acid) or 1-{12-[4-(dipyrromethenboron difluoride)butanoyl]amino}dodecanoyl-2-hydroxy-sn-glycero-3-phosphate, a sodium salt L-α-phosphatidic acid, a sodium salt 1-palmitoyl-2-(dipyrromethenboron difluoride)undecanoyl-sn-glycero-3-phospho-L-serine).

In another embodiment, the chelating agent is a molecule, which contains a bis, tris or tetra-phosphonate, or a bis, tris or tetra-phosphonic acid functional group, such as a 1-hydroxymethylene-bis-phosphonic acid, propane triphosphonic acid, (nitilotris(methylene))trisphophonic acid, (phosphinylidynetris(methylene)) trisphosphonic acid. Examples of 1-hydroxymethylene-bis-phosphonic acids include alendronic acid (fosamax®), pamidronic acid, zoledronic acid, risedronic acid, neridronic acid, ibandronic acid (bondronat®), minodronic acid and other compounds described in the literature (L. Wilder et al, *J. Med. Chem.*, 2002, 45, 3721-3728; M. Neves, *N. Med. Biol.*, 2002, 29, 329-338; H. Shinoda et al, *Calcif. Tissue Int.*, 1983, 35, 87-89; M. A. Merrel, *Eur. J. Phramacol.*, 2007, 570, 27-37). For 0.4 µM or 4 µM neridronic acid, alendronic acid and residronic acid introduced in the bacterial growth medium, it has been observed herein that the percentage of magnetosomes larger than 45 nm becomes larger than for the magnetosomes synthesized in the absence of bisphosphonic acid. Chains of magnetosomes synthesized in these conditions consequently possess improved heating properties.

In another embodiment, the chelating agent is a molecule, which contains a sulfonate or sulfonic acid functional group or BAL (Dimercaprol) such as BPDS (bathophenanthrolinedisulfonate or 4,7-di(4-phenylsulfonate)-1,10-phenanthroline), DMPS (Dimercapto-propane sulfonate or 2,3-dimercapto-1-propanesulfonic acid), sulforhodamine 101, DMSA (Dimercatptosuccinic acid).

Other examples of chelating agents are polydentate ligands for example hemoglobin, chlorophyll, porphyrin and organic compounds containing pyrolic rings.

In another embodiment, the magnetotactic bacteria are cultivated in a growth medium, which contains both a chelating agent and a transition metal.

In a preferred embodiment, cobalt is used as the transition metal, preferably used in combination with a chelating agent selected from a bisphosphonic acid (neridronic acid, alendronic acid or risedronic acid), rhodamine or EDTA.

The method of treatment of the present invention comprises the following steps of:
(i) providing to a mammal chains of magnetosomes;
(ii) optionally, targeting the chains of magnetosomes in the tissue, the tumor(s) and/or tumor cells to be treated;
(iii) optionally, detecting the chains of magnetosomes in the tissue, tumor(s) or tumor cells to be treated;
(iv) heating by application of an alternating magnetic field;
(v) optionally, removing the chains of magnetosomes from the tissue, tumor(s), tumor cells and/or the body.

In all the following embodiment and preferred embodiment, the chains of magnetosomes can be encapsulated in a vesicle or not.

Steps (iii) and (iv) could also be carried out in any order, for example:
Step (iii) then step (iv); or
Step (iv) then step (iii)
Steps (ii), (iii), and (iv) could be carried out simultaneously or consecutively.
Steps (ii) and (iv) could be carried simultaneously.
Steps (iii) and (iv) could be carried out simultaneously.
By mammal it is intended to mean any mammal also including human.

In an embodiment, the chains of magnetosomes of step (i) could be chains of magnetosomes existing in the body, for example those remaining after a first cycle of treatment.

In another embodiment, step (i) could be preceded by a step (i') of administering the chains of magnetosomes to a mammal.

In an embodiment, step (i') is carried out in such a way that the chains of magnetosomes are administered far from the cells or tissue to be treated. For example, they are injected intravenously in the blood or administered in another organ than that containing the tumor.

In an embodiment, step (i') is carried out in such a way that the chains of magnetosomes are administered close to the cells or tissue to be treated.

In still another embodiment, step (i') is carried out in such a way that the chains of magnetosomes are administered within the cells and/or tumor(s) to be treated.

The distance between the zone of administration of the suspension of chains of magnetosomes and the tumor location can vary depending on whether or not it is possible to inject directly the magnetosomes within the tumor(s). For example, the tumor(s) could be located too close to a vital organ. In this case, a direct injection of the chains of magnetosomes within the tumor(s) would not be possible.

The method of the present invention may also contain a second step of targeting the tumor cells or tumor(s) to be treated. This step is particularly important if the administration of the chains of magnetosomes (encapsulated in a vesicle or not) is not directly carried out within the tumor.

This is often the case when the type of injection chosen is intravenous. The aim of the targeting step is to position the chains of magnetosomes within the environment of the tumor cells and/or of the tumor(s) and/or within the tumor cells and/or tumor(s).

In one embodiment, the step of targeting is carried out by using a magnetic field, which guides the chains of magnetosomes (encapsulated or not in a vesicle) in the environment of the tumor cells and/or of the tumor(s) and/or in the tumor cells and/or tumor(s). This type of targeting is designated as magnetic targeting.

In still another embodiment, two different approaches may be followed to guide the chains of magnetosomes magnetically within the environment of the tumor(s) and/or within the tumor(s) itself. On the one hand, a magnetic field is applied outside of the body of a patient and its orientation is adjusted to enable the chains of magnetosomes to follow the right path until they reach the tumor location. This type of magnetic targeting is designated as an "active" targeting since it may necessitate to change and adjust the characteristics of the magnetic field applied during the targeting step. An adapted MRI instrument in which either the patient or the magnetic field could be orientated in any direction might be used for this targeting step. On the other hand, a magnet could be positioned within or near the tumor location in order to attract the chains of magnetosomes within the tumor and/or the environment of the tumor. In this case, magnetic targeting would essentially be passive (i.e. one would essentially wait for the accumulation of the chains of magnetosomes within the tumor(s) and/or tumor environment).

In another embodiment, the step of targeting the tumor(s) is realized by attaching a biological and/or chemical targeting molecule, which targets the tumor(s), to the chains of magnetosomes or to the vesicle containing the chains of magnetosomes. This targeting molecule is such that it specifically recognizes the tumor cells. This type of targeting is designated as molecular targeting.

In an embodiment, this targeting molecule is an antibody, which specifically recognizes the tumoral cells.

In another embodiment, PEG or folic acid is used as the targeting molecule.

In an embodiment, the coating of the surface of the chains of magnetosomes or that of the vesicle containing the chains of magnetosomes is realized by using poly (ethylene glycol) PEG, and/or folic acid, and/or an antibody. The presence of these molecules may not only enable to target specific cells but also favor intracellular uptake and/or enable to avoid the recognition of the chains of magnetosomes by macrophages (Allen et al, *Trends in Pharmacological Sciences* 1994, 15, 215-220; Blume et al., *Biochim. Biophys. Acta* 1990, 1029, 91-97; Gabizon et al., *Biochim. et Biophys. Acta,* 1992, 1103, 94-100; Zhang et al., *Biomaterials* 2002, 23, 1553-1561).

The step of targeting the tumor(s) could be realized by using a combination of both of the techniques mentioned above
  magnetic targeting;
  molecular targeting; or
  magnetic targeting and molecular targeting.

In an embodiment, the method of detection of the bacterial magnetosomes within the organism (i.e. within the tumor or elsewhere) uses either MRI or another technique such as fluorescence. Such technique is either used to verify that the chains of magnetosomes (encapsulated in a vesicle or not) have reached the site of interest before the treatment induced by heat is started and/or to verify that the chains of magnetosomes are on their way to target the tumor and/or to verify that they are eliminated properly and/or to verify that they have been administered successfully.

In a very interesting embodiment, the magnetic field and especially the magnetic field used for the heating is used to internalize or improve the internalization of the chains of magnetosomes within the tumor cells.

It is also possible, when the chains of magnetosomes are in the tumor or in the tumor cells, to use the magnetic field as a "final approach" to adjust the position of the chains of magnetosomes (encapsulated in a vesicle or not) within the tumor in order to reach maximum heating efficiency and/or anti-tumoral activity during the treatment induced by heat.

In still another embodiment, the chains of magnetosomes (encapsulated in a vesicle or not) are detected by MRI. The detection of whole magnetotactic bacteria by MRI has been demonstrated (R. Benoit et al., *Clin. Cancer. Res.* 2009, 15, 5170-5177). This embodiment concerns the detection of the chains of magnetosomes.

In an embodiment, the chains of magnetosomes are used as contrasts agents, which can easily be detected by MRI due to their specific properties (composition in iron oxide and/or good crystallinity).

In still another embodiment, the chains of magnetosomes are detected using a fluorescence detection technique. In this case, the chains of magnetosomes are modified by the presence of a fluorescent molecule or fluorescent tag, which is positioned at the surface and/or near the surface and/or within one or several of the bacterial magnetosomes belonging to the chains of magnetosomes. Such fluorescent molecule could be rhodamine, calceine, fluorescein, ethidium bromide, green or yellow fluorescent protein, coumarin, cyanine or the derivatives of these listed molecules.

In another embodiment, the fluorescent molecules are positioned within the magnetosomes, at their surface or near their surface by cultivating the magnetotactic bacteria in the presence of these fluorescent molecules. For example, fluorescent magnetosomes are obtained by cultivating the magnetotactic bacteria in the presence of about 0.1 µM to about 1 mM solution of fluorescent molecules. Fluorescent magnetosomes can be obtained, for example by cultivating the magnetotactic bacteria in the presence of about 40 µM to about 400 µM solution of Rhodamine.

In another embodiment, the fluorescent molecules are bound to the chains of magnetosomes. This may be done by chemically attaching the fluorescent molecules to the surface of the magnetosomes.

In still another embodiment, the magnetosomes have fluorescent molecules bound at their surface and contained inside them. This may be obtained by using both of the techniques mentioned above to produce the fluorescent magnetosomes.

In still another embodiment, the vesicle containing the bacterial magnetosomes is made fluorescent by attaching a fluorescent molecule at the surface of the vesicle.

In an embodiment, the fluorescence of the chains of magnetosomes is excited and detected using an excitation/detection scheme, which is such that it positioned outside of the organism. This type of excitation/detection scheme would be used if the tumor is located near the skin surface. For example, an optical fiber could be placed just above the tumor near the skin surface to excite the modified magnetosomes and collect the light emitted by them.

In another embodiment, the excitation and/or detection of the modified magnetosomes is carried out by inserting within the organism a piece of equipment (such as an optical fiber), which reaches the tumor and/or the tumor environment and is able to excite and/or detect the fluorescence of the modified magnetosomes.

In an embodiment, step (v) is a step of removal of the magnetosomes from the tissue, the tumor(s), the tumor cells and/or the body. A technique, which guides the chains of magnetosomes outside of the organism, is used. The bacterial magnetosomes are either directly removed from the tumor(s) (for example chirurgically by making a hole, which provides a path for the bacterial magnetosomes to leave the tumor location and reach the outside of the organism). The bacterial magnetosomes could also be removed from the tumor location and driven towards other organs such as the liver to be eliminated from the body.

In still another embodiment, the technique described in the above embodiment uses a magnetic field which drives the magnetosomes outside of the tumor(s) and of the body.

In still another embodiment, the removal of the chains of magnetosomes from the tumor location is carried out by adjusting the charge surface of the chains of magnetosomes.

In still another embodiment, the chains of magnetosomes are negatively charged.

In an embodiment, the fluorophore is also a chelating agent and is used as an additive during the growth of the magnetotactic bacteria and magnetosome production. In a preferred embodiment, rhodamine is used as chelating agent and fluorophore.

The therapeutic method then contains the heat treatment per se as described above. This method thus enables a localized treatment of tumors and/or tumor cells and minimizes the destruction of healthy cells. Therefore, it provides an improvement compared with chemotherapy or other techniques of cancer treatments, which do not usually specifically target and destroy tumor cells.

In another embodiment, the heat treatment is combined with chemotherapy.

Such a combination of two treatments may be carried out by encapsulating the chains of magnetosomes within a vesicle, preferably a lipid vesicle, in the presence of an active principle, which is an anti-tumoral or anti-cancerous substance. In this case, the lipids forming the vesicles are characterized by a phase transition temperature (the temperature at which the lipids forming the vesicle lose their bi-layer organization) lying between 20° C. and 60° C. The active principle is released in the tumor cells or in the tumors or in the environment of the tumor cells or in the environment of the tumors by heating the chains of magnetosomes and hence the vesicle under the application of an alternating magnetic field.

The vesicles, especially lipid vesicles containing the chains of magnetosomes according to the invention and possibly an active principle according to the invention are also an object of the present invention.

It is also possible to carry out the method of the invention in combination with x-ray and/or radio-therapy and/or chemotherapy and/or a chirurgical operation and/or another type of cancer treatment.

In an embodiment, a chirurgical operation is carried out to partly or totally remove the tumor(s) and/or the environment of the tumor(s). The suspension of chains of magnetosomes is administered within the cavity remaining after the chirurgical operation and the thermotherapy is started by applying an external magnetic field. In this case, the thermotherapy is used either to destroy part of the tumor(s), which could not be removed during the chirurgical operation and/or to prevent the tumor from growing again after the chirurgical operation.

In still another embodiment, a cavity is created during the chirurgical operation within the tumor and/or tumor environment to create a more favourable environment for the production of heat by the chains of magnetosomes than that of the tumor tissue (i. e. for example a less viscous environment), in this embodiment the chains of magnetosomes are administered in this cavity.

The invention is also related to the use of chains of magnetosomes and/or of vesicles containing the chains of magnetosomes, as described above, as a mean of heating, especially of a living tissue or living cells in vivo.

The invention is also related to the use of chains of magnetosomes (encapsulated or not in a vesicle) as a drug, especially as a drug for anti-tumoral treatment, especially for anti-tumoral heat treatment.

In one embodiment the chains of magnetosomes (encapsulated in a vesicle or not) are used as a drug, which enables the treatment of tumor(s) and/or tumor cells through a heating method.

In these uses, the vesicle may contain an active principle, which is for example an anti-tumoral drug.

In one embodiment the vesicles containing the chains of magnetosomes and optionally the active principle are used as a drug, which allows the treatment of the tumor cells or of tumor via a heating method, which induces the release of the active principle.

In another embodiment, the chains of magnetosomes (encapsulated in a vesicle or not) are used as a drug activated by a medical device, which is the alternating magnetic field.

The invention also relates to the use of chains of magnetosomes and/or vesicles containing chains of magnetosomes and optionally an active principle as a medical device, specifically designed for the treatment of tumor(s) and/or tumor cells.

In one embodiment the chains of magnetosomes (encapsulated in a vesicle or not) are used as a medical device, which enables a magnetic treatment of either tumors or tumor cells.

In one embodiment the chains of magnetosomes (encapsulated in a vesicle or not) are used as a medical device, which enables heating of either the tumors or tumor cells or their environment.

In one embodiment the chains of magnetosomes or the vesicle containing the chains of magnetosomes are combined with an active principle and used as a medical device, which allows the delivery of an active principle within the tumors, the tumor cells or their environment.

According to a feature, use is made of a device used to induce a magnetic excitation of the chains of magnetosomes to complete the medical device.

The invention is also related to a kit containing chains of magnetosomes (encapsulated in a vesicle or not) and a device, which is able to generate a magnetic field with the features required for a treatment of cancer or tumors induced by heat.

In one embodiment, the vesicles belonging to the kit are used in combination with an active principle, which is encapsulated within the vesicles.

The invention will now be described in further details using the following non-limiting examples.

DESCRIPTION OF THE EXAMPLES

Example 1

Figure 1:
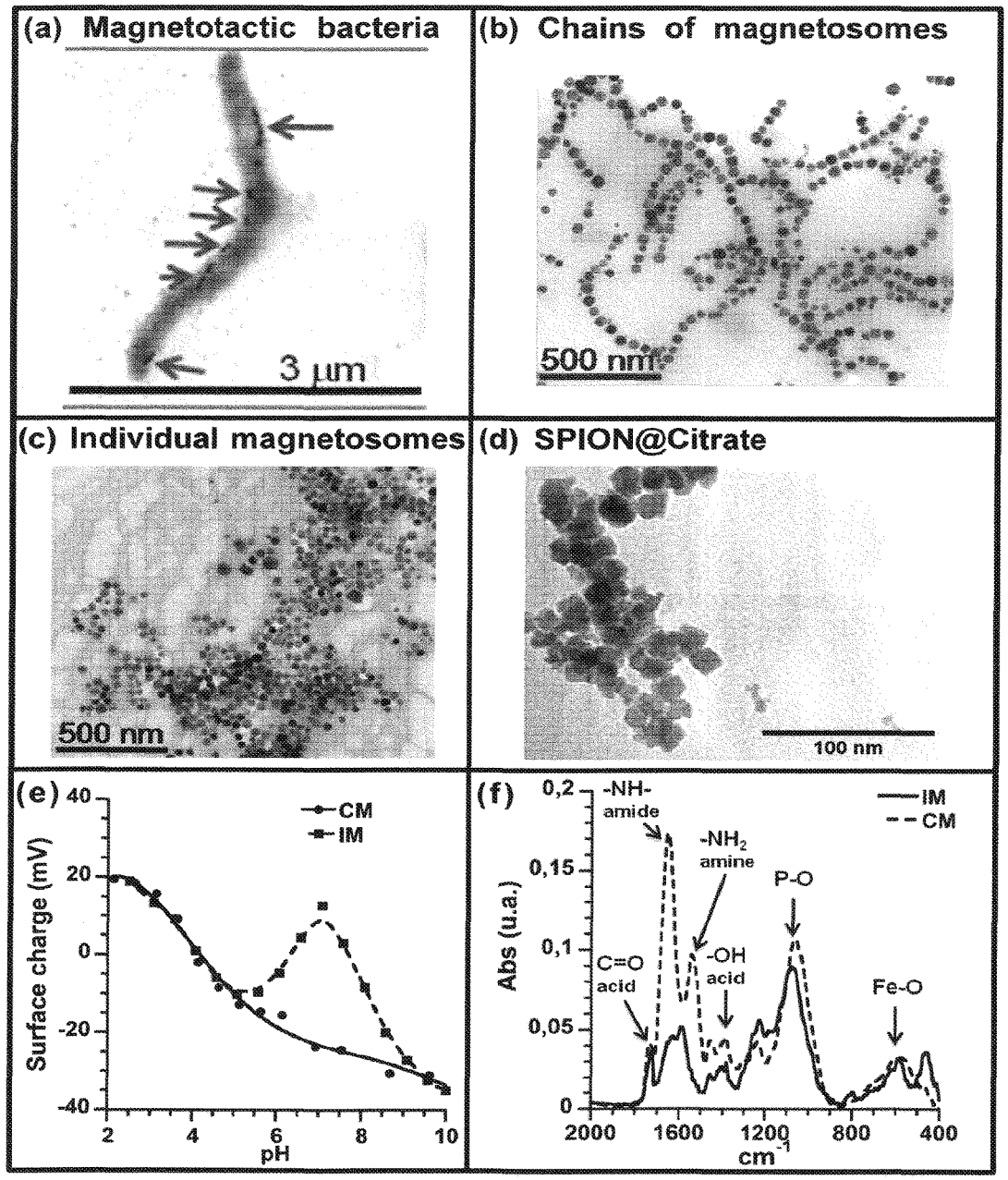
FIG. 1: (a) Transmission electron microscopy (TEM) micrograph of one cell of *Magnetospirillum magneticum* strain AMB-1, where the arrows indicate the localization of the chains of magnetosomes; (b) TEM micrograph of the chains of magnetosomes extracted from the bacteria; (c) TEM micrograph of individual magnetosomes detached from the chains; (d) TEM micrograph of the chemically synthesized nanoparticles (SPION@Citrate); (e) A measurement of charge at the surface of the chains of magnetosomes (CM) and individual magnetosomes (IM) as a function of the pH of the suspension containing these two types of bacterial magnetosomes; (f) The infrared spectra of the chains of magnetosomes (CM) and individual magnetosomes (IM).

Preparation of the Different Types of Particles Used as Heating Sources:

In this example, we describe the methods following which the different types of particles used as heating sources were prepared. These particles are particles contained within whole magnetotactic bacteria, chains of magnetosomes extracted from the magnetotactic bacteria, individual magnetosomes extracted from magnetotactic bacteria and detached from the chains by heat and SDS treatment, chemically synthesized superparamagnetic iron oxide nanoparticles covered by citrate ions (SPION@Citrate) or commercially available chemically synthesized nanoparticles covered by PEG molecules (SPION@PEG). The SPION@PEG were purchased from the German company Micromod (Product name: Nanomag®-D-spio, Product Number: 79-00-201).

The SPION@Citrate were used as standard nanoparticles, because they possess similar sizes than most nanoparticles used for magnetic hyperthermia (See for example: Johannsen et al, *European Urology* 2007, 52, 1653-1662 or the other references listed at the beginning of this pattern application) and a chemical coating, which stabilizes the nanoparticles but should not produce any anti-tumoral activity.

The SPION@PEG were also used as standard nanoparticles since they are commercially available and are the same as those used by DeNardo's group to carry out magnetic hyperthermia (See for example: De Nardo et al, *Clin. Cancer Res.* 2005, 11, 7087s-7092s). The efficiency of the chains of magnetosomes in the thermotherapy was compared with that of these two standards (SPION@Citrate and SPION@PEG).

*Magnetospirillum magneticum* strain AMB-1 was purchased from the ATCC (ATCC 700274). Cells were grown micro-anaerobically at room temperature (~25° C.) in liquid culture in slightly modified revised MSGM medium (ATCC Medium 1653). In one litter, this growth medium contains 0.68 g of monobasic potassium phosphate, 0.85 g of sodium succinate, 0.57 g of sodium tartrate, 0.083 g of sodium acetate, 225 µl of 0.2% resazurin, 0.17 g of sodium nitrate, 0.04 g of L-ascorbic acid, 2 ml of a 10 mM iron quinate solution, 10 ml of Woolf's vitamins and 5 ml of Woolf's minerals. The iron quinate solution was prepared by dissolving 0.19 g of quinic acid and 0.29 g of $FeCl_3.6H_2O$ in 100 milliliter of distilled water. The solution of Woolf's minerals contained in 1 liter of distilled water 0.5 g of Nitrilotriacetic acid (NTA, $C_6H_9NO_6$), 1.5 g of Magnesium Sulfate HEPTA ($MgSO_4.7H_2O$), 1 g of Sodium Chloride, 0.5 g of manganese sulfate ($MnSO_4.H_2O$), 100 mg of ferrous sulfate heptahydrate ($FeSO_4.7H_2O$), 100 mg of cobalt nitrate ($CO(NO_3)_2.7H_2O$), 100 mg of calcium chloride ($CaCl_2$), 100 mg of Zinc sulfate heptahydrate ($ZnSO_4.7H_2O$), 10 mg of hydrate copper sulfate ($CuSO_4.5H_2O$), 10 mg of aluminium potassium sulfate dodecahydrate ($AlK(SO_4).12H_2O$), 10 mg of boric acid ($H_3BO_3$), 10 mg of sodium molybdate ($Na_2MoO_4.2H_2O$), 2 mg of sodium selenite ($Na_2SeO_3$), 10 mg of sodium tungstate dihydrate ($Na_2WO_4.2H_2O$) and 20 mg of Nickel chloride ($NiCl_2.6H_2O$). The solution of Woolf's vitamins was prepared by dissolving in 1 liter of distilled water 2.2 mg of folic acid (vitamin B9), 10.2 mg of pyridoxine (vitamin B6), 5.2 mg of Riboflavin (vitamin B2), 2.2 mg of Biotin (vitamin H or B7), 5.2 mg of thiamin (vitamin B1), 5.2 mg of nicotinic acid (vitamin B3 or PP), 5.2 mg of pantothenic acid (vitamin B5), 0.4 mg of vitamin B12, 5.2 mg of amino benzoic acid, 5.2 mg of thiotic acid and 900 mg of potassium phosphate. The pH of the growth medium was adjusted to 6.85 using a 5M sodium hydroxide solution. Cells were harvested as described below at stationary phase. Stationary phase occurred when the medium became completely reduced as indicated by a change in the coloration of the growth medium, from pink to colorless.

Three different types of samples were prepared from intact whole cells of *M. magneticum*. Cells were harvested at stationary phase by centrifugation at 8,000 rpm for 15 min. The supernatant (spent growth medium) was discarded and cells were resuspended in 3 ml of deionized water. For suspensions of whole intact cells, this sample was not treated further. The TEM micrograph of FIG. 1(*a*) shows one typical AMB-1 magnetotactic bacterium containing several chains of magnetosomes.

To extract the chains of magnetosomes, 1 ml of the cell suspension was recentrifuged and resuspended in 10 mM Tris.HCl buffer (pH 7.4) and then sonicated for 120 min at 30 W to lyse the cells releasing the chains of magnetosomes. Sonication times of 60 and 180 min were also tested and enabled to extract the chains of magnetosomes from the bacteria. For a sonication time of less than 60 min, the magnetotactic bacteria were not all lysed while for a sonication time of more than 180 min, aggregation began to be observed due to the presence of individual aggregated magnetosomes.

After sonication, the suspension of chains of magnetosomes was magnetically separated by placing a strong magnet in neodymium (0.1-1 T) next to the tube where the magnetic material was collected as a pellet. The supernate containing cells debris and other organic material was removed. The magnetosome chains were washed 10 times with a 10 mM Tris.HCl buffer (pH 7.4) in this way and were finally resuspended in sterile deionized water. A typical assembly of chains of magnetosomes extracted from the whole bacteria is shown in the TEM micrograph of FIG. 1(*b*). The surface charge of the chains of magnetosome was measured as a function of pH using dynamic light scattering measurements (NanoZetasizer, Malvern instruments Ltd). At physiological pH, FIG. 1(*e*) shows that the surface charge of the chains of magnetosomes is negative at −22 mV. The infrared measurements were carried out using a Nicolet 380 FT IR Thermo Electro. The infra-red absorption spectrum of a suspension of chains of magnetosomes was also recorded. It showed peaks arising from the functional groups carboxylic acid, amine, amide, phosphate (P—O), revealing the presence of both proteins and phospholipids within the suspension of chains of magnetosomes. This result suggests that both the membrane surrounding the magnetosomes and the filament binding the magnetosomes together are present in this sample (D. Faivre et al, *Chem. Rev.*, 2008, 108, 4875-4898).

Individual magnetosomes (i.e. magnetosomes, which are not organized in chains) were obtained by heating the suspension of magnetosome chains for five hours at 90° C. in the presence of 1% sodium dodecyl sulfate (SDS) in deionized water to remove most of the biological material surrounding the magnetosomes, i. e. most of the magnetosome membrane surrounding the magnetosomes and the cytoskeleton responsible for the alignment of the magnetosomes in each chain (D. Faivre, *Chem. Rev.*, 2008, 108, 4875-4898). Individual magnetosomes were washed as described for magnetosome chains and resuspended in deionized water. The TEM micrograph of FIG. 1(*c*) shows a typical assembly of individual magnetosomes. The individual magnetosomes possess different properties from the chains of magnetosomes. They form an aggregated assembly of nanoparticules (FIG. 1(c)). They possess a surface charge, which strongly depends on their level of aggregation. When the individual magnetosomes are sonicated and dispersed in water, they possess a relatively similar surface charge than the chains of magnetosomes at pH 7. However, when they are aggregated, the individual magnetosomes possess a positive charge (10 mV at pH 7, FIG. 1(e)). The individual magnetosomes are surrounded by phospholipid acid (presence of P-0 peak in the infra-red absorption spectrum of FIG. 1(f)), but not by proteins (absence of amide in the infra-red absorption spectrum of FIG. 1(f)), suggesting that the biomaterial, which surrounds the magnetosomes has not been completely removed but has been sufficiently denatured to yield individual magnetosomes not organized in chains.

The chemically synthesized nanoparticles (SPION@Citrate) were prepared following a protocol described previously (Lalatonne et al., *Phys. Rev. E*, 2005, 71, 011404-1, 011404-10). To prepare non-coated $\gamma Fe_2O_3$ particles, a solution of base (dimethylamine) was first added to an aqueous micellar solution of ferrous dodecyl sulfate $(Fe(DS)_2)$ and mixed. The final reactant concentrations were $1.3 \times 10^{-2}$ mol $L^{-1}$ and $8.5 \times 10^{-1}$ mol $L^{-1}$ for $Fe(DS)_2$ and dimethylamine, respectively. The solution was then stirred vigorously for 2 hours at 28.5° C. and the resulting precipitate of uncoated nanocrystals was isolated from the supernatant by centrifugation. In the second step, the precipitate was washed with an acidic solution ($HNO_3$, $10^{-2}$ mol·$L^{-1}$) until a solution of pH=2 were reached. Sodium citrate dissolved in water ($[Na_3C_6O_7H_5]=1.5 \times 10^{-2}$ mol $L^{-1}$) was used to coat the nanoparticles. The solution was subjected to sonication for 2 hours at 90° C. and the addition of acetone induced nanocrystal precipitation. After washing with a large excess of acetone, the precipitate was dried in air. The nanocrystals coated with citrate ions were finally dispersed in water. The pH, which was initially ~2, was progressively increased up to 7.4 by adding of solution of sodium hydroxide NaOH ($10^{-1}$ mol·$L^{-1}$). The SPION@Citrate are composed of maghemite and possess a mean size of ~10 nm. A TEM micrograph of the SPION@Citrate is shown in FIG. 1(d).

The detailed properties of the SPION@PEG can be obtained from the company Micromod. It is indicated in the information sheet (product-No: 79-00-201) provided by Micromod that the SPION@PEG possess a saturating magnetization of 34 emu/g, a size of about 20 nm, a polydispersity of less than 20% and that they are stable in aqueous buffer for pH>4.

Example 2

Heat Production by Bacterial Magnetosomes Exposed to an Oscillating Magnetic Field.

In this example, we provide a detailed study of the mechanisms of heat production by magnetosomes biomineralized by magnetotactic bacteria. The values of the magnetic field frequency (108 kHz) and magnetic field amplitude (23 to 88 mT) used to heat the different samples lie within the range of the magnetic field parameters used to carry out high frequency high amplitude AMF (alternating magnetic field) hyperthermia (Ivkov et al, *Clin. Cancer Res.*, 2005, 11, 7093s-7103s; De Nardo et al, *Clin. Cancer Res.*, 2005, 11, 7087s-7092s; De Nardo et al, *The J. Nucl. Med.*, 2007, 48, 437-444). For AMF hyperthermia, recommended magnetic field frequencies lie between 50 kHz and 1 MHz while the magnetic field amplitude needs to remain below 100 mT (Mornet et al, *J. Mater. Chem.*, 2004, 14, 2161-2175). We compare the heat-producing properties of three different types of magnetosome arrangements (Alphandéry et al, *J. Phys. Chem. C*, 2008, 112, 12304-12309; Alphandéry et al, *ACS Nano*, 2009, 3, 1539-1547): 1) magnetosome chains contained within intact AMB-1 magnetotactic bacteria; 2) chains of magnetosomes extracted from the bacteria that retained their magnetosome membranes; and 3) individual magnetosome crystals whose magnetosome membranes have been mostly removed.

It is known that, for large ferromagnetic nanoparticles, there are two main heat-producing mechanisms. The first one is due to the physical rotation of magnetic nanoparticles in a magnetic field and the second one is a result of hysteresis losses (Hergt et al, *IEEE Trans. Mag.*, 1998, 34, 3745-3754). In order to determine which of these mechanisms is responsible for heat production by the three different types of magnetosome arrangements mentioned above, we compared the heating rates of the samples in water, in which rotation of the cells and magnetosomes is possible, with those present in a gel, where rotation is inhibited. In this way, the amount of heat generated by the rotation of the bacteria or magnetosomes and that arising from hysteresis losses can be determined. In order to verify that heat produced in the gel is due to hysteresis losses, we measured hysteresis losses independently using magnetic measurements.

Materials and Methods:

Samples were examined using a JEOL model JEM 1011 transmission electron microscope (JEOL Ltd., Tokyo) operating at 100 kV. Five microliters of a solution containing $2 \times 10^{-4}$% in weight of magnetosomes were deposited on a carbon-coated copper grid and the grids were allowed to dry before examination. The same relative quantity of magnetosomes were used to prepare all samples, thus aggregation in a particular sample was not a result from a difference in the concentration of the magnetosomes.

Magnetic measurements were carried out using a vibrating sample magnetometer (VSM, Quantum design, San Diego, Calif.). For magnetic measurements, 25 microliters of a liquid suspension of magnetotactic bacterial cells, chains of magnetosomes or individual magnetosomes containing $2.10^{-3}$% in weight of magnetosomes, were deposited on top of a silica substrate. The samples were then positioned inside a capsule made of hard gelatin in a direction parallel to that of the magnetic field. Three types of magnetic measurements were performed, those of the saturating isothermal remanent magnetization (SIRM) and major or minor hysteresis loops. SIRM measurements were used to determine the composition of the magnetosomes following a method similar to that previously described (Alphandéry et al., *J. Phys. Chem. C*, 2008, 112, 12304-12309) and showed that the magnetite in the magnetosomes had been almost completely oxidized to maghemite. This result was not unexpected as our suspensions of magnetic material were not freshly prepared and magnetite in magnetosomes has been known to oxidize to maghemite over time (Chen et al., *Earth Planet. Sci. Lett.*, 2005, 240, 790-802). Maghemite and magnetite have very similar magnetic properties at room temperature (Alphandéry et al., *J. Phys. Chem. C*, 2008, 112, 12304-12309). The fact that the magnetosomes magnetite had transformed to maghemite does not substantially change the conclusions drawn in this pattern since maghemite and magnetite have very similar magnetic properties at room temperature (Alphandéry et al., *J. Phys. Chem. C*, 2008, 112, 12304-12309). Major hysteresis loop measurements were carried out at 300 K in order to determine the amount of maghemite contained within samples. The latter is determined by dividing the saturating magnetization of the samples by the saturating magnetization of maghemite. For nanoparticles as large as the magnetosome crystals, the saturating magnetization is that of the bulk material (in this case bulk maghemite). Finally, measurements of minor hysteresis loops were also carried out by recording the magnetization of the samples as a function of a continuous magnetic field, which is applied between —$H_0$ and $H_0$ where $H_0$ is 23 mT, 36 mT, 66 mT or 88 mT.

These experiments were carried out with the whole bacteria, chains of magnetosomes and individual magnetosomes either suspended in ultrapure deionized water (18.6 MΩ) or in aqueous agarose gel (2% by weight). The concentration of maghemite was 457 µg ml$^{-1}$ for the liquid suspension containing the whole cells, 435 µg ml$^{-1}$ for that containing the chains of magnetosomes and 380 µg ml$^{-1}$ for that containing the individual magnetosomes. 250 µl of each of these three suspensions were poured inside polypropylene tubes and positioned at the center of a coil producing an oscillating magnetic field of frequency 108 kHz, the field amplitude being fixed at 23 mT, 36 mT, 66 mT or 88 mT. In order to generate the alternating current, the coil was connected to a generator (Celes inductor C97104) and the temperature was measured using an optical fiber probe (Luxtron STF-2, BFi OPTiLAS SAS).

Results and Discussions:

FIG. 1(a) depicts a transmission electron micrograph (TEM) of cells of Magnetospirillum magneticum strain AMB-1 showing typical chains of magnetosomes. The volume occupied by magnetosomes in a whole cell is rather small, typically ~0.02%. An aqueous suspension containing intact whole cells of M. magneticum was subjected to an oscillating magnetic field of frequency ν=108 kHz and field amplitudes of $H_0$=23 mT and $H_0$=88 mT. The heating rates of cells suspended in liquid increased when the magnetic field strength was increased from 23 mT to 88 mT (FIGS. 2(a) and 2(b)). From the slopes of the variations with time of the temperature measured at 22° C. (ΔT/δT), we estimated the SAR of the intact cells suspended in liquid using the Equation 1 below (Mornet et al., J. Mater. Chem., 2004, 14, 2161-2175; Hergt et al., J. Magn. Magn. Matter., 2005, 293, 80-86):

$$SAR = C_{water}\left(\frac{\Delta T}{\delta t}\right)\frac{1}{x_m} \quad (1)$$

where $C_{water}$ is the specific heat capacity of water ($C_{water}$=4.184 J/g·K) and $x_m$ is the concentration of iron in g per ml of solvent (water). Using the above formula, we deduced that the SAR of the whole bacterial suspension increased from 108±32 W/$g_{Fe}$ to 864±130 W/$g_{Fe}$ when the magnetic field amplitude was increased from 23 mT to 88 mT. In order to determine if the amount of heat (SAR) generated by the whole magnetotactic bacteria arises from the rotation of the whole bacteria, from hysteresis losses or from both of these mechanisms, we measured the areas of the minor hysteresis loops of the whole intact cells (FIG. 2(c)), which provide estimates of the hysteresis losses of the whole cells. Using the method of Hergt et al (Hergt et al., J. Magn. Magn. Matter., 2005, 293, 80-86) we deduced from the areas of the minor hysteresis loops shown in FIG. 2(c) that the hysteresis losses of the intact cells increased from 54±25 W/$g_{Fe}$ at 23 mT to 810±121 W/$g_{Fe}$ at 88 mT. These SAR values are similar to those measured for the bacterial cells in suspension (FIG. (2d)). Unexpectedly, the SAR determined for cells fixed in agarose gel, was significantly smaller than the areas of the minor hysteresis loops and did not seem to provide good estimates of hysteresis losses (FIG. 2(d)). This might be due to loss of some of the bacterial cells during the preparation of the gel yielding a lower concentration of magnetosomes than in the other samples. From these results, we conclude that the rotation of intact bacterial cells does not contribute to the production of heat in this case. Due to their large weight and volume, intact cells of M. magneticum are not able to rotate sufficiently well under the application of an external magnetic field to generate heat. The absence of contribution of the rotation can be confirmed by estimating the SAR due to the rotation of the bacterial cells, $SAR_{rot}$. The latter is estimated using Equation 2 below (Hergt et al., IEEE Trans. Mag. 1998, 34, 3745-3754).

$$SAR_{rot} = \frac{1}{2}\frac{(M_s H_o V)^2}{K_b T}\frac{1}{\rho V}\frac{1}{\tau_b}\frac{(\omega \tau_b)^2}{1+(\omega \tau_b)^2} \quad (2)$$

In (2), we have assumed that the Brownian relaxation time, $\tau_b$, is much smaller than the Néel relaxation time $\tau_n$, where $\tau_b$=3 η$V/K_b T$ and $\tau_n$=$\tau_0$ exp($E_a/K_b T$). For the different samples, $\tau_b$ lies between 2.5 10$^{-5}$ sec. and 0.3 sec (Mornet et al, J. Mater. Chem., 2004, 14, 2161-2175. Given that $\tau_0$~10$^{-3}$ sec and the ratio between the anisotropy energy of a chain of magnetosomes and the thermal energy, $E_a/K_b T$~480 (Alphandéry et al., ACS Nano 2009, 3, 1539-1547), we find that $\tau_n$~3. 10$^{38}$ sec. and hence $\tau_b/\tau_n$<<1. This justifies the use of (2) to measure the SAR. In Equation 2, ω=2 πf where f=108 kHz is the frequency of the oscillating magnetic field, $M_s$ is the saturating magnetization of maghemite ($M_s$=390 emu/cm$^3$), $H_0$ is the amplitude of the applied magnetic field (23 mT<$H_0$<88 mT), V~20 10$^{-17}$ cm$^3$ is the volume of a typical chain of magnetosomes (Alphandéry et al., J. Phys. Chem. C, 2008, 112, 12304-12309), ρ~5 g/cm$^3$ is the specific weight of maghemite, $K_b$~1.38 10$^{-23}$ J/K is the Boltzmann constant and $\pi_b$~10 sec is the Brownian relaxation time of an intact bacterial cell in water. The Brownian relaxation times are estimated using the formula $\tau_b$=3 η$V_h/K_b T$, where $V_h$ is the hydrodynamic volume. For the whole magnetotactic bacteria, we consider that $V_h$=4/3 πr$^3$, where r is half the typical length of a bacterium (1.5 µm). Using these values, we find that $SAR_{rot}$ lies between 5.10$^{-2}$ W/$g_{Fe}$ and 7.10$^{-1}$ W/$g_{Fe}$ for $H_0$ values between 23 and 88 mT. These values are much smaller than the measured SAR due to hysteresis losses, which are ~82±58 W/$g_{Fe}$ at 23 mT and ~841±153 W/$g_{Fe}$ at 88 mT (FIG. 2(d)), where these values are averages between the SAR deduced from the heating rate in solution and those deduced from the measurements of the minor hysteresis loops. Thus, rotation of the whole bacterial cells does not appear to contribute to the observed increase in temperature. As indicated in FIG. 2(d), the SAR appears to be completely due to hysteresis losses. These losses become much more significant at higher magnetic field amplitudes (SAR~841±153 W/$g_{Fe}$ at 88 mT) than at 23 mT (SAR~82±58 W/$g_{Fe}$)). This finding, increased hysteresis losses with increasing magnetic field amplitude, has been previously observed for chemically-synthesized magnetite nanoparticles (Hergt et al., IEEE Trans. Mag., 1998, 34, 3745-3754). The SAR per cycle of the whole cells in suspension, which is defined as the SAR divided by the frequency of the oscillating magnetic field, lies between 0.7±0.5 J/kg$_{Fe}$ and 7.8±1.4 J/kg$_{Fe}$. These values are higher than most of those obtained with chemically-synthesized magnetic nanoparticles, which typically lie between 0.001 J/kg$_{Fe}$ and 1.2 J/kg$_{Fe}$ for a wide range of magnetic nanoparticle sizes and compositions as well as for a large choice of magnetic field frequencies and amplitudes (Dutz et al, *J. Magn. Magn. Mater.*, 2007, 308, 305-312; Ma et al., *J. Magn. Magn. Mater.*, 2004, 268, 33-39; Jordan et al., *J. Nano. Res.*, 2003, 5, 597-600; Brusentsov et al., *J. Magn. Magn. Mater.*, 2001, 225, 113-117; Chan et al., *Scientific and clinical applications of magnetic carriers*, Häfeli et al. (eds.), Plenum Pres, NY, 1997, 607-618). We conclude that the suspensions of whole magnetotactic bacteria produce a larger amount of heat than most of the chemically-synthesized magnetic nanoparticles under our experimental conditions.

Figure 2:
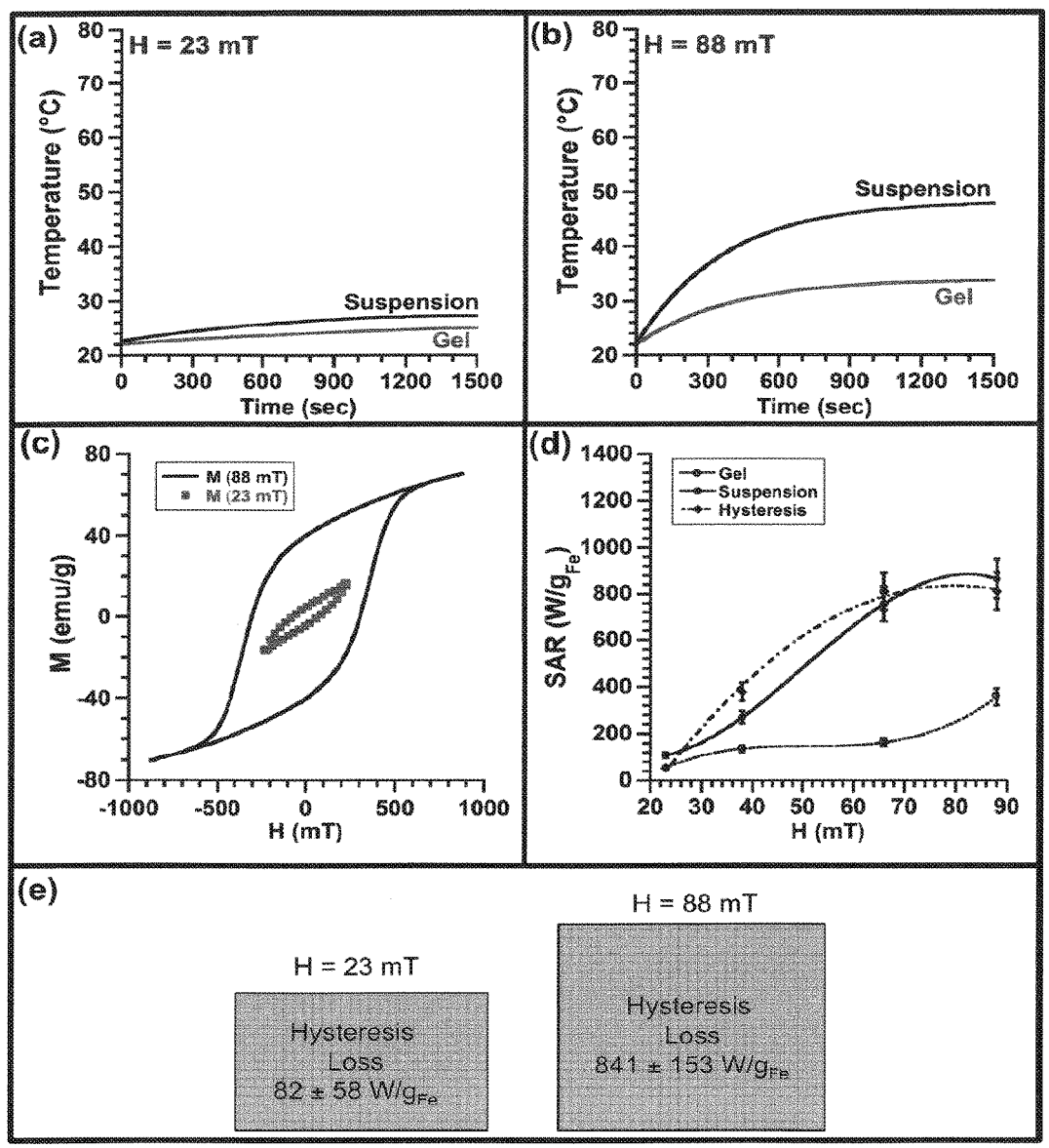
FIG. 2: (a) Variation of the temperature of a suspension of intact magnetotactic bacterial cells as a function of time when the suspension is subjected to an alternating magnetic field (AMF) of frequency 108 kHz and AMF amplitude of 23 mT. The lines correspond to the suspension of cells in water (suspension) and in a 2% agarose gel (gel), respectively; (b) Same as in (a) for an AMF amplitude of 88 mT; (c) Minor hysteresis loops of the whole bacteria measured at 23 mT (squares) or 88 mT (hysteresis); (d) Specific absorption rate (SAR) of a suspension of magnetotactic bacteria contained either in water, or in a gel, as a function of AMF amplitude. The hysteresis losses measured from the area of the minor hysteresis loops of a suspension of magnetotactic bacteria contained in a gel; (e): Plots in column bars of the SAR of the intact cells measured at 23 mT and 88 mT. The boxes represent the contribution to the observed increases in temperature due to hysteresis losses.
Figure 3:
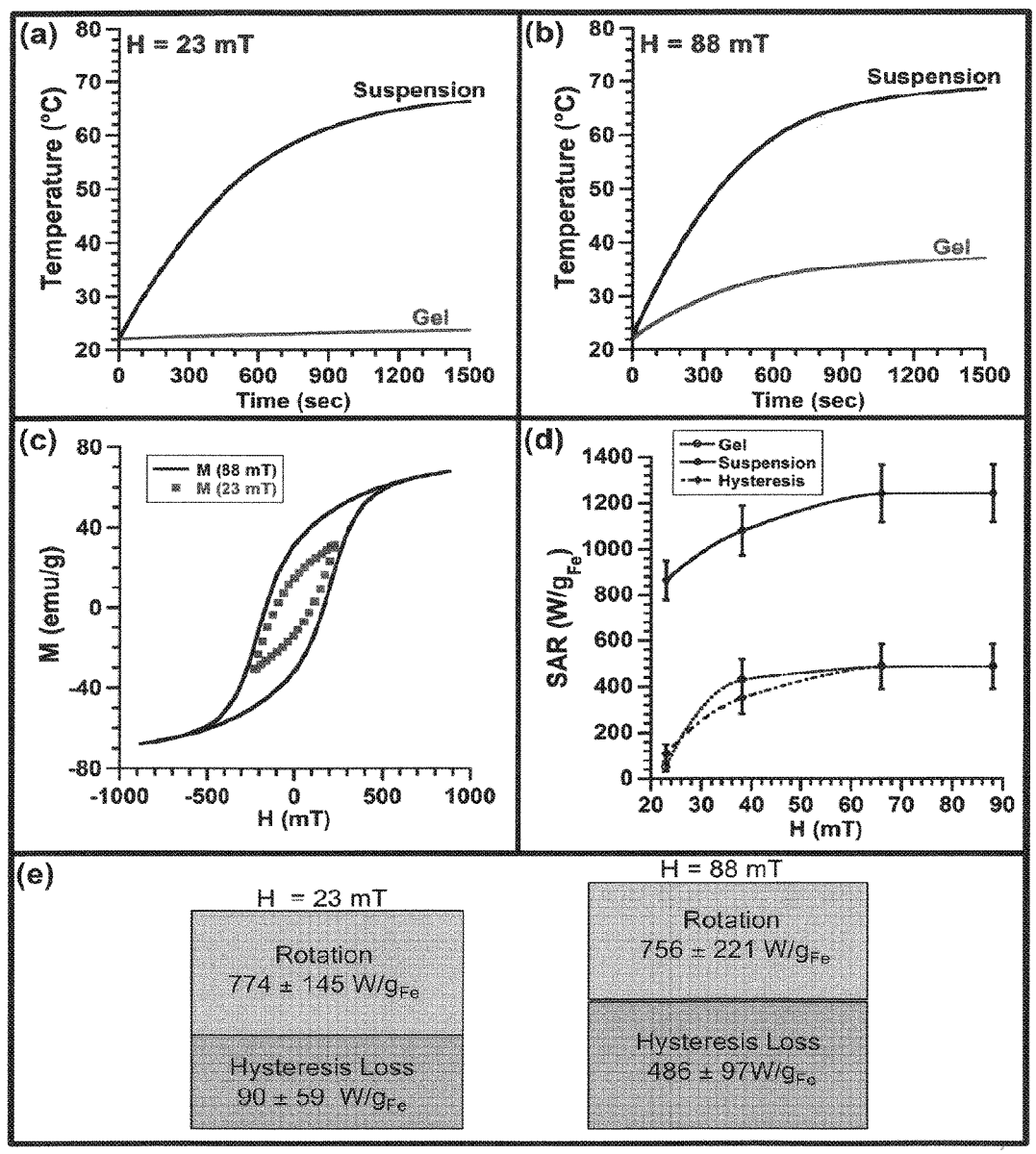
FIG. 3: Properties of the chains of magnetosomes extracted from cells of *Magnetospirillum magneticum* strain AMB-1. (a) Increase in temperature of the chains of magnetosomes as a function of time in the presence of an AMF of frequency 108 kHz and AMF amplitude 23 mT. The lines indicate the heating rate of to the chains of magnetosomes suspended in water (solution) or in a 2% agarose gel (gel) respectively; (b) Same as in (a) for a AMF amplitude of 88 mT; (c) Minor hysteresis loops of chains of magnetosomes at 23 mT (square) and 88 mT (line); (d) SAR measured from the slope at 22° C. of the heating rate of the chains of magnetosomes suspended in water (suspension), or in a gel (gel), as a function of the AMF amplitude. Hysteresis losses measured from the area of the minor hysteresis loops of a suspension of chains of magnetosomes contained in a gel (hysteresis). (e): Plots in column bars of the SAR of the chains of magnetosomes measured at 23 mT and 88 mT. Boxes represent the contribution to the observed increases in temperature resulting from hysteresis losses and rotation of the chains of magnetosomes, respectively.

Chains of magnetosomes were extracted from bacterial cells to presumably enhance their rotation in the magnetic field without the cell structure interfering with rotation. To verify that the magnetosomes were actually extracted from the bacteria and that they remain as chains, we used electron microscopy. FIG. 1(*b*) shows typical assemblies of chains of magnetosomes (Alphandéry et al., *ACS Nano.*, 2009, 3, 1539-1547; Alphandéry et al., *J. Phys. Chem. C*, 2008, 112, 12304-12309), which do not aggregate into clumps but are sufficiently close one to another as chains to be interacting magnetically. Heat production rates of the chains of magnetosomes are shown in FIGS. 3(*a*) and 3(*b*) for the magnetic field amplitudes of 23 mT and 88 mT, respectively. In solution, they are characterized by a ~43° C. increase over a time period of 1500 sec. at 23 mT (FIG. 3(*a*)) and by a ~48° C. increase over the same time period at 88 mT (FIG. 3(*b*)). These heating rates are between about 2 and about 10 times larger than those obtained with the whole cells (FIGS. 2(*a*), 2(*b*), 4(*a*) and 4(*b*)). This suggests either that the chains of magnetosomes produce larger hysteresis losses than intact bacteria cells or that their rotation in the oscillating magnetic field contributes to heat production or both. In order to discern which, if any, of these explanations is responsible for the greater heat production rates, hysteresis losses of the chains of magnetosomes were determined. FIG. 3(*c*) shows the minor hysteresis loops of the chains at 23 mT and 88 mT. The areas of the minor hysteresis loops for the chains of magnetosome were less than those obtained with the intact bacteria cells (FIG. 2(*c*)). This decrease is likely due to magnetic interactions between the chains of magnetosomes (Alphandéry et al., *J. Phys. Chem. C*, 2008, 112, 12304-12309) and thus we conclude that the higher heat production rate observed for the chains of magnetosomes compared to the intact bacterial cells suspended in liquid is not due to an increase of hysteresis losses but to the rotation of the chains. The contribution of the rotation to heat production by the chains of magnetosomes can be further confirmed by estimating the SAR of the chains of magnetosomes suspended in liquid. Using equation (1) and the values of $\Delta T/\delta T$ for the chains of magnetosomes in suspension (FIGS. 3(*a*) and 3(*b*)), we find that the SAR increases from ~864±86 W/g$_{Fe}$ at 23 mT to ~1242±124 W/g$_{Fe}$ at 88 mT (FIG. 3(*d*)). These SAR values are larger than the hysteresis losses deduced either from the SAR of the chains of magnetosomes in the gel (SAR~54±22 W/g$_{Fe}$ at 23 mT and SAR~487±97 W/g$_{Fe}$ at 88 mT) or from the areas of the minor hysteresis loops (SAR~108±41 W/g$_{Fe}$ at 23 mT and SAR~486±97 W/g$_{Fe}$ at 88 mT). In order to confirm the contribution of rotation to the heat-producing mechanism of the chains of magnetosomes, we determined SAR$_{rot}$ using Equation 2, which factors in the Brownian relaxation time. This formula is only applicable below the saturating region where the SAR shows a strong dependence on the field amplitude (Hergt et al., *IEEE Trans. Mag.*, 1998, 34, 3745-3754). Since saturation occurs above ~36 mT (FIG. 3(*d*)), we only measured the SAR at 23 mT. Using a Brownian relaxation time $\tau_B$~1.2 10$^{-4}$ sec, we find that SAR$_{rot}$~3600 W/g$_{Fe}$ at 23 mT which is larger than the SAR of 774±145 W/g$_{Fe}$ we measured experimentally by measuring the difference between the SAR of magnetosome chains suspended in liquid (864±86 W/g$_{Fe}$) and the SAR due to the hysteresis losses (90±59 W/g$_{Fe}$). The difference between the theoretical prediction and the experimental observation may be explained by the partial aggregation of the chains of magnetosomes. We conclude that the rotation contributes to the heating mechanism of the chains of magnetosomes and that this contribution decreases from 90±10% of the SAR at 23 mT down to 40±10% of the same SAR at 88 mT (FIG. 3(*c*)). This decrease could be explained by the stronger enhancement with increasing magnetic field amplitude of the hysteresis losses than of the SAR due to the rotation of the chains of magnetosomes in the magnetic field (Hergt et al., *IEEE Trans. Mag.* 1998, 34, 3745-3754).

Figure 4:
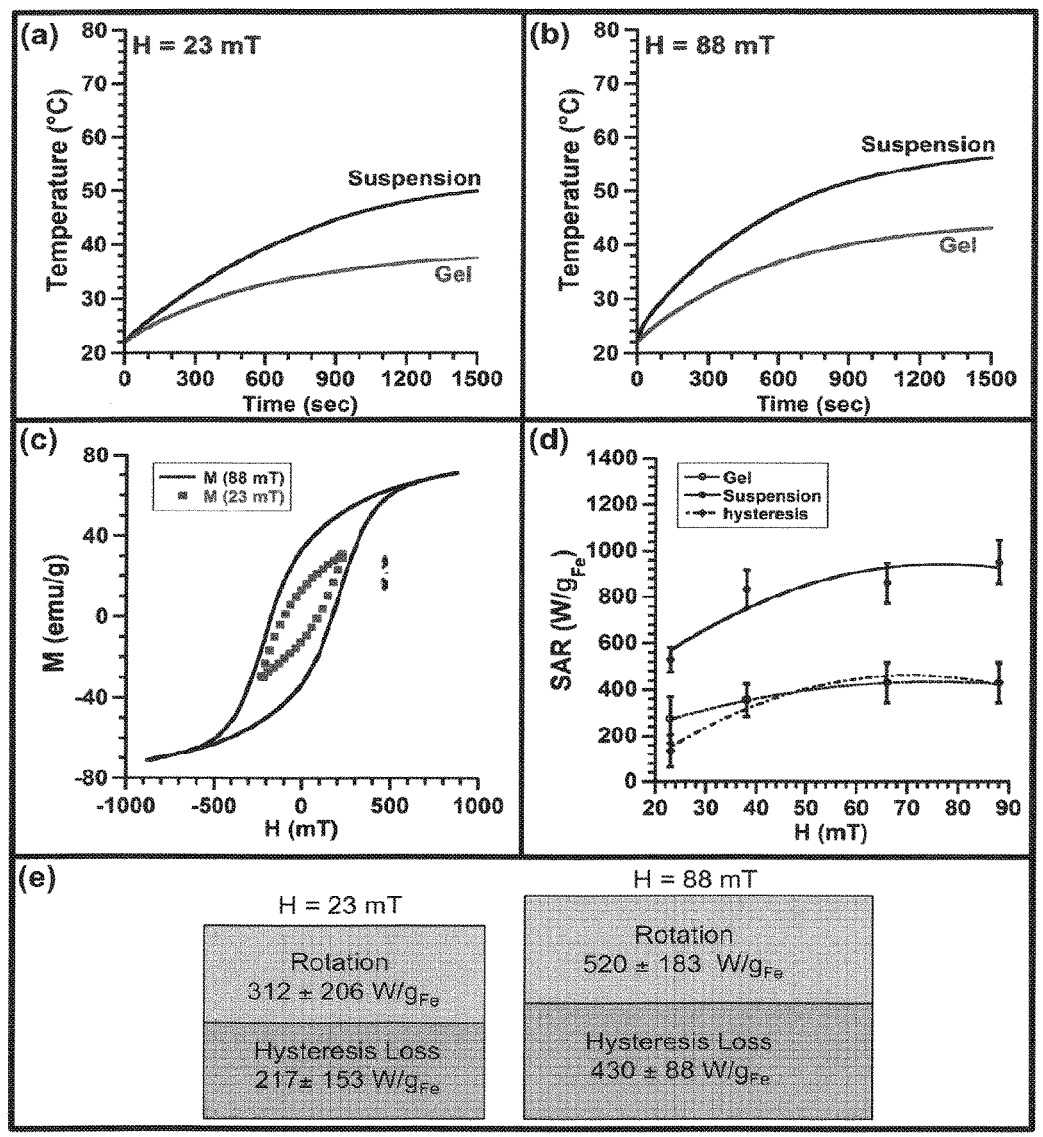
FIG. 4: Properties of individual magnetosomes extracted from cells of *Magnetospirillumm magneticum* strain AMB-1 and treated further by SDS and heat. (a) Increase in temperature of the individual magnetosomes as a function of time when an AMF of frequency 108 kHz and amplitude 23 mT is applied. The lines indicate the variations in temperature of the individual magnetosomes suspended in water (suspension) or in a 2% agarose gel (gel), respectively; (b) Same as in (a) for AMF amplitude of 88 mT. (c): Minor hysteresis loops of the individual magnetosomes measured at 23 mT (square) and 88 mT (line), (d) SAR measured from the slope at 22° C. of the heating rate of the individual magnetosomes contained either in water (suspension), or in a gel (gel), as a function of the AMF amplitude. Hysteresis losses measured from the area of the minor hysteresis loops of the individual magnetosomes contained in a gel (hysteresis); (e): Plots in column bars of the SAR of the individual magnetosomes measured at 23 mT and 88 mT. Boxes represent the contributions to the observed increases in temperature due to hysteresis losses and rotation of the individual magnetosomes, respectively.

The last sample we tested was a suspension of individual magnetosomes whose membranes had been mostly removed using a combination of heat and a detergent that dissolved lipids, sodium dodecyl sulfate (SDS). These crystals do not remain in chains as shown in FIG. 1(*c*). These nanocrystals interact and organize within compact assemblies of individual nanocrystals (Alphandéry et al., *ACS Nano.*, 2009, 3, 1539-1547, Alphandéry et al., *J. Phys. Chem.*, 2008, 112, 12304-12309; Kobayashi et al., *Earth Planet. Sci. Lett.*, 2006, 245, 538-555) unlike the magnetosomes with membranes shown in FIG. 1(*b*). The heating rates of the liquid suspension containing these individual magnetosomes are shown in FIGS. 4(*a*) and 4(*b*) for the magnetic field amplitudes of 23 mT and 88 mT. They are lower than those observed for the chains of magnetosomes suspended in liquid both at 23 mT and 88 mT (FIGS. 3(*a*), 3(*b*), 4(*a*) and 4(*b*)). The difference in solution heating rates observed between the chains of magnetosomes and the individual magnetosomes can either be due to a difference in the contribution of the magnetosome rotation or hysteresis losses to the SAR or a combination of both. The hysteresis losses were estimated either from the areas of the minor hysteresis loop (FIG. 4(*c*)) yielding SAR values lying between 270±100 W/g$_{Fe}$ at 23 mT and 427±85 W/g$_{Fe}$ at 88 mT or from the heating rates of the individual magnetosomes in the gel (FIGS. 4(*a*) and 4(*b*)) yielding SAR values lying between 135±70 W/g$_{Fe}$ at 23 mT and 432±86 W/g$_{Fe}$ at 88 mT. The hysteresis losses estimated by either of the two methods mentioned above (FIG. 4(*d*)) are similar to those estimated for the chains of magnetosomes (FIG. 3(*d*)). Therefore, the difference in SAR observed between the chains of magnetosomes and the individual magnetosomes suspended in liquid must result from a difference in the ability of the structures to rotate in the magnetic field. Equation 2 predicts that the SAR due to the rotation of the individual magnetosomes suspended in liquid should be the same as that deduced for the chains of magnetosomes, SAR$_{rot}$~3600 W/g$_{Fe}$ at 23 mT. Therefore the lower heating rate observed for the individual magnetosomes is most likely due to the fact that the latter are more prone to aggregation into clumps than the chains of magnetosomes. Aggregation of the individual magnetosomes is clearly evident using electron microscopy (FIG. 1(*c*)) and can also be observed visually in liquid suspension. It prevents these magnetosomes from rotating as easily as the chains of magnetosomes.

From these results, we can draw the following conclusions:
 (i) The SAR of each of the three magnetic samples (whole magnetotactic bacteria, chains of magnetosomes and individual magnetosomes) is larger than that reported for smaller superparamagnetic nanoparticles.
 (ii) The predominant contribution to heat production by the intact bacterial cells appears to be hysteresis losses while physical rotation and hysteresis losses are both responsible for the generation of heat for the chains of magnetosomes and individual magnetosomes mixed in solution.
 (iii) By contrast to their behavior in solution, the chains of magnetosomes and individual magnetosomes should less be able to rotate in vivo. Therefore the amount of heat that they should generate in vivo could be predicted by measuring their hysteresis losses. Since the chains of magnetosomes and individual magnetosomes have similar hysteresis losses, they presumably are both equivalently good candidates for the in vivo heat therapy.

Example 3

Improved Heating Efficiency of Extracted Chains of Magnetosomes Obtained by Synthesizing the Magnetotactic Bacteria in the Presence of Various Chelating Agents and/or Transition Metals.

In this example, we describe various methods to improve the heating efficiency of the extracted chains of magnetosomes suspended in water. These methods use various additives introduced within the growth medium of AMB-1 magnetotactic bacteria. These additives are chelating agents such as bisphosphonate molecules, dopamine, rhodamine, EDTA or transition metals such as cobalt.

Materials and Methods:

The growth medium of the magnetotactic bacteria was first prepared by following the same method as that described in example 1. Then one of the following additives was added to the growth medium of the magnetotactic bacteria: 0.4 µM, 4 µM or 40 µM of different types of bisphosphonic acids (alendronate, risedronate or neridronate), 4 µM, 20 µM or 400 µM of a solution of rhodamine, 0.4 µM or 4 µM of a solution of EDTA, 0.4 µM, 4 µM or 40 µM of a solution of dopamine, 2 µM or 20 µM of a solution of cobalt quinate. 1 mL of a suspension of magnetotactic bacteria was inserted within one litter of the above growth media and the bacteria grew during 10 days. After 10 days of growth, the bacteria were collected and the chains of bacterial magnetosomes were extracted from the bacteria following the same protocol as that described in the example 1. Five microliters of a suspension of chains of bacterial magnetosomes, containing $2 \times 10^{-4}\%$ in weight of magnetosomes were then deposited on top of a carbon grid for transmission electron microscopy (TEM) analysis. TEM was used to determine the sizes of the magnetosomes and to estimate the lengths of the chains. In order to evaluate the heating properties of the various types of extracted chains of magnetosomes, the latter were mixed in water. The concentrations of the different suspensions were estimated as the quantity of maghemite per milliliter. They were 0.3 mg/mL for the suspension containing the magnetosomes synthesized in the presence of several bisphosphonic acids, 1.52 mg/mL for the suspensions containing Co-doped magnetosomes and 0.406 mg/mL for that containing the magnetosomes synthesized in the presence of EDTA, rhodamine, dopamine or alendronate. The suspensions were heated under the application of an alternating magnetic field of frequency 183 kHz and strengths of 43 mT or 80 mT. The variation of temperature of these suspensions was measured using a thermocouple microprobe (IT-18, Physitemp, Clifton, USA).

Results and Discussion:

In this section, we compare the properties of chains of magnetosomes, which have been obtained by cultivating the magnetotactic bacteria in the standard conditions, i. e. in the absence of chelating agents and/or transition mestals (CM-Control) with those of the magnetosomes, which have been obtained by cultivating the magnetotactic bacteria in the presence of 0.4 µM EDTA (CM-EDTA). The results of the CM-EDTA are presented since they result in the most important change of the magnetosome properties, i. e. the largest increase in the magnetosome sizes, magnetosome chain lengths and heating efficiency compared with the CM-Control.

Figure 5:
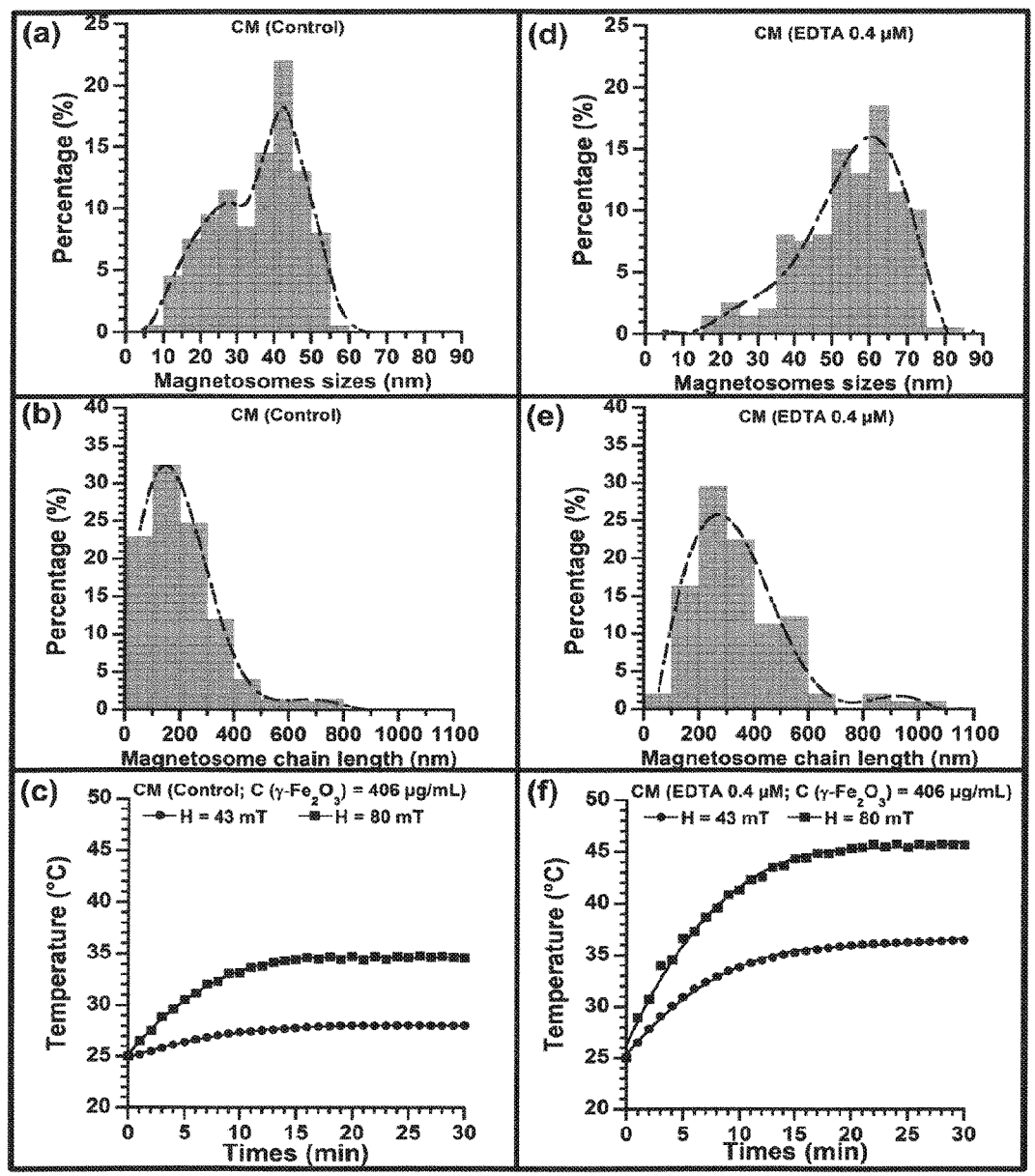
FIG. 5: (a-c): Properties of chains of magnetosomes extracted from magnetotactic bacteria, which have been synthesized in the absence of chelating agents and/or other transition metals than iron. Histograms showing the distribution in magnetosome sizes, (a), and magnetosome chain lengths, (b) of this type of magnetosomes. (c): The variation with time of the temperature of a suspension of this type of magnetosomes containing 406 µg/ml in maghemite when this suspension is exposed to an alternating magnetic field of frequency 183 kHz and magnetic field strength of either 43 mT or 80 mT. (d-f): Properties of chains of magnetosomes extracted from magnetotactic bacteria, which have been synthesized in the presence of 0.4 µM EDTA. Histograms showing the distribution in magnetosome sizes, (d), and magnetosome chain lengths, (e), of this type of magnetosomes. (f): The variation with time of the temperature of a suspension containing this type of magnetosomes with a concentration of 406 µg/ml of maghemite when the suspension is exposed to an alternating magnetic field of frequency 183 kHz and magnetic field strength of either 43 mT or 80 mT.

As shown in the histograms of FIGS. 5(a) and 5(d), both for the CM-Control and the CM-EDTA, the magnetosome size distributions seem to be bimodal with a higher percentage of large than small magnetosomes. The percentage of large magnetosomes is higher for the CM-EDTA (FIG. 5(d)) than for the CM-Control (FIG. 5(a)). Moreover, the fits of the magnetosome size distributions indicate that the size of the large magnetosomes increases from ~42 nm for the CM-Control (FIG. 5(a)) up to ~60 nm for the CM-EDTA (FIG. 5(d)). We also observe that the percentage of small magnetosomes (<30 nm) is significant for the CM-Control (>25%, FIG. 5(a)) while it is small for the CM-EDTA (<10%, FIG. 5(d)). As can be observed by comparing the histograms presented in FIGS. 5(b) and 5(e), the average magnetosome chain length also increases from ~150 nm for the CM-Control (FIG. 5(b)) up to ~300 nm for the CM-EDTA (FIG. 5(e)). Long chains of magnetosomes (>800 nm in length) are only present for the CM-EDTA (FIG. 5(e)). When the alternating magnetic field is applied to the suspensions containing the CM-EDTA, it produces an increase in temperature, which is larger for the CM-EDTA than for the CM-Control for both magnetic field strengths of 43 mT and 80 mT (FIGS. 5(c) and 5(f)). Moreover, the saturating temperatures for the CM-EDTA (35° C. and at 43 mT and 45° C. and at 80 mT, FIG. 5(f)) are both higher than those obtained for the CM-Control (28° C. at 43 mT and 35° C. at 80 mT, FIG. 5(c)). These features reveal the higher heating capacity of the CM-EDTA as compared with the CM-Control, which could be attributed to an increase in the magnetosome sizes and/or magnetosome chain lengths.

Figure 6:
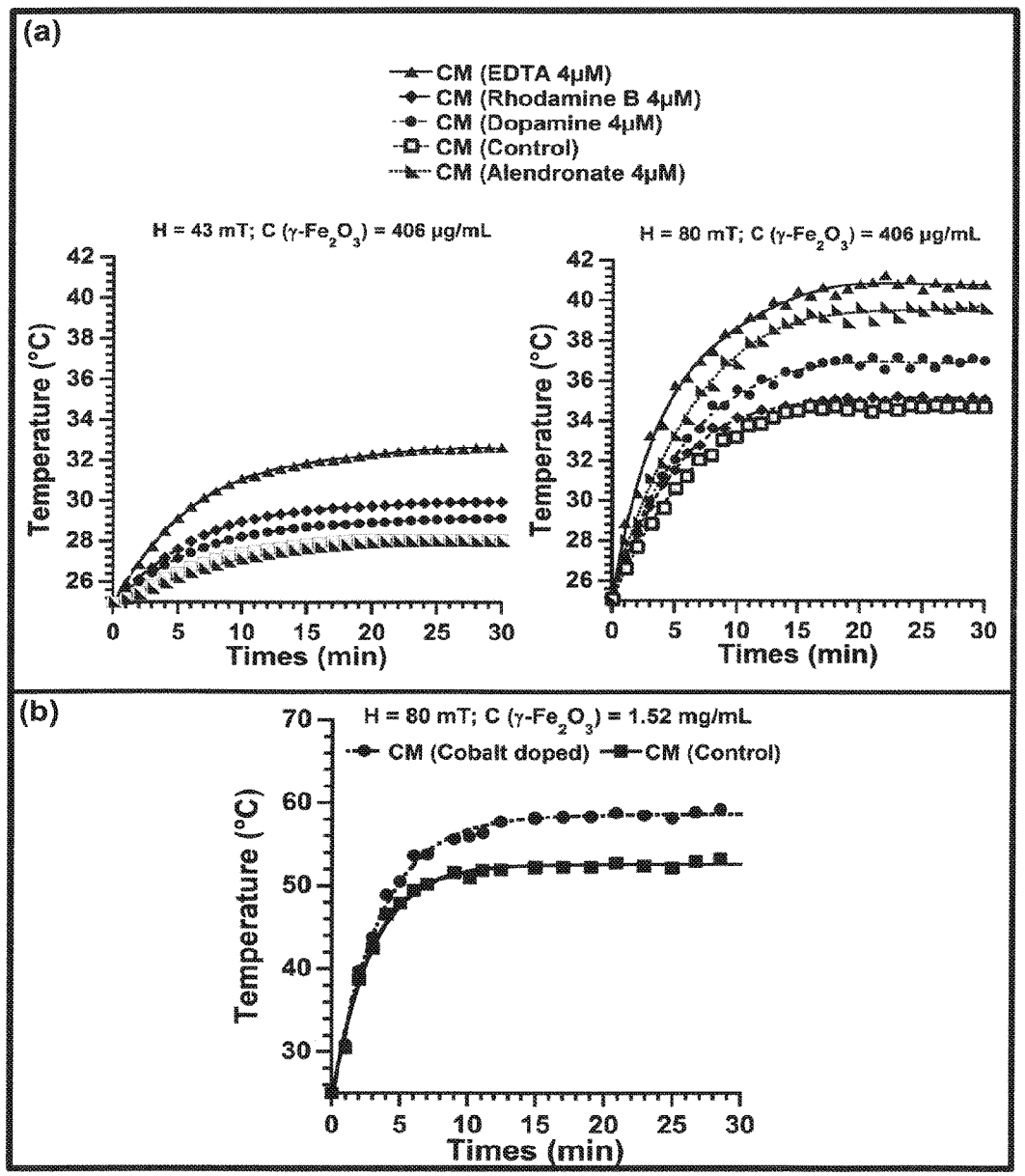
FIG. 6: (a) The variation as a function of time of the temperature of several suspensions containing different types of chains of magnetosomes synthesized in the presence of different chelating agents (4 µM EDTA, 4 µM Rhodamine B, 4 µM Dopamine, 4 µM Alendronate) and 406 µg of maghemite per milliliter when these suspensions are submitted to an alternating magnetic field of frequency 183 kHz and field strength of either 43 mT or 80 mT. (b) The variation as a function of time of the temperature of two suspensions containing undoped and Co-doped magnetosomes organized in chains. The concentration of these suspensions is 1.52 mg/mL and they are exposed to an alternating magnetic field of frequency 183 kHz and field strength of 80 mT.

For a series of other chelating agents introduced in the bacterial growth medium, the same trends as those observed with 0.4 µM EDTA can be observed but with a less pronounced effect. As shown in FIG. 6(a), the temperature increases more rapidly under the application of an alternating magnetic field of strength 43 mT or 80 mT for the chains of magnetosomes issued from the bacteria cultivated in the presence of various chelating agents (4 µM Rhodamine B, 4 µM dopamine, 4 µM Alendronate) than for the CM-control.

Figure 17:
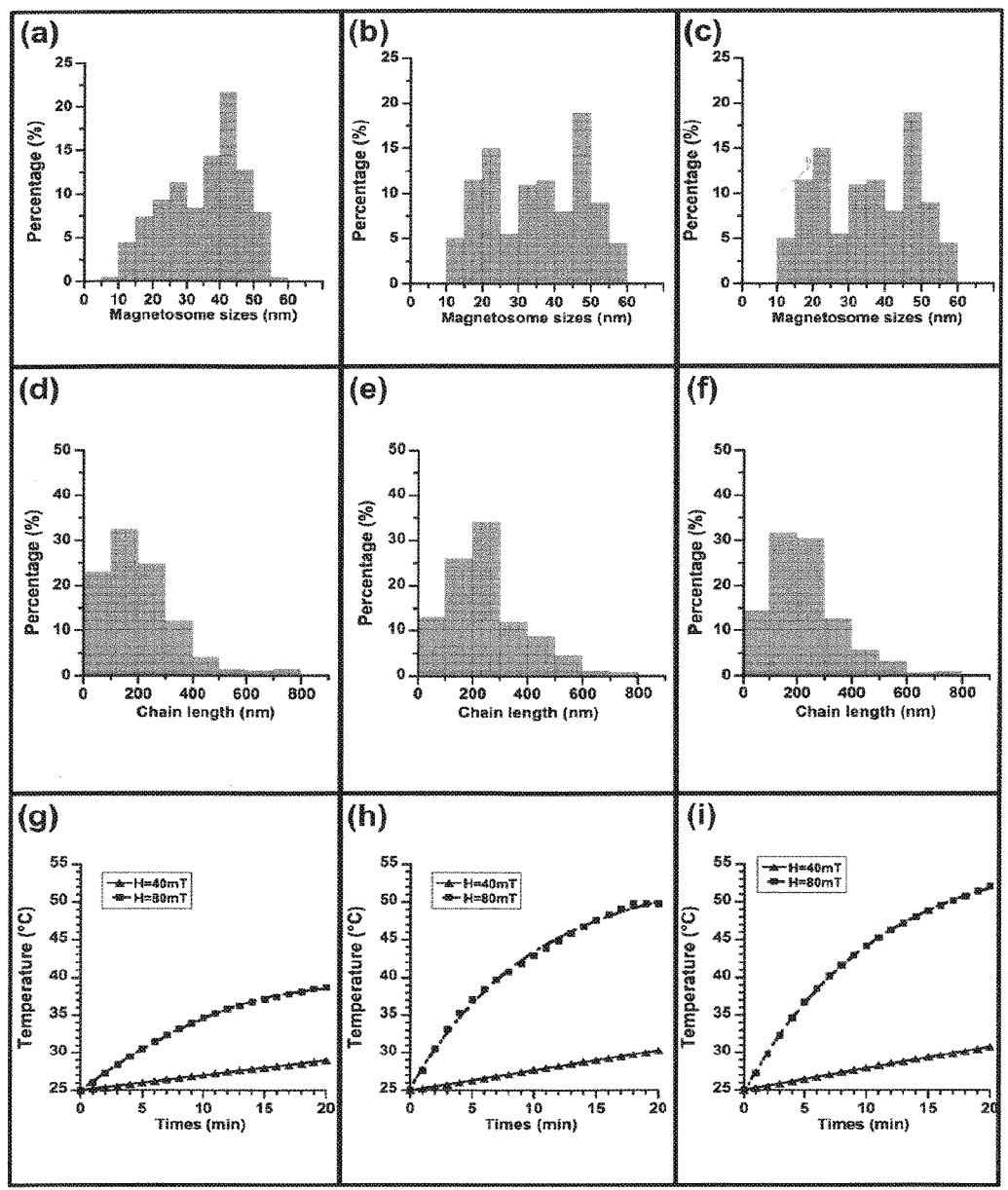
FIG. 17: Histograms showing the magnetosome size distributions for magnetotactic bacteria synthesized in the absence of a bisphosphonic acid, (a), in the presence of 4 µM risedronate, (b), or in the presence of 4 µM alendronate, (c). Histograms showing the magnetosome chain length distributions for magnetotactic bacteria synthesized in the absence of a bisphosphonic acid, (d), in the presence of 4 µM risedronate, (e), or in the presence of 4 µM alendronate, (f). Variations of the temperatures as a function of time when an alternating magnetic field of strength 43 mT or 80 mT is applied to a suspension containing chains of magnetosomes synthesized in the absence of a bisphosophonic acid, (g), in the presence of 4 µM risedronate, (h), or in the presence of 4 µM alendronate, (i).

When the magnetosomes were synthesized in the presence of 4 µM risedronate or 4 µM alendronate, the percentage of magnetosome with sizes larger than 45 nm becomes larger than that of the magnetosomes synthesized in the absence of bisphosphonic acid (FIGS. 17(a), 17(b) and 17(c)). The percentage of chains with lengths larger than 400 nm is also higher for the magnetosomes synthesized in the presence of bisphosphonic acid (FIGS. 17(e) and 17(f)) than for those synthesized in the absence of bisphosphonic acid (FIG. 17(d)). Because of these behaviors, the variation of temperature induced by the application of a magnetic field is larger for the magnetosome synthesized in the presence of 4 μμM risedronate (FIG. 17(h)) or 4 μM alendronate (FIG. 17(i)) than for those synthesized in the absence of bisphosphonic acid (FIG. 17(g)). This behavior is observed both for a magnetic field strength of 40 mT and 80 mT. For bisphosphonic acids with concentrations of 0.4 μM introduced in the growth medium, similar results as those obtained for a concentration of 4 μM were observed. By contrast, for a concentration in bisphosphonic acid of 40 μM introduced in the bacterial growth medium, the properties of the chains of bacterial magnetosomes were not significantly different from those of the bacterial magnetosomes synthesized in the standard conditions. These results suggest that the concentrations in bisphosphonic acid necessary to reach optimum heating efficiency lie between 0.1 and 40 μM, in particular between 0.1 and 10 μM, typically between 0.4 and 4 μM. A third bisphosphonic acid (neridronic acid) was also tested and yielded similar results as those obtained with alendronic or risedronic acid.

The AMB-1 magnetotactic bacteria were also cultivated in a growth medium, which contained the chemicals of ATCC Medium 1653 and a 20 μM or 400 μM solution of rhodamine. When 55 μg of chains of magnetosomes synthesized in the presence of rhodamine and mixed in one milliliter of water were subjected to an alternating magnetic field of 43 mT the temperature of the suspension increased by 3 degrees in 30 minutes. For the chains of magnetosomes synthesized in the absence of rhodamine, a temperature increase of only one degree was observed in the same experimental conditions. This shows that the presence of rhodamine in the growth medium yields improved heating capacity of the chains of magnetosomes.

The heating efficiency of the extracted chains of magnetosomes synthesized by introducing a 20 μM cobalt quinate solution within the bacterial growth medium has also been tested. The presence of cobalt within some of the magnetosomes has been detected using energy electron loss spectroscopy (EELS) measurements. This result agrees with that of Staniland et al (S. Staniland et al, *Nature Nanotech.*, 2008, 3, 158-162), which also showed the presence of cobalt within the magnetosomes for magnetotactic bacteria synthesized in similar conditions. As shown in FIG. 6(b), when the suspension containing the Co-doped magnetosomes ($C_{\gamma Fe2O3}$=1.52 mg/mL) is exposed to an alternating magnetic field of strength 80 mT and frequency 183 kHz, the temperature of the suspension increases more than that containing the CM-Control. Since the magnetosome sizes and magnetosome chain lengths have been shown to be very similar for the undoped and Co-doped magnetosomes, the enhanced heating efficiency of the Co-doped magnetosomes could be explained by an increase in their magnetocrystalline anisotropy.

From these results, we can draw the following conclusions:
(i) The introduction of iron chelating agents of concentrations lying between 0.1 μM and 1 mM within the AMB-1 bacterial growth medium yields improved heating properties of the extracted chains of magnetosomes mixed in solution. We believe that this behavior is due to an increase of the magnetosome sizes and/or magnetosome chain lengths when the bacteria are cultivated in these conditions.
(ii) The introduction of cobalt quinate with a concentration lying between 0.1 μM and 1 mM within the AMB-1 bacterial growth medium also yields improved heating properties of the extracted chains of magnetosomes mixed in solution. We believe this behavior is due to an increase of the magnetocrystalline anisotropy of the magnetosomes doped with cobalt.
(iii) The introduction of iron chelating agents and/or cobalt quinate within the bacterial growth medium provides a way to enhance the heating efficiency of the chains of magnetosomes. This open the way to use these chains of magnetosomes in a smaller amount in the thermotherapy, hence reducing the risk of toxicity induced by the presence of the chains of magnetosomes.

Example 4

Efficiency of the Thermotherapy Evaluated In Vitro.
Materials and Methods:
MDA-MB-231 cells were obtained from the American Type Culture Collections (ATCC). The cells lines were cultivated in Dulbecco's modified Eagle's medium (DMEM) supplement, which contained 10% fetal calf serum (FCS), 2 mM l-glutamine, 1 mM sodium pyruvate, 50 U/ml streptomycin (all purchased from Life Technologies Inc.). All in vitro experiments were carried out at 37° C. in an incubator with 5% of $CO_2$.

Cell viability was evaluated using the so-called MTT (microculture tetrazolium assay, T. Mosmann, 1983, *J. Immunol. Methods*, 65, 55-63). This technique measures the ability of mitochondrial enzymes to reduce 3-(4,5-dimethylthiazol-2-yl)-2,5-diphenyltetrazolium bromide (purchased from Sigma, St Louis, Mo., USA) into purple formazan crystals. Cells were seeded at a density of 2 $10^4$ cells per well in 96-well flat-bottom plates (Falcon, Strasbourg, France) and incubated within the culture medium during 24 hours. Then, the medium was removed and replaced by 10% FCS-medium containing the various nanoparticles (chains of magnetosomes, individual magnetosomes, SPION@Citrate and SPION@PEG) with different concentrations in maghemite (0.125 mg/mL<$C_{\gamma Fe2O3}$<1 mg/mL). These suspensions were exposed (or not for the control) to an alternating magnetic field of frequency 183 kHz and strength of 43 mT. The treatment was carried out during 20 minutes either one time or two times. After 72 hours of incubation, the cells were washed with a phosphate buffer saline (PBS from Life Technologies) and incubated with 0.1 mL of MTT (2 mg/mL) for an additional 4 hours at 37° C. The insoluble product (composed essentially of formazan) was then dissolved by adding 100 μl of DMSO (Sigma-Aldrich). The absorbance of the solubilized formazan was measured at 570 nm using a Labsustem Multiscan MS microplate reader. It provided an estimate of the number of functional mitochondria, a number, which is proportional to the number of living cells. The percentage of inhibition was then estimated as the number of dead cells (i. e. cells in apotosis) divided by the total number of cells.

For the toxicity studies, the cells were seeded on Petri dishes (diameter of 30 nm with 50 000 cells per Petri dish), and grew during 24 hours. After this initial period of growth, the cells were incubated in the presence (or not for the control) of the various types of nanoparticles studied during 24 hours, 48 hours or 72 hours. At the end of the incubation time, the cells were exposed (or not for the control) to an alternating magnetic field of frequency 183 kHz and strengths 20 mT, 43 mT or 60 mT. The treatment was carried out during 20 minutes either one time or two times. Following the treatment, the cells were washed twice with PBS. Then in order to harvest the cells, 250 µl of Trypsin-EDTA were added to the adherent cells. 750 µl of the liquid medium were added to the harvested cells to homogenize the suspension. The suspension was then centrifugated at 700 G during 3 minutes, the supernate was removed and the cells were resuspended in 1 mL of PBS. In order to evaluate the percentage of living cells, 5 µl of propidium iodide (PI) (1 mg /mL mixed in ethanol, Sigma Aldrich) was added to the cell suspensions. Since PI only penetrates within dead cells, the measurement of its fluorescence provides an estimate of the percentage of dead cells. From this estimate, we could deduce the percentage of living cells. In order to measure the fluorescence of PI, the cells were analyzed in a flow cytometer (Beckton Dickinson FACSCalibur 3C), which contains an argon laser with an emission at 488 nm and a detector FL3-H able to detect the fluorescence of PI excited by the laser. Ten thousand cells per sample were measured to determine the percentage of living cells.

In order to measure the heating properties of the cell suspensions in vitro, essentially the same experiment as that described above for the adherent cells has been carried out for the cells in suspension. The only difference in this case is that the cells have immediately been mixed with the chains of magnetosomes and treated by application of the magnetic field. The temperature was measured with the thermocouple microprobe (IT-18, Physitemp, Clifton, USA), which measures the temperature macroscopically (i. e. the temperature of the cell suspension as a whole but not the temperature within each individual cell).

In order to estimate the number of magnetic cells, essentially the same protocol as that described above for the cells in suspension was followed. 50 000 cells contained within the liquid medium described above were incubated in the presence of the various nanoparticles during 5 to 20 minutes. During the incubation, an alternating magnetic field of frequency 183 kHz and field strength of 43 mT was applied. After treatment, the magnetic cells were collected by positioning a strong magnet of 0.6 mT close to the cells in suspension. The supernate containing the non-magnetic cells was removed while the cells which had been attracted by the magnet were resuspended in 1 mL of PBS. The percentage of magnetic cells was then estimated using the flow cytometer.

Figure 7:
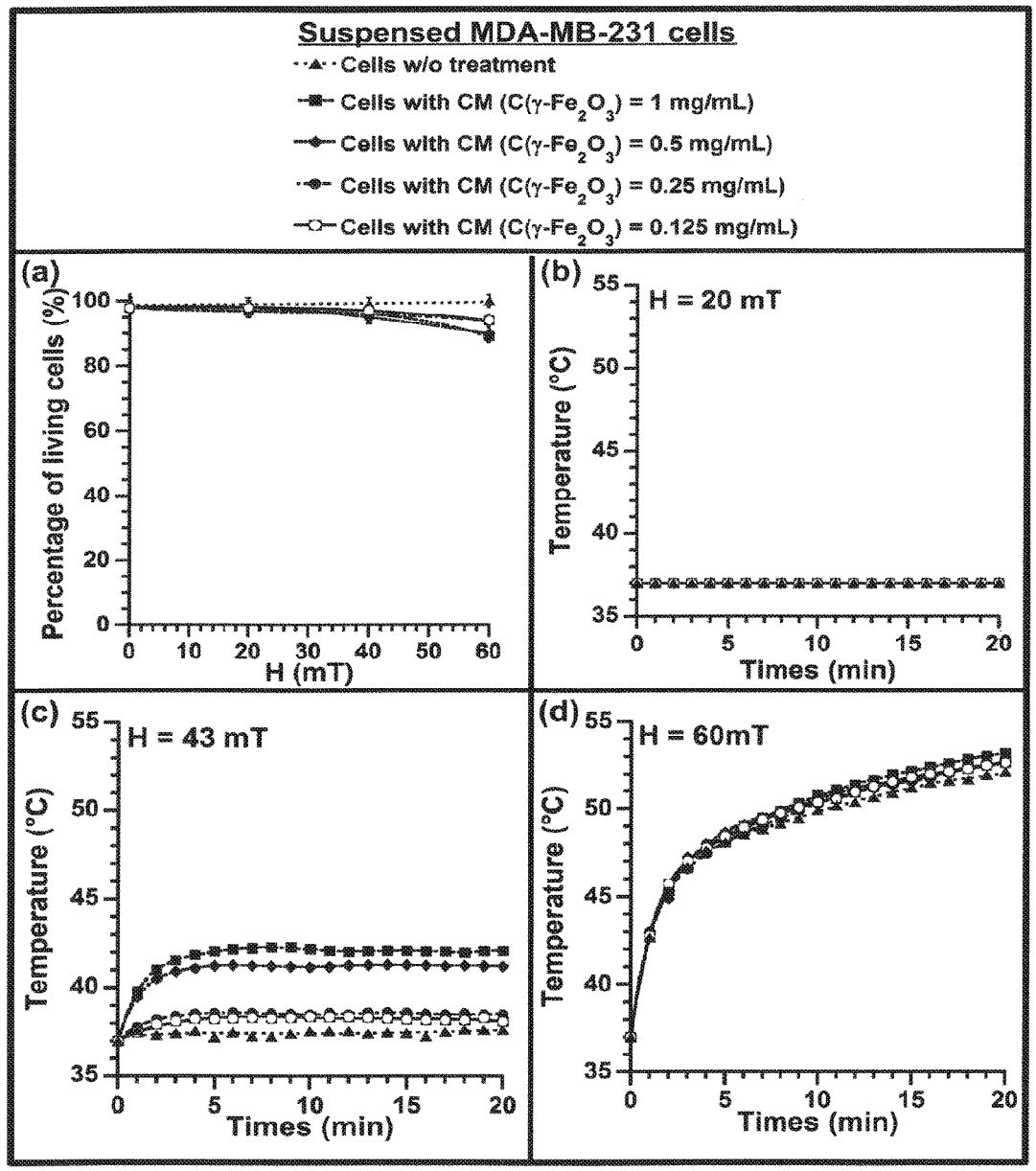
FIG. 7: Properties of suspended MDA-MB-231 cells incubated in the absence or in the presence of extracted chains of magnetosomes of various concentrations (0.125 mg/mL<$C\gamma_{Fe2O3}$<1 mg/mL, where $C\gamma_{Fe2O3}$ represents the concentration in maghemite of the suspensions) and exposed to an alternating magnetic field of frequency 183 kHz and various strengths (0 mT<B<60 mT, where B represents the strength of the applied magnetic field). (a): Percentage of MDA-MB-231 living cells as a function of the magnetic field strength for an incubation of suspensions of chains of magnetosomes of various concentrations. (b)-(d): Variations of temperature of suspensions containing MDA-MB-231 cells incubated in the absence or in the presence of chains of magnetosomes of various concentrations (0.125 mg/mL<$C\gamma_{Fe2O3}$<1 mg/mL) when an alternating magnetic field of B=20 mT, (b), B=43 mT, (c), or B=60 mT, (d), is applied to these suspensions.

Results and Discussions:

For the treatment with the cells in suspension, the cells were first incubated during a few minutes in the presence of a suspension of chains of magnetosomes of various concentrations. At the same time, an alternating magnetic field of frequency 183 kHz and various strengths (0 mT<B<60 mT) was applied. The percentage of living cells was then measured in the flow cytometer for the different magnetic field strengths. FIG. 7(a) shows that the percentage of living cells is high (>80%) for the different strengths of the applied magnetic field, indicating low toxicity. This could be explained by the fact that the cells don't reach the state of apoptosis just after the treatment. For the cells incubated in the presence of various quantities of chains of magnetosomes during a few minutes, the variations of temperature of the suspensions, which is due to the application of the alternating magnetic field, are shown in FIGS. 7(b), 7(c) and 7(d) for magnetic field strengths of 20 mT (FIG. 7(b)), 43 mT (FIGS. 7(c)) and 60 mT (FIG. 7(d)) respectively. As shown in FIG. 7(b), the magnetic field strength of 20 mT is too low to result in an increase of temperature. By contrast, FIG. 7(d) shows that the magnetic field strength of 60 mT induces a large increase in temperature. The latter takes place even for the cells incubated in the absence of the chains of magnetosomes indicating that it arises from the Foucault's currents. The magnetic field of strength 43 mT is the one which provides an acceptable behavior, i. e. no variation of temperature in the absence of the chains of magnetosomes and an increase in temperature, which increases with an increasing quantity of chains of magnetosomes incubated (FIG. 7(c)).

Figure 8:
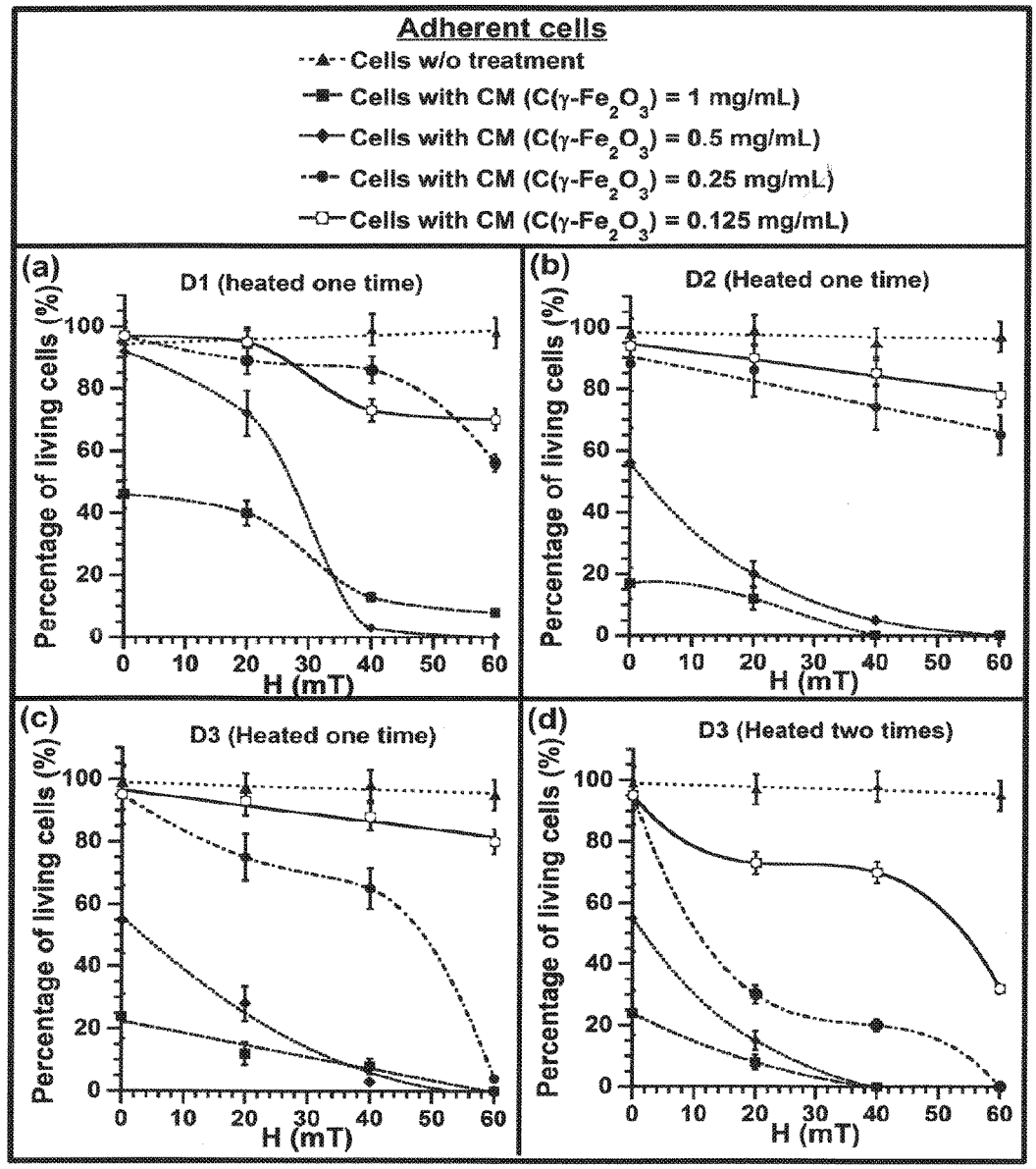
FIG. 8: (a)-(c): Percentage of living adherent MDA-MB-231 cells as a function of the strength of the magnetic field (0 mT<B<60 mT), which is applied once during 20 minutes. The cells are either incubated during 24 hours, D1, (a), 48 hours, D2, (b) or 72 hours, D3, (c) either in the absence or in the presence of the extracted chains of magnetosomes of various concentrations (0.125 mg/mL<$C\gamma Fe_{2O3}$<1 mg/mL). (d): Percentage of living adherent MDA-MB-231 cells as a function of the magnetic field strength (0 mT<B<60 mT), which is applied two times during 20 minutes. The cells are incubated during 72 hours in the absence or in the presence of the extracted chains of magnetosomes of various concentrations (0.125 mg/mL<$C\gamma_{Fe2O3}$<1 mg/mL).

For the adherent cells incubated during more than a few minutes, the percentage of living MDA-MB-231cells has also been measured as a function of magnetic field strengths (FIG. 8). The cells have been incubated in the presence of suspensions of chains of magnetosomes of various concentrations during 24 hours (D1, FIG. 8(a)), 48 hours (D2, FIG. 8(b)) or 72 hours (D3, FIGS. 8(c) and 8(d)). The treatment induced by heat has been carried out either one time (FIGS. 8(a) to 8(c)) or two times (FIG. 8(d)). In the absence of the magnetic field, the presence of the chains of magnetosomes is toxic (less than 50% of living cells) for 1 mg of chains of magnetosomes incubated during 48 hours or 72 hours. For all the other conditions tested, the presence of the chains of magnetosomes exhibits low toxicity (more than 50% of living cells). In the presence of a magnetic field, FIGS. 8(a) to 8(c) show that the percentage of living cells decreases significantly for a magnetic field of 43 mT or more and for a quantity of magnetosomes incubated of more than 0.5 mg. FIG. 8(d) shows that by repeating the treatment twice it is possible to improve the efficiency of the treatment, where the latter is defined by a high percentage of living cells destroyed using a small quantity of magnetosomes. Indeed, for a treatment carried out two times, the percentage of living cells of 20% is reached for 0.25 mg of chains of magnetosomes used (B=43 mT) (FIG. 8(d)) compared with 0.5 mg for a treatment carried out one time (B=43 mT) (FIG. 8(c)).

Figure 9:
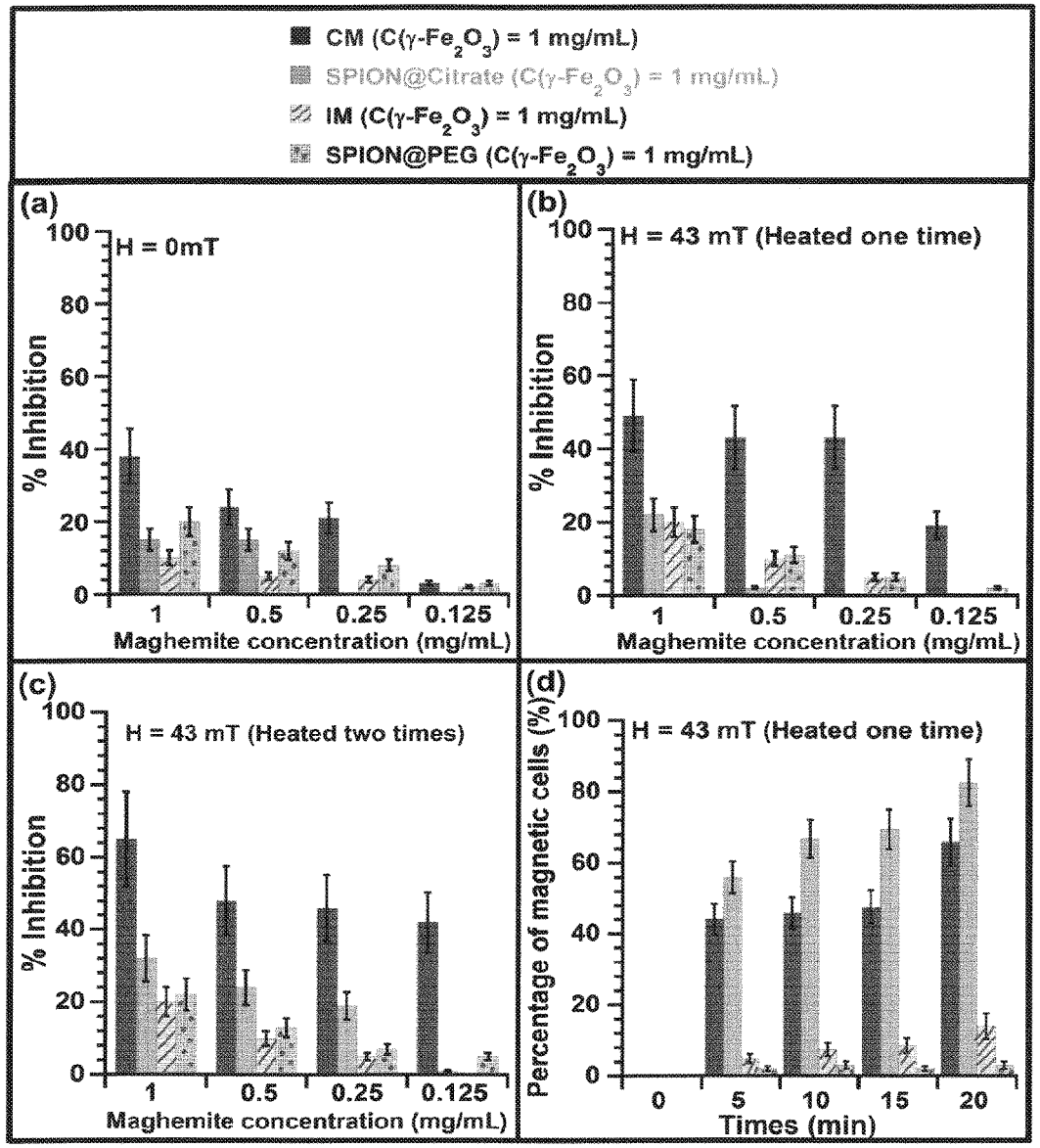
FIG. 9: Percentage of inhibition of MDA-MB-231 cells incubated in the presence of four different suspensions containing chains of magnetosomes (CM), individual magnetosomes (IM), SPION covered by citrate ions (SPION@Citrate), SPION covered by PEG molecules (SPION@PEG) as a function of the concentration in maghemite of these four suspensions. (d) Percentage of cells, which become magnetic as a function of the incubation time, when the four suspensions mentioned above (0.125 mg/mL<$C\gamma_{Fe2O3}$<1 mg/mL) are incubated in the presence of MDA-MB-231 cells and an alternating magnetic field of 183 kHz and strength of 43 mT is applied.

The percentage of inhibition of MDA-MB-31 cells incubated in the presence of the various types of nanoparticles mentioned above has also been estimated either in the absence of a magnetic field (FIG. 9(a)) or in the presence of a magnetic field of 43 mT for a treatment carried out either one time (FIG. 9(b)) or two times (FIG. 9(c)). In all conditions tested, the percentage of inhibitions of the cells is larger for the MDA-MB-31 cells incubated in the presence of the chains of magnetosomes than for those incubated in the presence of all other types of nanoparticles (the individual magnetosomes, the SPION@Citrate and the SPION@PEG). The best conditions for the treatment (i. e. those, which result in a high percentage of inhibition in the presence of a magnetic field and in a low percentage of inhibition in the absence of a magnetic field) are obtained for the smallest quantity of chains of magnetosomes of 0.125 mg used and for the treatment carried out more than one time (FIGS. 9(a) and 9(c)).

FIG. 9(d) shows the percentage of MDA-MD-231 cells, which become magnetic when they are incubated in the presence of the various types of nanoparticles while the alternating magnetic field of 43 mT is applied between 0 and 20 minutes. The percentage of magnetic cells is high for the cells incubated in the presence of the chains of magnetosomes and of the SPION@Citrate. It lies between 40% and 90% depending on how long the alternating magnetic field is applied (FIG. 9(d)). FIG. 9(d) also shows that the percentage of internalization of the individual magnetosomes within the MDA-MD-231 cells is low (<20%). This may be explained by the tendency of the individual magnetosomes to aggregate, which prevents them from penetrating within the cells As shown in FIG. 9(d), the SPION@PEG possess a very low percentage of internalization within the MDA-MD-231 cells, indicating that the percentage of internalization of magnetic nanoparticles within eukaryotic cells after application of an alternating magnetic is strongly dependent on the type of nanoparticles used.

From these results, we can draw the following conclusions:
  (i) In the absence of treatment, the cytotoxicity of the chains of magnetosomes is low for a quantity of chains of magnetosomes below 1 mg.
  (ii) The magnetic field strength of 43 mT yields the best heating property for MDA-MB-231 cells suspended in the presence of chains of magnetosomes of various concentrations.
  (iii) The best conditions are reached for the lowest quantity of chains of magnetosomes incubated (0.125 mg) and for the treatment repeated twice.
  (iv) The higher percentage of inhibition reached for the chains of magnetosomes as compared with the individual magnetosomes could be due to a better internalization of the chains of magnetosomes within the MDA-MD-231cells as compared with that of the individual magnetosomes.
  (v) The higher percentage of inhibition observed for the cells incubated in the presence of the chains of magnetosomes compared with that observed for the cells incubated in the presence of the SPION@Citrate may be explained either by the higher SAR of the chains of magnetosomes or by the more homogenous heating of the chains of magnetosomes or by a combination of both of these properties.

Example 5

Heating Efficiency and Antitumoral Activity of Various Bacterial Magnetosomes and SPION@Citrate.

In this example, the in vivo heating efficiency and antitumoral activity of chains of magnetosomes, individual magnetosomes, SPION@Citrate and whole magnetotactic bacteria are compared.

Materials and Methods:

All animal experiments have been conducted after approval of a protocol examined by the committee of the "Centre Léon Bérard, Ecole normale supérieure, Plateau de Biologie Expérimentale de la Souris, Lyon, France".

In vivo heating experiments were carried out on 30 nude mice at 6 weeks of age, which were bought in Charles Rivers Laboratories, Arbresle, France. To prepare tumor-bearing animals, the mice were first gamma-irradiated. Approximately two millions MDA MB 231 human breast cancer cells in 100 µl of phosphate buffer saline (PBS) were then injected subcutaneously both on the left and right flanks of the mice using a syringe (26 G needle). The tumor sizes were measured using calipers every 3 days. The estimates of the volumes of the tumors were then carried out using the formula $V=A \times B^2/2$, where A is the longer and B is the shorter lateral diameter of the tumor (Sun et al., *Cancer Lett.*, 2007, 258, 109-117). The tumors grew during a period of 21 days until they reached a volume of approximately 100 $mm^3$.

Figure 10:
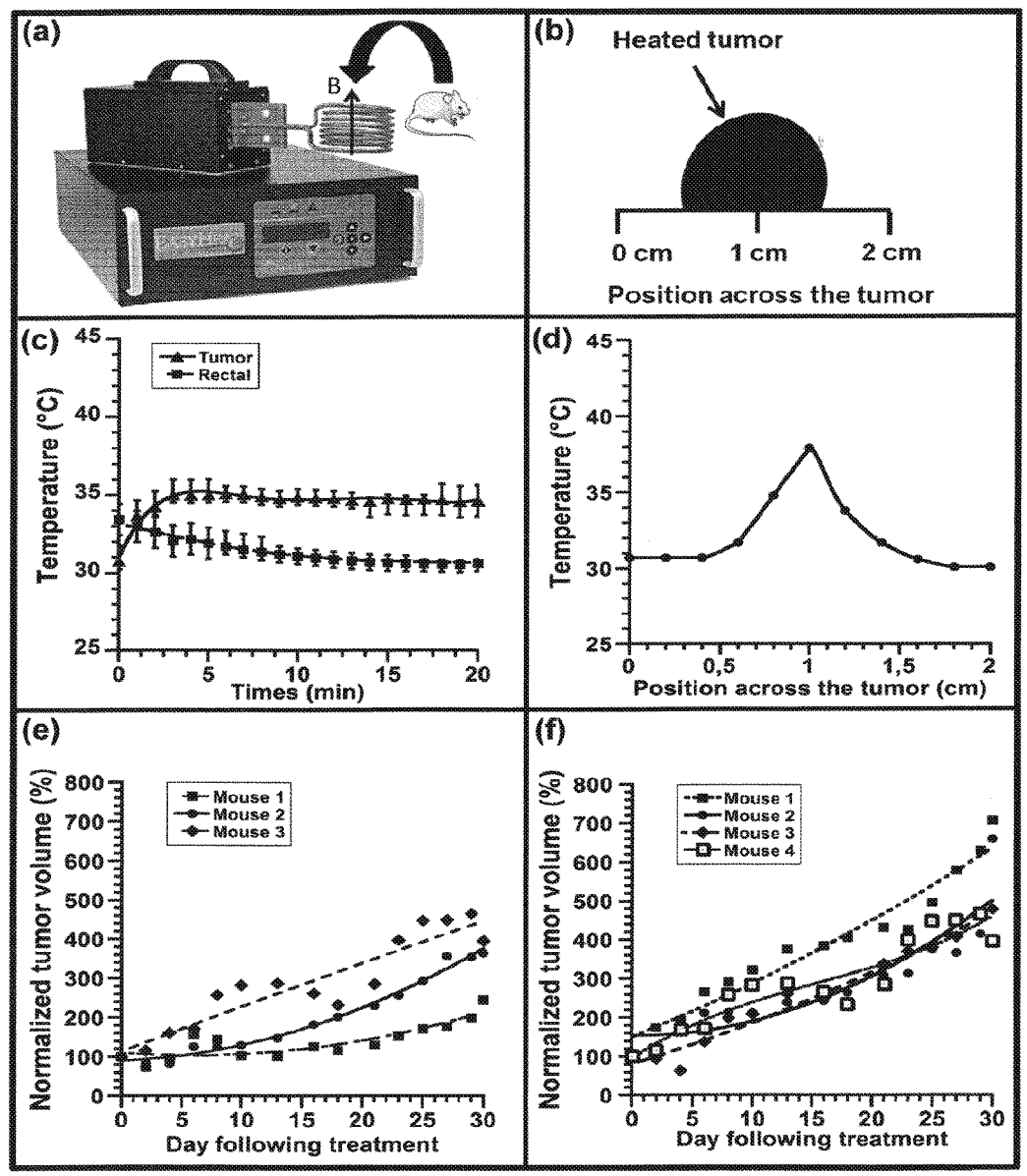
FIG. 10: (a) Experimental set-up used to treat the mice. It contains a 10 kW EasyHeat power supply from Ambrell, Soultz, France, equipped with a coil of 6.7 cm in diameter where an AMF of various strengths (varied from 20 mT and 80 mT) is applied. A mouse is positioned inside the coil for treatment. (b) Schematic diagram showing the heated tumor and the position across the tumor, which is recorded during the infrared measurements of the temperature. (c)-(f): Study of mice treated with suspensions of individual magnetosomes (mice 1 to 4). (c) The variations of the tumor and rectal temperatures when the magnetic field is applied during the treatment. These temperatures are averaged over the different mice treated (mice 1 to 3); (d) For a mouse showing a typical behavior, the temperature distribution measured across the treated tumor 10 min after the treatment has started; (e) Variation of the normalized tumor volume for the tumor in which the suspension of individual magnetosomes has been injected (mice 1 to 3). The volumes of the tumors are normalized by the volume of the tumor at the time of the treatment; (f) Same as in (e) for the so-called control tumor in which only PBS has been injected. In mouse 4, the suspension of individual magnetosomes has been injected but no magnetic field has been applied.

Before starting the treatment, the mice were anesthetized with ketamin/xylazin (100/6 mg $kg^{-1}$, i.p.), which resulted in a decrease of their corporal temperature from 37° C. down to 30-36° C. depending on the mouse. Three mice died during the first steps of the treatment most probably due to an overestimation of the dose of anesthetic. After necropsy, the organs of these mice showed no obvious systemic congestion or infarction. Under anesthesia, the needle of the syringe containing either chemically synthesized nanoparticles or the various types of bacterial magnetosomes dispersed in sterile water was inserted longitudinally into the tumors of the mice. The mice were then placed inside a coil of 6.7 cm in diameter where an alternating magnetic field was applied to them. To produce the alternating magnetic field, an alternating current was generated within the coil using a 10 kW EasyHeat power supply from Ambrell, Soultz, France. The schematic diagram of FIG. 10(a) shows the experimental set-up used to carry out the experiments. The measurements of the temperature were carried out using an implantable thermocouple microprobe (IT-18, Physitemp, Clifton, USA) to obtain the rectal temperature or a local estimate of the temperature within the central part of the tumor. The variation of the rectal temperature was monitored to verify that the increase of the tumor temperature was local and did not take place within the whole body of the mice. An infrared camera (Moblr2, Optophase, Lyon, France) was used to obtain a more global picture of the variation of temperature of the tumor and of the tumor environment. The cross section through which the temperature was measured is indicated in the schematic diagram of FIG. 10(b) by a line. The variations of the tumor sizes during the 30 days following the first treatment were measured both for the unheated and heated tumors.

Antitumoral activity was studied by following the size evolution of tumors grown subcutaneously on both flanks of each mouse. Mice were randomly selected and divided into five groups. The first four groups were treated as follows. One hundred microliters of suspensions containing individual magnetosomes (suspension 1 in mice 1 to 3), chains of magnetosomes (suspension 2 in mice 5 to 8), SPION (suspension 3 in mice 10 to 13) and whole magnetotactic bacteria (suspension 4 in mice 15 and 16) were administered into the tumors localized on the right flank of the mice. After injection of the different suspensions, mice were subjected to an alternating magnetic field of frequency 183 KHz and magnetic field strength of ~43 mT (mice 1, 2, 3, 5, 6, 7, 8, 10, 11, 12, 13) or ~80 mT (mice 15 and 16) during 20 min. The treatment was repeated 3 times at 3 days interval. For the mice, which received the suspension of chains of magnetosomes, the magnetic field had to be reduced by ~5 mT to avoid that the temperature within the tumor exceeds 50° C. For the mice, which received the whole bacteria, the magnetic field strength had to be increased to ~80 mT to observe a temperature increase within the tumor. The fifth group was considered as a control group and was not subjected to the application of an alternating magnetic field. This group was composed of mice, which received into the tumors localized on their right flank, 100 µl of physiological water (mice 17 and 18), 100 µl of suspension 1 (mice 4, 19 and 20), 100 µl of suspension 2 (mice 9, 21 and 22), 100 µl of suspension 3 (mice 14, 23 and 24) and 100 µl of suspension 4 (mice 25, 26, 27). Finally, the 27 tumors localized on the left flank of each mouse were used as internal control and only received physiological water.

The concentrations of the different suspensions (10 mg $ml^{-1}$ for suspensions 1 and 3 and 20 mg $ml^{-1}$ for suspension 2) were chosen in such a way that they yielded similar heating properties in water. These concentrations represent the amount of maghemite contained in one milliliter of water. They were estimated in three different ways, either by measuring the absorbance of the different suspensions at 480 nm, by weighing the amount of nanoparticles or magnetosomes after lyophilization or by measuring the saturating magnetization of 20 µl of each suspension deposited on top of a substrate using SQUID magnetometer measurement (Alphandéry et al., *J. Phys. Chem. C,* 2008, 112, 12304-12309). These three different types of measurements yielded the same estimate of the concentration for the suspensions containing individual magnetosomes and SPION. For the suspension containing the chains of magnetosomes, the presence of biological material surrounding the bacterial magnetosomes led to an overestimate of the maghemite concentration by absorbance and lyophilization. Therefore the concentration of this suspension was determined using SQUID measurements. For the treatment with the whole magnetotactic bacteria, the bacterial concentration injected was $10^8$ cells in 100 µl.

The concentration of bacterial cells was chosen so that it yielded the same iron oxide concentration than that of suspension 2.

Histological examinations were carried out in subcutaneous tumor, liver, kidneys and lungs collected 30 days after the first injection. Samples were fixed in 10% formalin solution, embedded in paraffin and sectioned into slices of thickness 4 µM. The sections were stained with hematoxylin-eosin (HE) and with Berlin blue to detect the presence of the bacterial magnetosomes dyed in blue. Necrosis of neoplastic cells, the number of mitoses per 3 randomly selected fields at a magnification of ×400 in non necrotic area and the amount of pigmented cells were evaluated in pathological sections of the tumors localized on the right flank of the mice.

In order to shed light on histological examinations and to study internalization of the magnetosomes within tumor cells, $5.10^5$ breast carcinoma cells (MDA-MB-231 lines) have been seeded on microscopy slide cover. They grew during 48 hours at 37° C. in 5% $CO_2$. Cells were further treated in the presence of various suspensions of magnetosomes during 1 to 24 hours in the absence or in the presence of a magnetic field of 0.6 mT. Two milliliters of the two suspensions of magnetosomes, containing either individual magnetosomes or chains of magnetosomes mixed in the cell growth medium, were used. In order to avoid too high cytoxicity of the cells, the iron oxide concentration of the two suspensions of magnetosomes was kept low at ~130 $\mu g \cdot ml^{-1}$. After treatment, the cells were washed with PBS to remove the bacterial magnetosomes surrounding the cells. The cells were then fixed using 5% of paraformaldehyde and were incubated in the presence of a solution, which becomes colored in Prussian blue in the presence of iron. This solution contains 5% potassium ferrocyanate and 10% hydrochloride acid (equivolume). The cells were then observed using an air objective (×100). The focalization of the objective was adjusted to detect the presence of iron within the cells and not at the cell surface.

Figure 11:
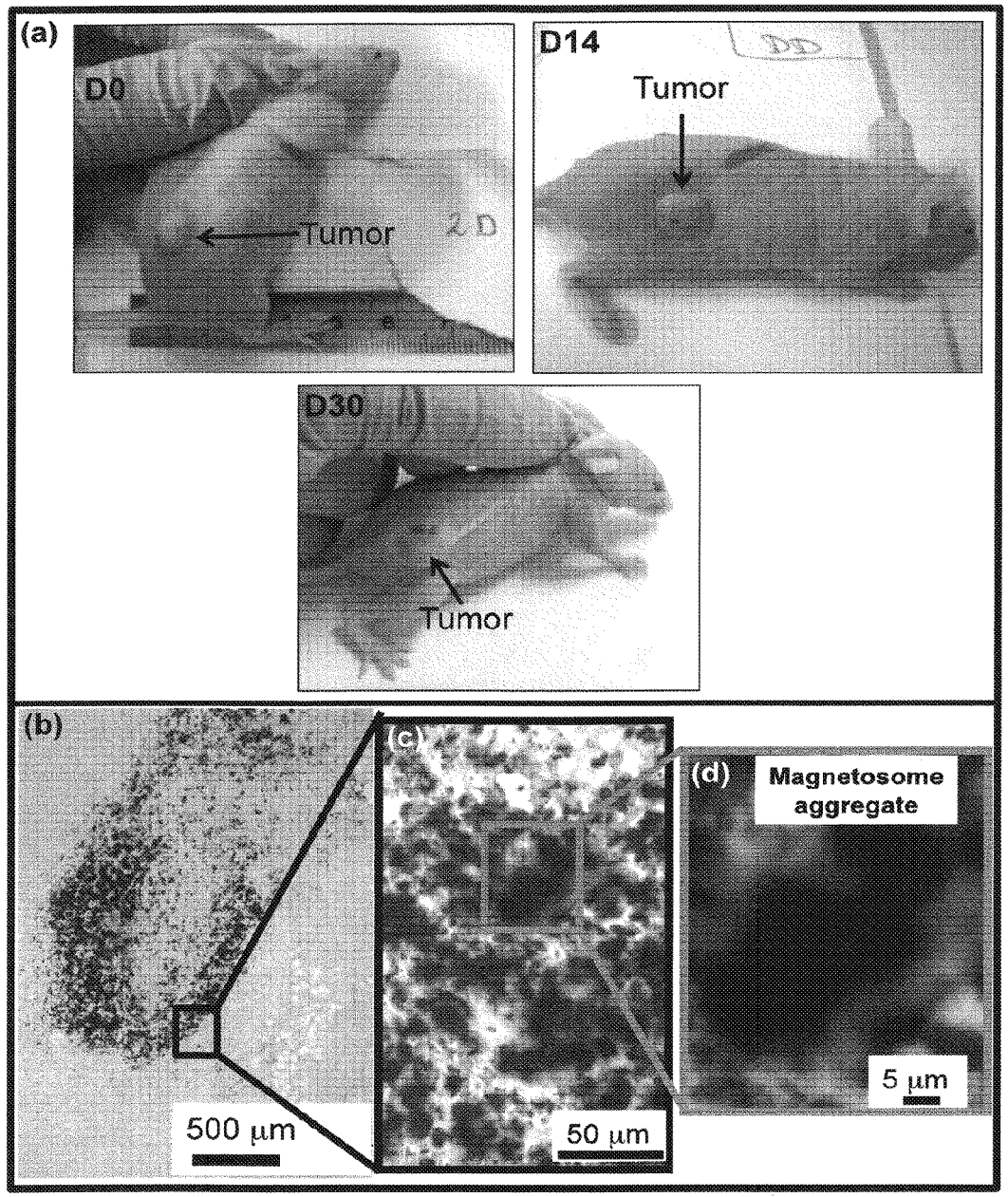
FIG. 11: Study of the mice treated with individual magnetosomes (mice 1 to 4). (a) Photographs of the treated tumor in mouse 1 just after the treatment (D0), 14 days after the treatment (D14) or 30 days after the treatment (D30). (b) Micrograph of a tumor tissue collected 30 days after the treatment in mouse 2; (c) Enlargement of a region of (b) showing the presence of bacterial magnetosomes (blue color or dark contrast); (d) Enlargement of a region of (c) showing magnetosomes aggregates.

Results and Discussion:

In the first set of mice, the suspension containing the individual magnetosomes was injected and the alternating magnetic field was applied. As a result, the temperature within the tumor mice increased by 4° C. from 31° C. to 35° C. (FIG. 10(c)). After 10 min of heating, infra-red measurements showed that the temperature spread within the tumor is ~0.5 cm, where this distance is estimated by measuring the full width half maximum of the temperature distribution shown in FIG. 10(d). The evolutions of the sizes of the treated tumors are shown in FIG. 10(e). These sizes increased in mice 1 to 3 during the 30 days following the treatment, indicating the absence of antitumoral activity. The increase of the treated tumor size can also be observed in mouse 3 by examining the set of three photographs taken during the day of the treatment (D0), 14 days after the treatment (D14) and 30 days after the treatment (D30) (FIG. 11(a)). The absence of antitumoral activity in these mice was further confirmed by the behaviors of the tumors, which did not receive the individual magnetosomes (FIG. 10(f)). The sizes of these tumors increased at a similar rate than those of the treated tumors (FIGS. 10(e) and 10(f)). When suspension 1 was injected without application of a magnetic field (in mouse 4 and in two other mice), the tumor size also increased (FIG. 10(f)). Together these results indicate that neither the presence of the individual magnetosomes nor the heat that they generate in the presence of a magnetic field produce antitumoral activity.

Pathological examinations of the tumor localized on the right flank of mouse 2 further confirmed this conclusion. They showed an important mass of necrotic cell in tumors collected 30 days after the first treatment. Mitoses were numerous and indicated an important tumor proliferative activity with an average of 12 mitoses per selected field of 300 $\mu m^2$ in size. The Berlin blue staining of a pathological section obtained from the right tumor showed the presence of diffused dark spots (FIG. 11(b)). These spots are presumed to arise from magnetosomes aggregates as shown in enlarged views (FIGS. 11(c) and 11(d)). Histological analysis of organs showed that no individual magnetosomes were found in liver, kidneys and lungs. The absence of the individual magnetosomes within these organs suggests that they remain localized within the tumors 30 days after injection, probably because of their tendency to aggregate.

In order to study if the individual magnetosomes penetrate within carcinoma cells, the latter were incubated in the presence of a suspension of individual magnetosomes. After 1 hour of incubation, there are only few traces of individual magnetosomes located inside the cells both in the absence and in the presence of a magnetic field. After 24 hours of incubation of the cells, no more traces of individual magnetosomes were observed both in the absence and in the presence of a magnetic field. This suggests that the individual magnetosomes don't easily penetrate within the tumor cells. When they do penetrate, they don't remain localized within these cells for a long period of time.

Figure 12:
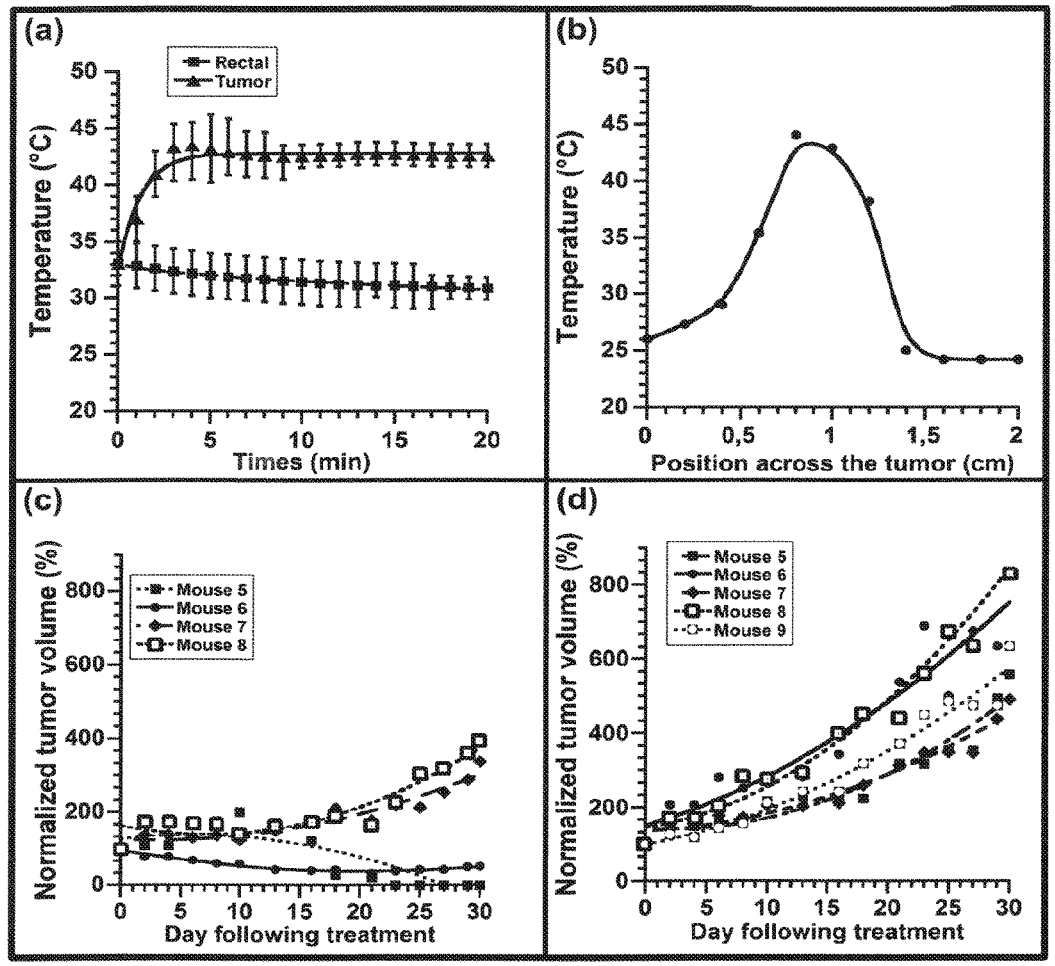
FIG. 12: Study of the mice treated with suspensions containing chains of magnetosomes (mice 5 to 9). (a) The variations of the tumor and rectal temperatures when the magnetic field is applied during the treatment (mice 5 to 8). The temperature is averaged over the different mice (mice 5 to 8); (b) For a mouse showing a typical behavior, temperature distribution measured across the treated tumor 10 min after the beginning of the treatment; (c) Evolution of the normalized tumor volume for the tumor in which the suspension containing the chains of magnetosomes has been injected. The volume of the treated tumor is normalized by the volume of the tumor at the time of the treatment; (d) Same as in (c) for the control tumor in which only PBS has been injected. In mouse 9, the suspension containing the chains of magnetosomes has been injected but no magnetic field has been applied to the mouse.
Figure 13:
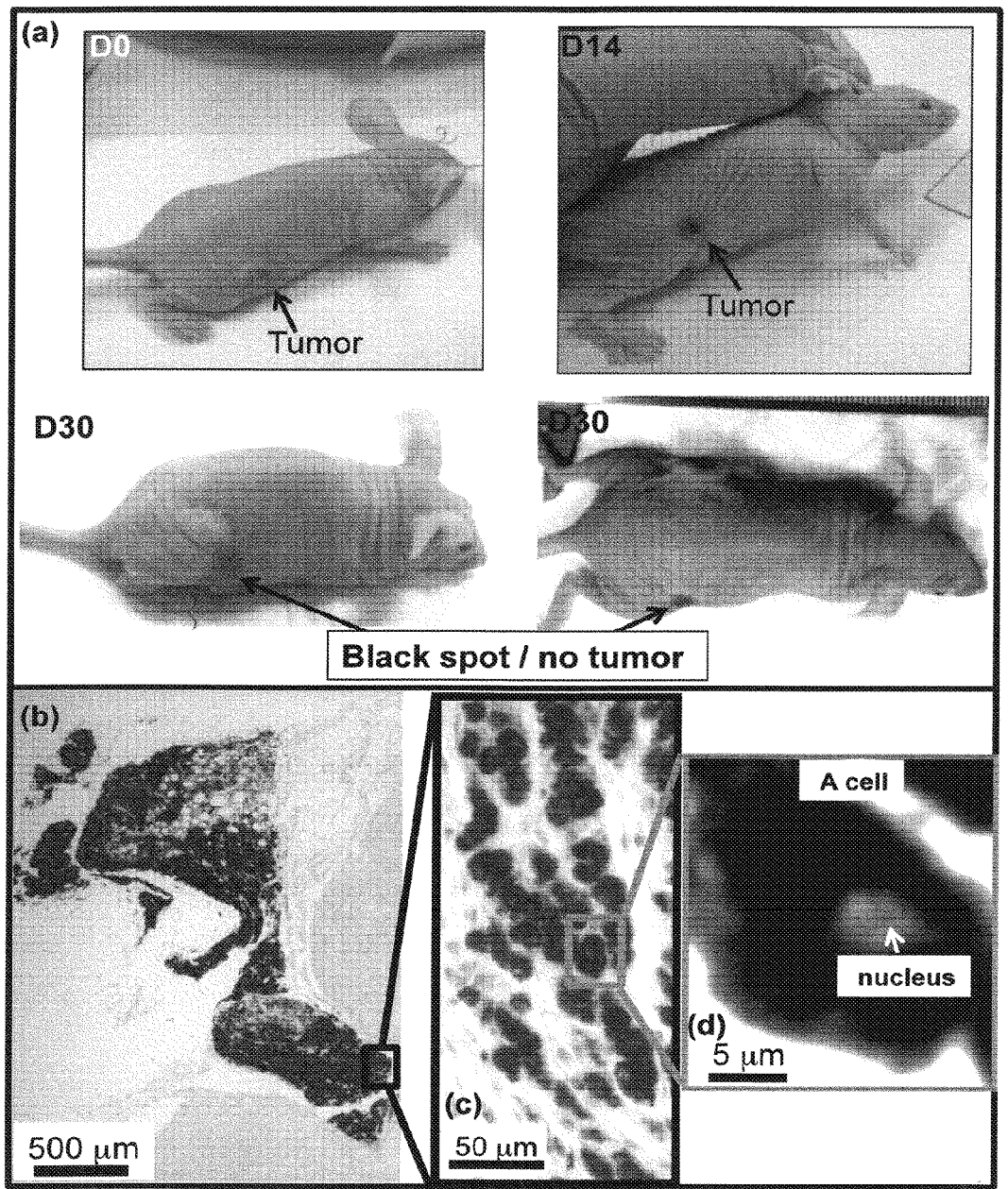
FIG. 13: Study of the mice treated with suspensions of chains of magnetosomes (mice 5 to 9). (a) Photographs of the treated tumor in mouse 5 just after the treatment (D0), 14 days after the treatment (D14), 30 days after the treatment (D30). (b) Micrograph of a tumor tissue collected 30 days after the treatment in mouse 5 showing the presence of the bacterial magnetosomes (blue color or dark contrast); (c) Enlargement of (b). (d) Enlargement of (c) showing a cell with its nucleus surrounded by bacterial magnetosomes.

In the second set of mice, the suspension containing the chains of magnetosomes was injected. Unexpectedly, the application of the magnetic field produced a larger increase in temperature than that observed in the first set of mice. In 20 min, the temperature within the tumor increased by 10° C. from 33° C. to 43° C. (FIG. 12(a)). In addition, infra-red images show a larger spread of temperatures through the tumor cross-section. FIG. 12(b) shows that the full width half maximum of the temperature distribution is 0.75 cm, suggesting a more homogenous temperature distribution within the tumors for the chains of magnetosomes than for the individual magnetosomes. By contrast to the behaviors observed with the individual magnetosomes, the antitumoral activity was clear in this case. FIG. 12(c) shows that the sizes of the treated tumors did not strongly increase as it is observed for the untreated tumors (FIG. 12(d)). The treated tumor disappeared completely in mouse 5 and was very significantly reduced in size in mouse 6 (FIG. 12(c)). The disappearance of the treated tumor in mouse 5 can be seen by examining the set of three photographs taken during the day of the treatment (D0), 14 days after the treatment (D14) and 30 days after the treatment (D30) (FIG. 13(a)). In addition, histological examinations showed that there was no remain of tumor tissues in mouse 5. Pathological examinations of the treated tumors showed that the number of observed mitosis was low (4 in average by selected field of 300 µm²) indicating a decrease in the activity of tumor proliferation. In mouse 9 and in two other mice, where the suspension of chains of magnetosomes was injected without application of the magnetic field, the tumor size increased strongly during the 30 days following the first treatment (FIG. 12(d)). This indicates that the antitumoral activity was due to the heat released by the chains of magnetosomes when they were exposed to an alternating magnetic field. A micrograph of a tumoral tissue shows a more homogenous distribution of the chains of magnetosomes compared with that of the individual magnetosomes (FIGS. 11(d) and 13(b)). In addition, the enlargements of FIG. 13(b), which are shown in FIGS. 13(c) and 13(d), show a black region surrounding the cell nucleus. This suggests that the chains of magnetosomes have penetrated within the cells (a result, which agrees with the conclusion drawn in example 4). The histological examinations of the organs also suggest the presence of sporadic chains of magnetosomes, which were detected in hepatocytes and perivascular liver cells but not in kidney and lungs. Despite the accumulation of chains of magnetosomes in liver cells, no lesions were observed in liver.

In order to confirm the results obtained from the histological examinations, the chains of magnetosomes were incubated in vitro in the presence of carcinoma cells. After 1 hour of incubation, the presence of the chains of magnetosomes within the cells was observed more clearly than that of the individual magnetosomes both in the absence and in the presence of a magnetic field. For an incubation time of the cells of 24 hours, the presence of the chains of magnetosomes within the cells becomes even more pronounced. In the presence of a magnetic field, the chains of magnetosomes are localized around the cell nucleus, whereas in the absence of a magnetic field, the chains of magnetosomes are dispersed more randomly within the different cellular compartments. These results suggest that it may be possible to target the tumor cells with a magnetic field using chains of magnetosomes.

Figure 18:
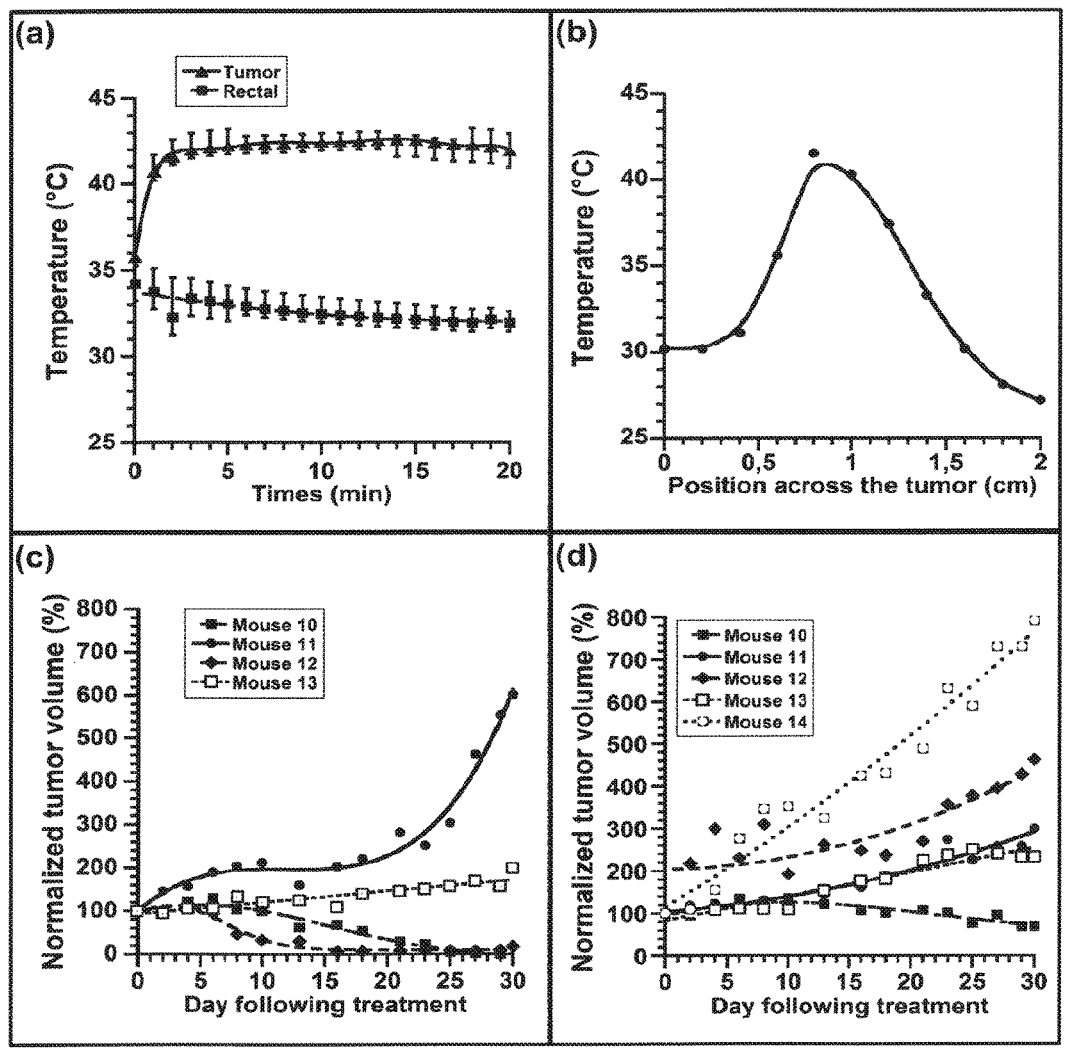
FIG. 18: For the mouse treated with SPION, the evolution of the temperature and tumor sizes (mice 10 to 13). (a) Evolution of the tumor and rectal temperatures during the treatment. The temperature is averaged over the different mice treated (mice 10 to 12); (b) For a mouse showing a typical behavior, temperature distribution measured across the treated tumor 10 min after the beginning of the treatment; (c) Evolution of the normalized tumor volume for the tumor in which the suspension of SPION@Citrate has been injected (mice 10 to 13). The volume of the treated tumor is normalized by the volume of the tumor at the time of the treatment; (d) same as in (c) for the control tumor in which only PBS has been injected. In mouse 14, the solution of SPION has been injected but no magnetic field has been applied to the mouse.

In the third set of mice, a suspension of SPION has been injected in the tumors localized on the right flank of the mice. The application of the magnetic field produced a slightly lower increase in temperature than that observed with the chains of magnetosomes. In 20 minutes, the temperature within the tumor increased by 6° C. from 36° C. up to 42° C. (FIG. 18(a)). The full width half maximum of the temperature distribution estimated by infrared measurements (0.75 cm, FIG. 18(b)) was the same as that observed with the chains of magnetosomes. In this case, the sizes of the treated tumors decreased very strongly in mice 10 and 12 (FIG. 18(c)), but histological examinations showed the presence of peritumoral lymph nodes, suggesting that the antitumoral activity was only partial in these mice. In mice 11 and 13, the sizes of the untreated and treated tumors increased at a similar rate showing no obvious antitumoral activity (FIGS. 18(c) and 18(d)). In mouse 14 and in two other mice, where the SPION were injected without application of a magnetic field, a strong increase of the tumor size was observed during the 30 days period following the injection (FIG. 18(d)). As in the second set of mice in which the suspension of chains of magnetosomes has been injected, the average number of mitosis was low (5 in average by selected field of 300 µm²) and the necrotic activity was comparable to that observed in the control group. According to the Berlin blue staining, the SPION, which were dyed in blue were found in liver, Küpffer cells, in macrophages and in pulmonary lymph node sinus. The presence of SPION in the lungs has already been observed (Zhou et al., *Biomaterials,* 2006, 27, 2001-2008). It is a sign of potential toxicity and is therefore a disadvantage for the development of a thermotherapy such as that described in this disclosure.

In the fourth set of mice, $10^8$ cells contained in 100 µl of PBS have been injected in the tumors localized on the right flank of the mice and a magnetic field of ~80 mT has been applied. In these conditions, the temperature increased by only 4° C. from 33° C. to 37° C. in 20 min. The increase in temperature was also observed using infra-red measurements. As in the group treated with individual magnetosomes, the sizes of the treated tumors increased during the 30 days following the treatment. Histological examination revealed a pigmented area in the treated tumor with a high mitotic activity (15 mitosis in average by selected field of 300 µm²), indicating the absence of antitumoral activity. No magnetotactic bacteria were found in liver, kidneys and lungs.

From these results, we can draw the following conclusions:

(i) No antitumoral activity has been observed when the suspensions containing the individual magnetosomes, the chains of magnetosomes and the SPION@Citrate were injected in the tumors of the mice without application of a magnetic field.

(ii) When the individual magnetosomes were administered within the tumors to start the treatment, a low in vivo heating capability and no antitumoral activity were observed. This is unexpected in view of the heating capacity observed in solution (example 2).

(iii) By contrast, when the chains of magnetosomes were administered within the tumors to start the treatment, a significant antitumoral activity was observed when they were heated. This behavior may be explained by their high in vivo heating efficiency, by their homogenous distribution within the tumor of the mice and also by their faculty to penetrate within the tumor cells.

(iv) The SPION, which are currently used for hyperthermia treatment also showed antitumoral activity. However, their antitumoral activity was less pronounced that that obtained with the chains of magnetosomes. In addition, the experimental data were obtained for a suspension of SPION with an iron oxide concentration, which was twice that used with the suspension containing the chains of magnetosomes. For two suspensions with a similar iron oxide concentration, one observes much lower heating and antitumoral efficiencies for an administration of the suspension containing SPION than for that containing the chains of magnetosomes (example 6).

Example 6

Heating Efficiency and Anti-Tumoral Activity of Chains of Magnetosomes Prepared by Cultivating the Magnetotactic Bacteria either in the Absence or in the Presence of EDTA Compared with that of SPION@PEG and SPION@Citrate.

In this example, the heating efficiency and antitumoral activity of chains of magnetosomes extracted from magnetotactic bacteria, which have been prepared by cultivating the bacteria either in the absence of a chelating agent or in the presence of 0.4 µM EDTA are compared. Moreover, the heating efficiency and antitumoral activity of these two types of bacterial magnetosomes are also compared with those of SPION@PEG and SPION@Citrate used by other groups to carry out magnetic hyperthermia.

Materials and Method:

The experimental protocol is very similar to that described in example 5, except that in this case the different types of nanoparticles were injected only once at the beginning of the treatment. 100 μl of the four different suspensions containing 10 mg/ml in iron oxide of the different types of nanoparticles were first injected within the tumors located on the right flank of the mice. The tumors located on the left flank of the mice were used as internal control. The treatment induced by heat was started by applying an alternating magnetic field of frequency 183 kHz and field amplitude of 43 mT. In one case, i. e. for the magnetosomes prepared in the presence of EDTA, the strength of the magnetic field was decreased below 43 mT to avoid that the temperature exceeds 50° C. The treatment was repeated 3 times at 3 days interval. The size of the tumor was measured during the 30 days following the treatment to evaluate the efficiency of the therapy.

The suspensions containing the extracted chains of magnetosomes, SPION@PEG and SPION@Citrate were prepared as described in example 1. AMB-1 magnetotactic bacteria were cultivated either in the presence or in the absence of 0.4 μM EDTA and the chains of magnetosomes were extracted following the same protocol as that described in example 1. The chains of magnetosomes prepared by cultivating the magnetotactic bacteria in the absence of EDTA are designated as "standard chains of magnetosomes" or CM while those prepared by cultivating the magnetotactic bacteria in the presence of 0.4 μM EDTA are designated as magnetosomes-EDTA or CM (EDTA 0.4 μM). The magnetosomes-EDTA are characterized by larger magnetosomes, by longer chains of magnetosomes and by a higher heating capacity (when they are mixed in water) than the CM as shown in example 3.

Figure 14:
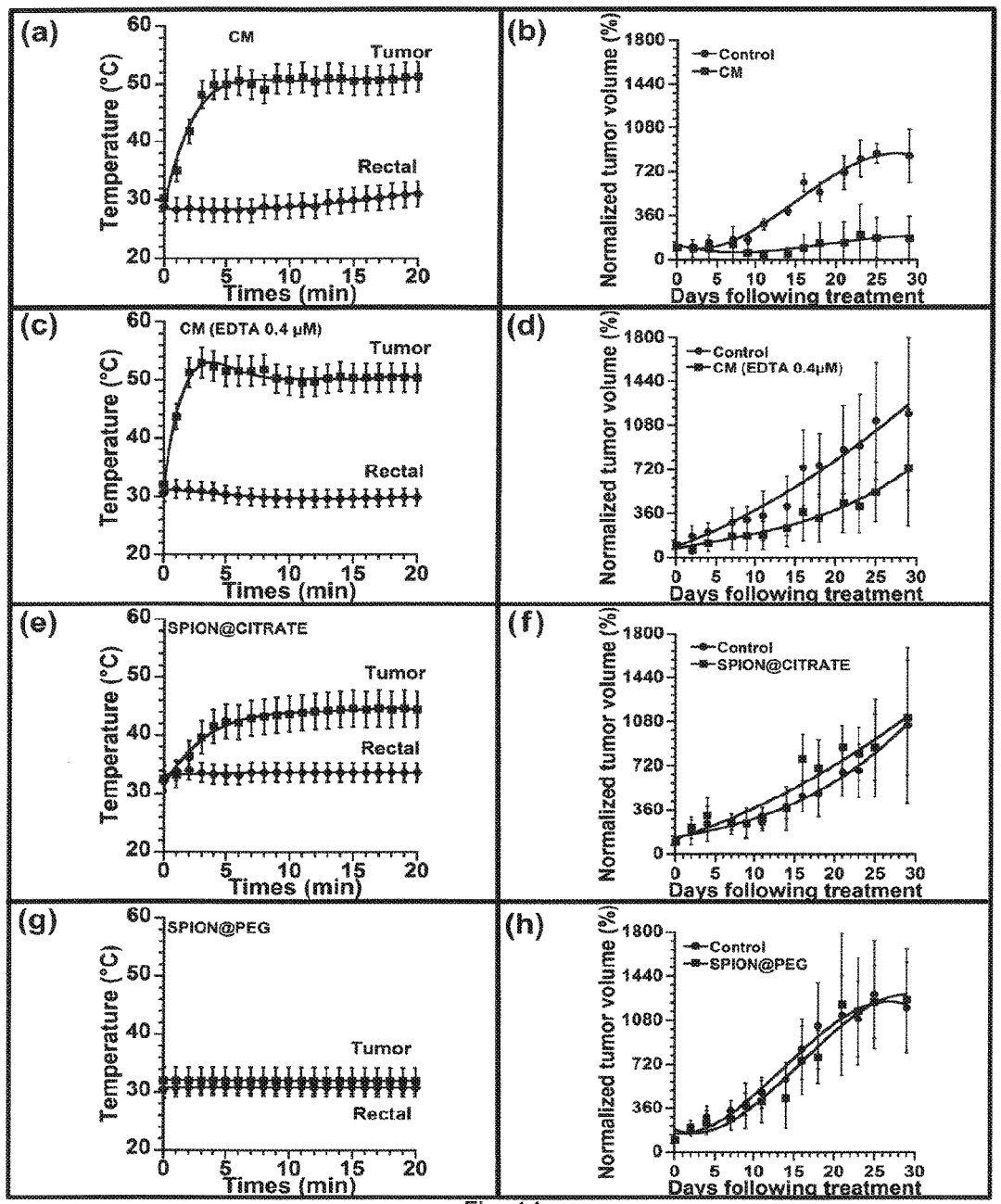
FIG. 14: (a), (c), (e), (g): Variations of the tumor and rectal temperatures when the suspensions containing the standard chains of magnetosomes, (a), the magnetosomes-EDTA, (c), the SPION@Citrate, (e), or the SPION@PEG, (g), are administered within the tumor and the alternating magnetic field of frequency 183 kHz and strength 43 mT is applied during 20 minutes. The treatment is repeated 3 times with a 1 day resting time between the different treatments. (b), (d), (f), (h): Variations of the normalized tumor volume (i. e. the tumor volume measured at day 2 to day 30 following the treatment divided by the tumor volume measured during the day of the treatment) during the days following the treatment for the standard chains of magnetosomes, (b), the magnetosomes-EDTA, (d), the SPION@Citrate, (f), or the SPION@PEG, (h). In (b), (d), (f) and (h), the error bars are the standard deviations estimated by taking into account the normalized tumor volume of each mouse.

Results and Discussion:

When 1 mg of a suspension containing the CM is injected within the tumor and the alternating magnetic field is applied, FIG. 14(a) shows that the temperature within the tumor reaches 50° C. after 4 minutes of treatment. During the 30 days following the treatment, FIG. 14(b) shows that the normalized tumor volume, which is averaged over the different mice treated, increases much less than that of the volume of the untreated tumor. For the mouse, which has been treated the most efficiently, the tumor disappears completely as indicated by the variation of the tumor volume in this mouse (FIG. 15(b)) and by the photograph of this tumor taken 30 days after the treatment (FIG. 15(a)). Clear anti-tumoral activity is observed with the CM, hence confirming the results presented in example 5. When the suspension of magnetosomes-EDTA is administered within the tumor and the magnetic field is applied, the temperature within the tumor increases more rapidly than after administration of the CM as observed by comparing FIGS. 14(a) and 14(c). This behavior agrees with the fact that the magnetosomes-EDTA possess a higher heating capacity than the CM when they are mixed in solution (example 3). However, despite the fact that the magnetosomes-EDTA show a better in vivo heating capacity than the CM, their anti-tumoral activity is lower. Indeed, FIG. 14(d) shows that the volume of the tumor treated with the magnetosomes-EDTA increases more than that of the tumor treated with the CM (FIG. 14(b)).

Figure 15:
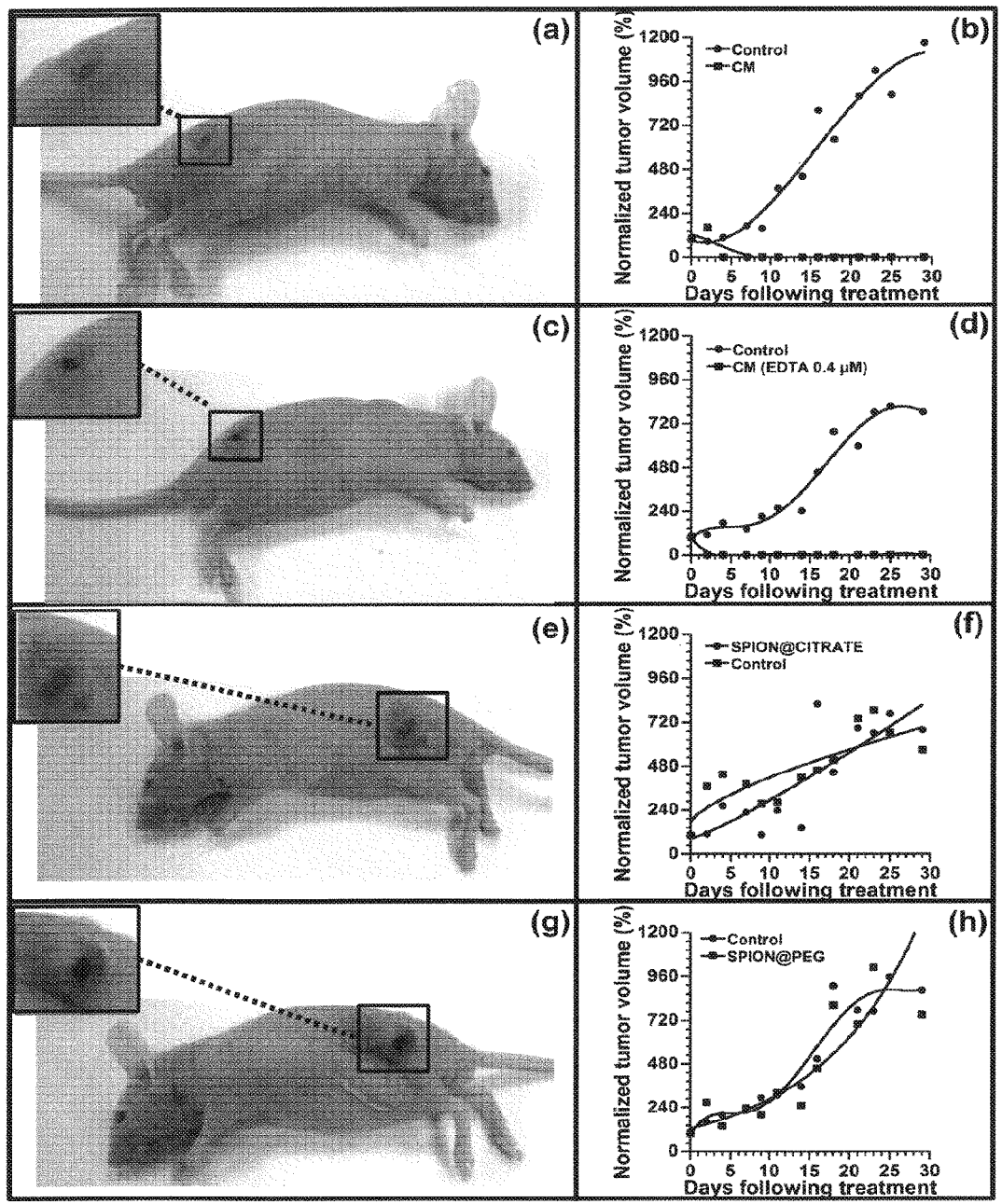
FIG. 15: (a), (c), (e), (g): Photographs of the mice, which showed the best anti-tumoral activity 30 days after the treatment induced by heat for the treatment carried out using the standard chains of magnetosomes, (a), the magnetosomes-EDTA, (c), the SPION@Citrate, (e), or the SPION@PEG, (g). (b), (d), (f), (h): The variations of the normalized tumor volume during the days following the treatment for the mice showing the best anti-tumoral activity and treated with standard chains of magnetosomes, (b), magnetosomes-EDTA, (d), SPION@Citrate, (f) and SPION@PEG, (h).

FIG. 15 depicts the behaviors of the mice for which the treatments were the most efficient in each group. A complete disappearance of the tumor was observed with the CM and with the magnetosomes-EDTA (FIGS. 15(c) and 15(d)), suggesting an anti-tumoral activity for the chains of magnetosomes of various lengths.

When 1 mg of a suspension containing the SPION@Citrate is administered within the tumor and the alternating magnetic field of 43 mT is applied, FIG. 14(e) shows that the temperature increases by 4° C. in 2 minutes, which is much less than the increase in temperature observed for the CM (12° C. in 2 minutes) or the magnetosomes-EDTA (20° C. in 2 minutes). In this case, the volume of the treated tumor increases at the same rate as that of the untreated tumor during the days following the treatment (FIG. 14(f)) and none of the mice shows a complete disappearance of the tumor during the 30 days following the treatment. For a typical mouse treated with the SPION@Citrate, the tumor is still there 30 days after the treatment (FIGS. 15(e) and 15(f)). This indicates a less efficient treatment than that involving the chains of magnetosomes. For injection of the SPION@PEG, the temperature within the tumor of the mice does not increase at all after application of the magnetic field as shown in FIG. 14(g) and none of the tumors decrease in sizes during the days following the treatment (FIGS. 14(h), 15(g) and 15(h)).

From these results, we can draw the following conclusions:
(i) When various suspensions of nanoparticles containing the same quantity of iron oxide are administered, the suspensions containing the extracted chains of magnetosomes show a better heating efficiency and anti-tumoral activity than those containing the SPION@PEG and SPION@Citrate.
(ii) The higher anti-tumoral activity produced by the CM compared with the magnetosomes-EDTA may be explained by a better intra-cellular uptake of the CM than magnetosomes-EDTA. This is most probably due to the difference in chain lengths between these two types of magnetosomes. Since intra-cellular hyperthermia is thought to be a more efficient mechanism of cellular destruction than extracellular hyperthermia, this difference in internalization between these two types of magnetosomes could explain the difference in anti-tumoral activity.

Example 7

Biodistribution of Various Bacterial Magnetosomes in Mice

In this example, the biodistribution of various types of particles (chains of magnetosomes, individual magnetosomes, SPION@citrate and SPION@PEG) contained within the different organs of mice just after the injection, 3 days, 6 days or 14 days after the injection is studied. For this study, various suspensions containing 1 mg of each type of the nanoparticles mentioned above have been injected intratumoraly, i. e. directly within the tumors of the mice.

We only show the percentage of particles within the tumors and feces of the mice since the particles were essentially found there. For the estimates of the percentage of particles within the tumors, two types of magnetic measurements were carried out (MIAtek and SQUID). In addition of these two types of measurements, the specific absorption rate (SAR) of the various particles was measured ex-vivo for the tumors heated under the application of the alternating magnetic field. Since the SAR is inversely proportional to the amount of particles heated (see example 2), this measurement enables an estimate of the quantity of particles injected within the tumors.

Materials and Method:

Induction of human breast tumor was carried out as previously reported in the example 5. Briefly, 54 female Swiss nude mice of 6 week of age (Charles River, Arbresle, France) received by subcutaneous injection two millions of MDAMB231 human breast cancer cells (Cailleau et al., *J. Natl. Cancer Inst.*, 1974, 53, 661-674) both on the left and right flanks. The injection of the various types of particles has been carried out 14 days after tumor implantation. A suspension of chains of magnetosomes, individual magnetosomes, SPION@citrate and SPION@PEG (Micromod, Rostock-Warnemuende, Germany) has been prepared at the concentration of 10 mg Fe/mL. 100 µl of these suspensions have been injected directly within the tumors localized on the right flank at the dose of 1 mg of maghemite. The amount of maghemite contained within the different organs of the mice has been measured during the day of the injection (day 0, D0), three days after the injection (day 3, D3), six days after the injection (day 6, D6) or 14 days after the injection (day 14, D14). At the different days (D0, D3, D6 or D14), the animals were euthanized by cervical dislocation and the tissues or organs of interest (blood, liver, spleen, lungs, kidneys, tumor, feces) were collected immediately, weighted and frozen at 4° C. until analysis. First, the heating efficiency of the different tumors containing the various types of particles and collected at different days was tested ex-vivo. For that, the tumoral tissue was inserted within a tube, which was then positioned inside a coil where the alternating magnetic field of frequency 183 kHz and field strength of 43 mT was applied during 20 minutes (EasyHeat 10 kW, Ambrell, Soultz, France). The temperature within the tumor was measured using an implantable thermocouple microprobe (IT-18, Physitemp, Clifton, USA). Second, the quantity of maghemite was determined using an instrument, the MIAtek®, which has been developed by the Company Magnisense (Nikitin et al., 2007, *J. Magn. Mater.* 311, 445). This technology enables sensitive detection and precise quantification of magnetic nanoparticles in a biological target. For the measurements with the MIAtek®, the tissues were prepared by mechanical homogenization in ultrapure water (16% of feces wet weight, i. e 16 g of feces diluted in 100 ml of PBS, 25% of tumor wet weight, 50% of kidney, lung, spleen wet weight and 100% liver wet weight). 100 µL of tissues prepared in this way were placed into the detection system (MIAtek). The calibration was carried out by measuring the MIAtek® signal of suspensions containing chains of magnetosomes, individual magnetosomes, SPION@Citrate and SPION@PEG mixed in water as a function of the maghemite concentration of these suspensions, which was varied between 15 µg/mL and 125 µg/mL. In order to verify the estimates of the maghemite concentrations with the MIAtek®, SQUID measurements have been carried on the samples containing the highest percentage of maghemite (the tumors and the feces). For that the saturating magnetization of the different tumors and feces containing the various types of particles was estimated. From this estimate, we could deduce the quantity of maghemite present in the different samples using the saturating magnetization of bulk maghemite (80 emu/g). The estimates deduced from the MIAtek® measurements have been compared with those deduced from the SQUID measurements. Finally, the different tumors containing the various types of particles have been heated ex vivo under the application of an alternating magnetic field of frequency 183 kHz and field strength of 43 mT. From the heating curves, we could deduce the SAR by measuring the slopes at 25° C. and hence the quantity of maghemite contained within the different tumors (example 2).

The estimates of the quantity of maghemite contained within the different tumors have been obtained by collecting one fifth of the total tumor volume after homogenization of the particles within the tumors. Most probably because of a non uniform homogenization, the collected tumor does not contain one fifth of the amount of the various types of particles injected. This results in large error bars in the measurements and in some cases in the detection of more particles within the tumor than the amount, which has been injected. However, despite of these uncertainties, the main conclusions drawn in this study remain valid.

Figure 16:
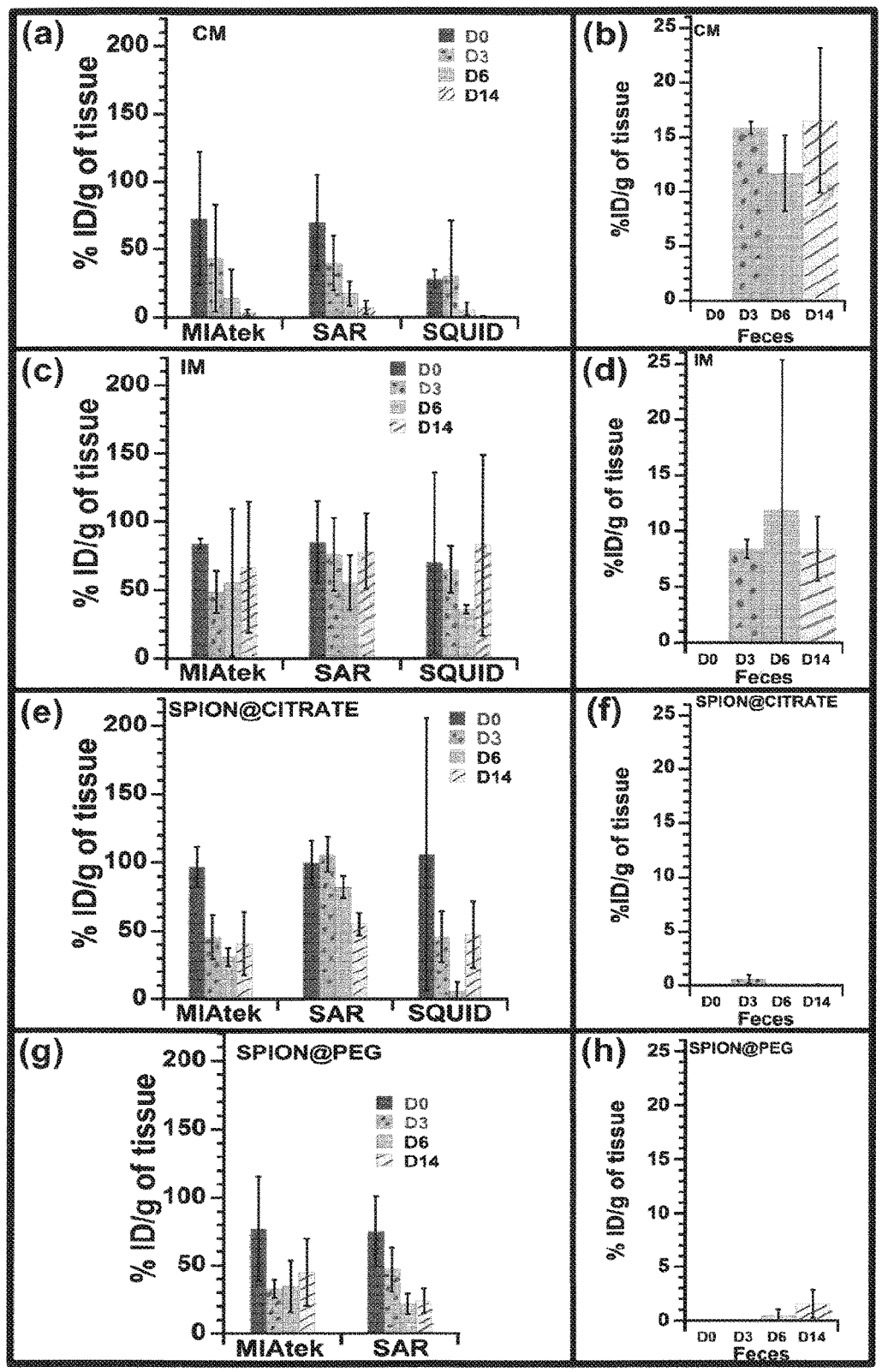
FIG. 16: Percentage of nanoparticles in the tumor ((a), (c), (e), (g)) and in the feces ((b), (d), (f), (h)) at the time of the injection (D0), 3 days after the injection (D3), 6 days after the injection (D6) and 14 days after the injection (D14) for an intra-tumoral administration of suspensions containing either chains of magnetosomes, (a), (b), individual magnetosomes, (c), (d), SPION@Citrate, (e), (f), and SPION@PEG, (g), (h).

Results and Discussion:

FIG. 16(*a*) shows the biodistribution of the chains of magnetosomes within the tumors (estimated as the percentage of injected dose per gram of tissue) just after the injection (D0), 3 days after the injection (D3), 6 days after the injection (D6) and 14 days after the injection (D14). The three types of measurements (MIAtek®, SAR and SQUID) show essentially the same trend: the rapid decrease of the percentage of chains of magnetosomes contained within the tumors during the days following the injection (FIG. 16(*a*)). Indeed more than 90% of the chains of magnetosomes have been eliminated 14 days after the injection. The chains of magnetosome were found essentially in the feces with 10-15% in the feces at the first day post-injection and 15 to 20% at 3 days, 6 days and 14 days post-injection (FIG. 16(*b*)). With the chains of magnetosomes, the route of elimination has been shown to be essentially fecal. Only few traces of chains of magnetosomes (<0.1% ID/g of tissue) were found in the lung, kidney, liver and spleen the third and sixth days after the injection. No chains of magnetosome were found in the blood. These results suggest that the chains of magnetosome were rapidly excreted in their native form.

For the injection of the individual magnetosomes, the percentage of injected dose (I.D.) per gram of tissue is shown in FIG. 16(*c*) at the different days post-injection. As for the chains of magnetosomes, there is relatively good agreement between the three different types of measurements (MIAtek®, SAR and SQUID). The percentage of individual magnetosomes contained within the tumor seems to decrease much less significantly during the days following the treatment than that of the chains of magnetosomes (FIGS. 16(*a*) and 16(*c*)). As for the chains of magnetosomes, individual magnetosome were found in the feces but with a lower percentage (between 5 and 10% at D3, D6 and D14). The route of elimination of the individual magnetosome also appears to be (at least partly) the fecal excretion.

The biodistribution of chemically synthesized SPION@Citrate and SPION@PEG has also been studied. As shown in FIGS. 16(*e*) and 16(*g*), the SPION@Citrate and SPION@PEG appear to remain within the tumors 14 days following the injection. The percentage of nanoparticles within the tumors does not decrease during the days following the treatment as significantly as with the chains of magnetosomes Moreover, SPION@Citrate and SPION@PEG have not been detected in the feces of the mice. These results may be explained by the fact that the SPION@citrate and the SPION@PEG are metabolized in free iron and are therefore not eliminated in the feces as nanoparticles. This would rather be a drawback of these chemically synthesized nanoparticles compared with the magnetosomes since free iron can cause oxidative stress (Puntarulo et al., 2005, Mol. Aspects, Med., 299-312).

From these results, we can draw the following conclusions:

The chains of magnetosomes leave rapidly the tumor and seem to be eliminated in the feces. Both of these properties are favorable for the development of the thermotherapy described in this disclosure. We could tentatively explain this behavior by the fact that the chains of magnetosomes do not strongly aggregate. By contrast to the chains of magnetosomes, a large percentage of individual magnetosomes remain within the tumor 14 days post-injection, which suggest that the organism might find it more difficult to eliminate them rapidly. We could tentatively explain this behavior by the fact that the individual magnetosomes aggregate. A large percentage of the chemically synthesized nanoparticles (SPION@Citrate and SPION@PEG) remain within the tumor 14 days post-injection and none of them is found in the feces. This suggests that these chemically synthesized nanoparticles don't rapidly leave the tumors and that they metabolize in iron and/or that they are eliminated in the urines. These features make them potentially less attractive drug candidates than the chains of magnetosomes.

The invention claimed is:

1. A method of treating a tumor or tumor cells by heat therapy in a subject in need thereof, comprising administering chains of bacterial magnetosomes, to the subject, wherein:
   the chains of magnetosomes comprise maghemite,
   the chains of magnetosomes have been isolated from magnetotactic bacteria, and
   the chains of magnetosomes in a suspension at at least one particular pH yield magnetosomes with at least one property selected from the group consisting of:
   i) the magnetosomes have a lower surface charge at a pH of 10 than at a pH of 2, and
   ii) the magnetosomes have a surface charge between −35 mV and 20 mV at at least one pH within a pH range from a pH of 2 to a pH of 10.

2. The method according to claim 1, wherein the chains of magnetosomes are subjected to an alternating magnetic field to yield the generation of heat.

3. The method according to claim 2, wherein the alternating magnetic field has a frequency between 50 kHz and 1000 kHz.

4. The method according to claim 2, wherein the alternating magnetic field has an amplitude between 0.1 and 200 mT.

5. The method according to claim 2, wherein the alternating magnetic field is applied during a time period varied between 1 second and 6 hours.

6. The method according to claim 2, wherein administering the chains of magnetosomes to said subject comprises administering the chains of magnetosomes within the tumor cells of said subject, and the alternating magnetic field is applied to improve the penetration of the chains of magnetosomes within the tumor cells.

7. The method according to claim 1, wherein the chains of magnetosomes contain at least 2 magnetosomes.

8. The method according to claim 1, wherein the magnetosomes contained within the chains possess sizes lying between 5 and 120 nm.

9. The method according to claim 1, wherein the chains of magnetosomes have been isolated from magnetotactic bacteria that were cultivated in a growth medium containing a metal selected from the group consisting of iron, a transition metal other than iron, and a combination thereof.

10. The method according claim 1, wherein the chains of magnetosomes have been obtained from magnetotactic bacteria that were cultivated in a growth medium containing a chelating agent.

11. The method according to claim 1, wherein the chains of magnetosomes possess an agent bound to the magnetosomes or incorporated within the magnetosomes, which is used to visualize the chains of magnetosomes.

12. The method according to claim 11, wherein said agent is a fluorophore or a fluorophore and a chelating agent.

13. The method according to claim 1, wherein the chains of magnetosomes are encapsulated within a vesicle, said vesicle being used in combination with an active principle.

14. The method according to claim 1, wherein the treatment of the tumor cells or of the tumor is hyperthermia.

15. The method according to claim 14, wherein the treatment is performed at a temperature between 37° C. and 45° C.

16. The method according to claim 1, wherein the treatment of the tumor cells or of the tumor is thermoablation.

17. The method according to claim 16, wherein the treatment is performed at a temperature between about 45° C. and about 100° C.

18. The method according to claim 1, wherein the heating therapy is repeated.

19. The method according to claim 1, wherein targeting of the tumor or tumor cells by the chains of magnetosomes is carried out by using a magnetic field.

20. The method according to claim 1, wherein targeting of the tumor or tumor cells is realized by attaching at least one of a biological targeting molecule or a chemical targeting molecule, which targets the tumor or tumor cell, to the chains of magnetosomes or to a vesicle containing the chains of magnetosomes.

21. The method according to claim 20, wherein the at least one of a biological targeting molecule or a chemical targeting molecule is selected from the group consisting of: an antibody, a PEG molecule, a folic acid and combinations thereof.

22. The method according to claim 1, wherein said tumor is selected from the group consisting of prostate cancer, esophageal cancer, pancreatic cancer, breast cancer, brain cancer and skin cancer.

23. A kit comprising:
   chains of bacterial magnetosomes wherein:
   the chains of magnetosomes comprise maghemite,
   the chains of magnetosomes have been isolated from magnetotactic bacteria, and
   the chains of magnetosomes in a suspension at at least one particular pH or within a pH range yield magnetosomes with at least one property selected from the group consisting of:
   i) the magnetosomes have a lower surface charge at a pH of 10 than at a pH of 2, and
   ii) the magnetosomes have a surface charge between −35 mV and 20 mV at at least one pH within a pH range from a pH of 2 to a pH of 10; and
   a device configured to generate an alternating field.

24. The kit according to claim 23, wherein the chains of magnetosomes are encapsulated within a vesicle.

25. A method for the production of chains of magnetosomes, comprising cultivating magnetotactic bacteria in a growth medium containing at least an iron source, with or without a chelating agent, wherein
   the chains of magnetosomes comprise maghemite, and
   the chains of magnetosomes in a suspension at at least one particular pH yield magnetosomes with at least one property selected from the group consisting of:
   i) the magnetosomes have a lower surface charge at a pH of 10 than at a pH of 2, and
   ii) the magnetosomes have a surface charge between −35 mV and 20 mV at at least one pH within a pH range from a pH of 2 to a pH of 10.

26. Chains of bacterial magnetosomes isolated from magnetotactic bacteria, said chains obtained by the method according to claim 25, wherein:
- the chains of magnetosomes comprise maghemite, and
- the chains of magnetosomes in a suspension at at least one particular pH yield magnetosomes with at least one property selected from the group consisting of:
- i) the magnetosomes possess a lower surface charge at a pH of 10 than at a pH of 2, and
- ii) the magnetosomes have a surface charge between −35 mV and 20 mV at at least one pH within a pH range from a pH of 2 to a pH of 10.

27. The method according to claim 25, further comprising extracting from the cultivated magnetotactic bacteria to obtain said chains of magnetosomes.

28. A composition comprising chains of bacterial magnetosomes, wherein:
- the chains of magnetosomes comprise maghemite,
- the chains of magnetosomes have been isolated from magnetotactic bacteria, and
- the chains of magnetosomes in a suspension at at least one particular pH yield magnetosomes with at least one property selected from the group consisting of:
- i) the magnetosomes possess a lower surface charge at a pH of 10 than at a pH of 2, and
- ii) the magnetosomes have a surface charge between −35 mV and 20 mV at at least one pH within a pH range from a pH of 2 to a pH of 10.

* * * * *